US012667482B2

(12) United States Patent
Sidoti et al.

(10) Patent No.: US 12,667,482 B2
(45) Date of Patent: Jun. 30, 2026

(54) FORMULATIONS, DEVICES, AND METHODS FOR ALLEVIATING SYMPTOMS OF OCULAR SURFACE DISCOMFORT

(71) Applicant: EyeCool Therapeutics, Inc., Cambridge, MA (US)

(72) Inventors: Charles Sidoti, Cambridge, MA (US); Tomasz Stryjewski, Cambridge, MA (US); James Stefater, Cambridge, MA (US); Olivier Kagan, Cambridge, MA (US); Sameer Sabir, Cambridge, MA (US); Katelyn Li, Cambridge, MA (US); Danielle Brucato, Cambridge, MA (US); Joseph Aaron, Cambridge, MA (US)

(73) Assignee: EYECOOL THERAPEUTICS, INC., Cambridge, MA (US)

( * ) Notice: Subject to any disclaimer, the term of this patent is extended or adjusted under 35 U.S.C. 154(b) by 0 days.

(21) Appl. No.: 19/048,089

(22) Filed: Feb. 7, 2025

(65) Prior Publication Data

US 2025/0177199 A1 Jun. 5, 2025

Related U.S. Application Data

(63) Continuation of application No. PCT/US2024/014354, filed on Feb. 2, 2024.

(Continued)

(51) Int. Cl.

*A61F 7/10* (2006.01)
*A61F 7/00* (2006.01)
*A61F 7/02* (2006.01)

(52) U.S. Cl.

CPC ........ *A61F 7/10* (2013.01); *A61F 2007/0004* (2013.01); *A61F 2007/0056* (2013.01);

(Continued)

(58) Field of Classification Search

CPC .................. A61F 9/0008; A61F 9/0017; A61F 2007/0004; A61F 2007/105; A61F 7/10

See application file for complete search history.

(56) References Cited

U.S. PATENT DOCUMENTS 2,101,628 A 12/1937 Padelford
2,313,282 A 3/1943 Tunke (Continued)

FOREIGN PATENT DOCUMENTS

CN 106214325 A 12/2016
CN 106344397 A 1/2017

(Continued)

OTHER PUBLICATIONS

No Author Listed, "Anesthesia For Eye Surgery: On Improving Retinal Anesthesia Technology," Bold Business article, Mar. 2, 2018 (https://www.Boldbusiness.Com/Health/Anesthesia-For-Eye-Surgery-Technology) (8 total pages).

(Continued)

*Primary Examiner* — Kaitlyn E Smith
(74) *Attorney, Agent, or Firm* — Wilmer Cutler Pickering Hale and Dorr LLP

(57) ABSTRACT

Disclosed herein are cold slurry formulations, devices, and methods for alleviating symptoms of ocular surface discomfort. Cold slurry formulations comprising ice, a freezing temperature depressant, and, optionally, a lipid are disclosed. Devices and methods for protecting a target ocular surface from contacting a cold slurry formulation that is used to maintain the target ocular surface at a temperature desired for alleviating symptoms of ocular surface discomfort are disclosed. Self-contained devices configured to receive a cold slurry formulation for maintaining the target ocular surface at a temperature desired for alleviating symptoms of ocular surface discomfort are disclosed. Devices and methods are disclosed for protecting a cornea and/or eyelid (Continued)

of a subject from the freezing cold slurry formulation that is directly or indirectly applied or injected into the target ocular surface. Kits comprising multiple syringes for administering multiple doses of the cold slurry to the target ocular surface, are disclosed.

29 Claims, 35 Drawing Sheets

Related U.S. Application Data

(60) Provisional application No. 63/443,082, filed on Feb. 3, 2023.

(52) U.S. Cl.
CPC ................. *A61F 2007/0215* (2013.01); *A61F 2007/0285* (2013.01); *A61F 2007/108* (2013.01)

(56) References Cited

U.S. PATENT DOCUMENTS

| | | | | |
|---|---|---|---|---|
| 2,796,903 | A | 6/1957 | Gazelle | |
| 3,762,419 | A | 10/1973 | Walters | |
| 4,068,918 | A | 1/1978 | Holcombe, Jr. | |
| 4,243,041 | A | 1/1981 | Paul | |
| 5,190,033 | A | 3/1993 | Johnson | |
| 5,368,590 | A | 11/1994 | Itoh | |
| 5,514,094 | A | 5/1996 | Anello et al. | |
| 5,953,097 | A | 9/1999 | Stark | |
| 6,099,521 | A | 8/2000 | Shadduck | |
| 6,241,711 | B1 | 6/2001 | Weissberg et al. | |
| 6,409,746 | B1 | 6/2002 | Igaki et al. | |
| 6,824,556 | B1 | 11/2004 | Lachance | |
| 7,930,772 | B2 | 4/2011 | Fontanez | |
| 8,257,256 | B1 | 9/2012 | Krolman | |
| 8,262,715 | B2 | 9/2012 | Wong, Jr. et al. | |
| 8,439,960 | B2 | 5/2013 | Burnett et al. | |
| 8,992,516 | B2 | 3/2015 | Muller | |
| 9,144,513 | B2 | 9/2015 | Paulson | |
| D787,694 | S | 5/2017 | Baltazar | |
| 9,956,355 | B2 | 5/2018 | Besirli et al. | |
| 10,201,471 | B2 | 2/2019 | Yang | |
| 10,238,814 | B2 | 3/2019 | Besirli et al. | |
| 10,322,248 | B2 | 6/2019 | Besirli et al. | |
| 10,369,056 | B2 | 8/2019 | Paulson | |
| 10,420,674 | B2 | 9/2019 | Johnson | |
| 11,241,330 | B1 | 2/2022 | Sabir et al. | |
| 11,399,882 | B2 * | 8/2022 | Stefater, III | A61F 9/0008 |
| 11,471,401 | B2 | 10/2022 | Garibyan et al. | |
| D968,627 | S | 11/2022 | Kim et al. | |
| 11,564,830 | B2 | 1/2023 | Garibyan et al. | |
| 11,653,969 | B2 | 5/2023 | Stefater, III et al. | |
| 2002/0049389 | A1 * | 4/2002 | Abreu | A61B 3/0058 600/318 |
| 2004/0249427 | A1 | 12/2004 | Nabilsi | |
| 2005/0120734 | A1 | 6/2005 | Yon | |
| 2007/0282282 | A1 * | 12/2007 | Wong, Jr. | A61N 1/306 604/294 |
| 2008/0148769 | A1 | 6/2008 | Higgins | |
| 2009/0275936 | A1 | 11/2009 | Muller | |
| 2011/0307041 | A1 | 12/2011 | Floyd | |
| 2013/0158637 | A1 * | 6/2013 | Sheikh | A61F 7/103 493/213 |
| 2014/0025144 | A1 | 1/2014 | Ragan | |
| 2014/0081361 | A1 | 3/2014 | Dhayan | |
| 2015/0165231 | A1 * | 6/2015 | Scheja | A61M 37/00 604/20 |
| 2016/0000600 | A1 | 1/2016 | Lee | |
| 2016/0279350 | A1 | 9/2016 | Besirli et al. | |
| 2017/0231816 | A1 | 8/2017 | Ryan | |
| 2017/0274011 | A1 | 9/2017 | Garibyan et al. | |
| 2017/0304558 | A1 | 10/2017 | Besirli et al. | |
| 2017/0368298 | A1 | 12/2017 | Bojanova | |
| 2018/0289533 | A1 | 10/2018 | Johnson et al. | |
| 2019/0015602 | A1 | 1/2019 | Besirli et al. | |
| 2019/0053939 | A1 | 2/2019 | Garibyan et al. | |
| 2019/0125579 | A1 | 5/2019 | Habib | |
| 2019/0167916 | A1 | 6/2019 | Besirli et al. | |
| 2019/0328753 | A1 | 10/2019 | Yee et al. | |
| 2020/0054483 | A1 | 2/2020 | Kim | |
| 2020/0100934 | A1 | 4/2020 | Ariano et al. | |
| 2020/0163797 | A1 | 5/2020 | Besirli et al. | |
| 2020/0206023 | A1 | 7/2020 | Pathak et al. | |
| 2020/0215144 | A1 | 7/2020 | Yang | |
| 2021/0007882 | A1 | 1/2021 | Kim | |
| 2021/0145500 | A1 | 5/2021 | Barken | |
| 2022/0218514 | A1 | 7/2022 | Azar et al. | |
| 2024/0207183 | A1 | 6/2024 | Sabir et al. | |

FOREIGN PATENT DOCUMENTS

| | | | |
|---|---|---|---|
| CN | 106691685 | A | 5/2017 |
| CN | 107280854 | A | 10/2017 |
| CN | 107736962 | A | 2/2018 |
| CN | 107773350 | A | 3/2018 |
| CN | 108272549 | A | 7/2018 |
| CN | 108524098 | A | 9/2018 |
| CN | 108743030 | A | 11/2018 |
| CN | 108814802 | A | 11/2018 |
| CN | 108815584 | A | 11/2018 |
| CN | 109077909 | A | 12/2018 |
| CN | 109077947 | A | 12/2018 |
| CN | 110025463 | A | 7/2019 |
| CN | 110215335 | A | 9/2019 |
| CN | 110279517 | A | 9/2019 |
| CN | 110393623 | A | 11/2019 |
| CN | 110393624 | A | 11/2019 |
| CN | 110433272 | A | 11/2019 |
| CN | 110755193 | A | 2/2020 |
| CN | 110809457 | A | 2/2020 |
| CN | 110882103 | A | 3/2020 |
| CN | 111096846 | A | 5/2020 |
| CN | 111297557 | A | 6/2020 |
| CN | 217366288 | U | 9/2022 |
| CN | 115957067 | A | 4/2023 |
| CN | 116439904 | A | 7/2023 |
| DE | 29712559 | U1 | 9/1997 |
| DE | 202013102909 | U1 | 9/2013 |
| DE | 202015102909 | U1 | 7/2015 |
| FR | 2909545 | A1 | 6/2008 |
| GB | 2537833 | A | 11/2016 |
| JP | H0661224 | U | 8/1994 |
| JP | 2007-511293 | A | 5/2007 |
| JP | 2017-526684 | A | 9/2017 |
| JP | 2019-506248 | A | 3/2019 |
| KR | 1020060084878 | A | 7/2006 |
| KR | 200422938 | Y1 | 8/2006 |
| KR | 2020100002818 | U | 3/2010 |
| KR | 2020100009316 | U | 9/2010 |
| KR | 20100107157 | A | 10/2010 |
| KR | 101107942 | B1 | 1/2012 |
| KR | 20130007077 | A | 1/2013 |
| KR | 101486160 | B1 | 1/2015 |
| KR | 101544610 | B1 | 8/2015 |
| KR | 101827457 | B1 | 2/2018 |
| KR | 101851179 | B1 | 4/2018 |
| MX | PA06005434 | A | 1/2007 |
| WO | WO-2001/039704 | A1 | 6/2001 |
| WO | WO-2005/049071 | A2 | 6/2005 |
| WO | WO-2007/102362 | A1 | 9/2007 |
| WO | WO-2010/039117 | A1 | 4/2010 |
| WO | WO-2015/011455 | A1 | 1/2015 |
| WO | WO-2015/149536 | A1 | 10/2015 |
| WO | WO-2015/149537 | A1 | 10/2015 |
| WO | WO-2016/010355 | A1 | 1/2016 |
| WO | WO-2016/033384 | A1 | 3/2016 |
| WO | WO-2017/147367 | A1 | 8/2017 |
| WO | WO-2018/160797 | A1 | 9/2018 |
| WO | WO-2018/225913 | A1 | 12/2018 |
| WO | WO-2020/117030 | A1 | 6/2020 |
| WO | WO-2021/016457 | A1 | 1/2021 |

(56) References Cited

FOREIGN PATENT DOCUMENTS

| | | | |
|---|---|---|---|
| WO | WO-2022/261494 | A1 | 12/2022 |
| WO | WO-2023/154902 | A1 | 8/2023 |
| WO | WO-2023/215407 | A2 | 11/2023 |
| WO | WO-2024/163973 | A1 | 8/2024 |

OTHER PUBLICATIONS

ALCAINE—proparacaine hydrocholoride solution/drops, Alcon Laboratories, Inc., Dec. 2020 (6 total pages).
Andreoli, C. M., et al., "Open globe injuries: Emergency evaluation and initial management," In: UpToDate, Post TW (Ed), Up To Date, Waltham, MA (Literature review current through Aug. 2021; topic last updated Feb. 2020) (38 total pages), last retrieved from: https://eye.hms.harvard.edu/eyeinsights/2014-april/benchrnark.-protocols-managing-eye-trauma.
Attia, A.A.M. and Hassan, A.M., "Effect of cryotherapy on pain management at the puncture site of arteriovenous fistula among children undergoing hemodialysis," International Journal of Nursing Sciences, vol. 4, pp. 46-51 (available online Dec. 18, 2016).
Belmonte, C., et al., "Sensory Innervation of the Eye", Chapter 16, Adler's Physiology of the Eye (Eleventh Edition), pp. 363-384, Year: 2011, Elsevier Inc. (with cover pages and TOC, 32 total pages).
Benson, M. T. and Nelson, M.E., "Cyclocryotherapy: a review of cases over a 10-year period," British Journal of Ophthalmology, Year: 1990, vol. 74, pp. 103-105 (3 total pages).
Besirli, Cagri G., et al., "Randomized Safety and Feasibility Trial of Ultra-Rapid Cooling Anesthesia for Intravitreal Injections," Ophthalmol. Retina., Apr. 15, 2020; S2468-6530, vol. 20, No. 30142-1, doi: 10.1016/j.oret.2020.04.001 (Abstract only—2 total pages).
Bras, Alvaro, "Safety Alert: Risks associated with Ophthalmic Anesthetics," reviewed by Dr. S. Brodovsky, MD, FRCSC, WRHA Pharmacy Program, Sep. 2016 (4 total pages) last retrieved Jul. 23, 2025 from https://web.archive.org/web/20160909071428/https:/mpha.in1touch.org/uploaded/web/Legislation/Practice%20Resources/OPHTHALMIC%20TOPICAL%20ANESTHETICS%20AND%20SIDE%20EFFECTS%20REVIEW.pdf.
Cataldi, J.K., et al., "Cryotherapy Effects, Part 2: Time to Numbness Onset and Numbness Duration," International Journal of Athletic Therapy & Training, vol. 18, No. 5, pp. 26-28 (Sep. 2013).
Chao, Daniel L., et al., "A Novel Rapid Cooling Device for Intravitreal Injection Anesthesia: Results of the Prospective COOL-2 Study", Investigative Ophthalmology & Visual Science, vol. 61, No. 4196, ARVO Annual Meeting Abstract, Jun. 2020 (2 total pages).
Chee, C. K. L. and Scott, J.D., "Cyclocryotherapy for chronic glaucoma after vitreoretinal surgery," Eye, vol. 8, pp. 414-418, Year: 1994 (5 total pages).
Fraunfelder, F., "Liquid Nitrogen Cryotherapy for Surface Eye Disease (An AOS Thesis)," Transactions of the American Ophthalmological Society, vol. 106, pp. 301-324, Dec. 2008 (46 total pages), PMCID: PMC2646430, PMID: 19277243.
Heiting, G., "Cornea of the eye—Definition and Detailed Illustration", Page published in Feb. 2019 and updated in Sep. 2021, last retrieved Oct. 1, 2021 from https://www.allaboutvision.com/resources/cornea.htm (7 total pages).
International Search Report and Written Opinion issued Jun. 21, 2024 by U.S. Patent and Trademark Office as International Searching Authority for International Bureau of WIPO in International Patent Application No. PCT/US2024/014354 (12 total pages).
International Search Report and Written Opinion issued Jul. 8, 2021 by U.S. Patent and Trademark Office as International Searching Authority for International Bureau of WIPO in International Application No. PCT/US2021/024514 (8 total pages).
Kim, Byoung Seon, et al., "Long-term Results from Cyclocryotherapy Applied to the 3O'clock and 9O'clock Positions in Blind Refractory Glaucoma Patients," Korean J. Ophthalmol., vol. 29, No. 1, pp. 47-52, doi 10.3341/kjo.2015.29.1.47, Accepted Apr. 28, 2014 (6 total pages).
Lee, B. S., et al., "Managing dry eye disease and facilitating realistic patient expectations: A review and appraisal of current therapies," Clinical Ophthalmology, 14, pp. 119-126, Year: 2020, doi: 10.2147/OPTH.S228838 (8 total pages).
Levitt, A E., et al., "Chronic dry eye symptoms after LASIK: parallels and lessons to be learned from other persistent post-operative pain disorders," Molecular Pain,, vol. 11, No. 21, doi 10.1186/s12990-015-0020-7, Year: 2015 (12 total pages).
Lindsell, L. B., et al., "Use of Topical Ice for Local Anesthesia for Intravitreal Injections," JAMA Ophthalmology, Aug. 2014, vol. 132, No. 8, pp. 1010-1011 (2 total pages).
Mcmonnies, C. W., "The potential role of neuropathic mechanisms in dry eye syndromes," Journal of Optometry, vol. 10, pp. 5-13, (available online Jul. 16, 2016) doi: <http://dx.doi.org/10.1016/j.optom.2016.06.002> (9 total pages).
Morkin, M.I. and Hamrah, P., "Efficacy of Self-Retained Cryopreserved Amniotic Membrane for Treatment of Neuropathic Corneal Pain," The Ocular Surface, vol. 16, Issue 1, pp. 132-138, Jan. 2018, Author Manuscript available in PMC Jan. 1, 2019 (16 total pages).
No Author, "NDA 208135: Tetracaine hydrochloride ophthalmic solution 0.5% Steri-Unit", U.S. Food and Drug Administration—Center for Drug Evaluation and Research: Division Director Summary Review for Regulatory Action for Application, Version date: Jul. 29, 2015 (Reference ID 3894523) (26 total pages).
Office Action issued by China National Intellectual Property Administration on May 29, 2025 in Chinese Patent Application No. 202180024320.9 with partial English translation (15 total pages).
Olson, J. and Stravino, V., "A Review of Cryotherapy," Physical Therapy, vol. 52, No. 8, pp. 840-853 (Aug. 1972).
Pathak, A. K., et al., "Pain reduction after photoablation," EyeWiki by the American Academy of Ophthalmology, https://eyewiki.org/w/index.php ?title= Pain_ Reduction_After _Photoablation&oldid=727 68, web page last updated on Sep. 19, 2021 (2 total pages).
No Author, "Cooling Anesthesia for Intravitreal Injection (COOL-1)," ClinicalTrials.gov Identifier: NCT03732287, Sponsors, Collaborators, and Responsible Party: Recens Medical, Inc., First Posted Nov. 6, 2018 (7 total pages).
Reitberger, H.H., et al., "Argon cold plasma—a novel tool to treat therapy-resistant corneal infections," American Journal of Ophthalmology, doi: 10.1016/j.ajo.2018.03.025, Accepted Date: Mar. 14, 2018, Author Manuscript—27 total pages.
Shah, Anjali, "Cryoanesthesia for Intravitreal Injections," Clinical Trial ID: NCT02872012: Protocol Version 4.0, Oct. 11, 2017, last retrieved Aug. 20, 2025 from: https://cdn.clinicaltrials.gov/large-docs/12/NCT02872012/Prot_000.pdf (15 total pages).
Shetty, R., et al., "Cold bandage contact lens use reduces post-photorefractive keratectomy or corneal collagen-crosslinking pain perception in patients," Indian Journal of Ophthalmology, vol. 71, No. 5, pp. 1855-1861 (20 total pages), May 2023.
Shetty, R., et al., "Pain management after photorefractive keratectomy," Journal of Cataract & Refractive Surgery, vol. 45, Issue 7, pp. 972-976, Jul. 2019, https://doi: 10.1016/j.jcrs2019.01.032 (5 total pages).
Sowka, J. and Kabat, A.G., "Just an Eyedrop? Think Again," Review of Optometry, vol. 143:03, Issue: Mar. 15, 2006, published May 3, 2006 (3 total pages).
Spierer, O., et al. "Corneal mechanical thresholds negatively associate with dry eye and ocular pain symptoms," Investigative Ophthalmology & Visual Science, vol. 57, pp. 617-625, Accepted: Dec. 30, 2015, , DOI: 10.1167/iovs.15-18133 (9 total pages).
Sridhar, M. S., "Anatomy of cornea and ocular surface.," Indian Journal of Ophthalmology, vol. 66, No. 2, pp. 190-194, Feb. 2018, doi: 10.4103/ijo.IJO _ 646 _ 17 (13 total pages).
Video: Dr. Najeeb Lectures, "Ciliary Ganglion—Gross Anatomy," last retrieved on Oct. 1, 2021 from https://www.youtube.com/watch?v=6kH6Fg7ES6E, posted Jun. 6, 2014 (7 total pages).
Video: Soton Brain Hub, "The Ciliary Ganglion," last retrieved on Oct. 1, 2021 from https://www.youtube.com/watch?v=kQiP-zuNEHA, posted Aug. 8, 2015 (3 total pages).
Zarei-Ghanavati, S., et al., "Efficacy of corneal cooling on postoperative pain management after photorefractive keratectomy: A contralateral eye randomized clinical trial," Journal of Current

(56) References Cited

OTHER PUBLICATIONS

Ophthalmology, vol. 29, pp. 264-269, Available online May 11, 2017, doi: 10.1016/j.joco.2017.04.004 (6 total pages).
Office Action issued Sep. 5, 2025 by China National Intellectual Property Administration in Chinese Patent Application No. 202180024320.9 with partial English translation (17 total pages).
Final Office Action issued Jul. 29, 2025 by U.S. Patent and Trademark Office in U.S. Appl. No. 18/948,163 (11 total pages).

* cited by examiner

| ICE PERCENTAGE CALCULATIONS | | |
|---|---|---|
| Mixture: | Value | Units |
| Volume normal saline | 80 | mL |
| Volume Glycerol | 20 | mL |
| Temperature setpoint | -10 | ˚C |
| Mass H20 | 79.6 | g |
| Mass NaCl | 0.72 | g |
| % Glycerol | 20% | L/L solution |
| Mass Glycerol | 25.2 | g |
| Ice percentage | 30% | ice by mass |

FIG. 2

Control, n=3
(example: #44)

ECT-4143
treated, n=3
(Example #47)

FORMULATIONS, DEVICES, AND METHODS FOR ALLEVIATING SYMPTOMS OF OCULAR SURFACE DISCOMFORT

This application is a continuation of International Application No. PCT/US2024/014354 filed on Feb. 2, 2024, which claims the benefit of U.S. Provisional Application No. 63/443,082 filed on Feb. 3, 2023, the disclosures of each of which are hereby incorporated by reference in their entireties.

This application claims priority under 35 U.S.C. § 119(c) to U.S. Ser. No. 63/443,082, filed Feb. 3, 2023, the contents of which are hereby incorporated by reference in its entirety.

TECHNICAL FIELD

The present invention relates generally to apparatuses, systems, and methods for creating and administering a biomaterial such as a cold slurry. More particularly, the present invention relates to apparatuses, systems and methods for treating ocular surface discomfort by causing a subject's ocular surface temperature to decrease to a temperature that is low enough and for a time period that is sufficient to cause ocular hypesthesia, or a reduction in ocular sensation, in a safe and effective manner.

BACKGROUND

The cornea of the eye is a transparent, avascular tissue that measures approximately 11-12 mm horizontally and 9-11 mm vertically. Sridhar, M. S., Anatomy of cornea and ocular surface. *Indian Journal of Ophthalmology,* 66(2), 190-194 (February 2018). It is located on the outermost surface of the eye, positioned in front of the pupil and iris, in order to refract light as it enters.

Innervation to the cornea begins at the brain stem, where a large sensory root branches off the pons and attaches to the trigeminal nucleus caudalis—located at the lateral portion of the medulla. From there, the trigeminal nerve branches off into three divisions, one of which is the ophthalmic division. This root divides into three more branches, with one extension, called the nasociliary nerve. This purely sensory nerve travels along the superior portion of the orbital cavity and contributes smaller branches to the cornea. The two types of divisions from this nerve are called short ciliary nerves and long ciliary nerves. The short ciliary nerves pass through a sensory root, into the ciliary ganglion, then exit that nucleus to pierce the sclera and enter the peri-choroidal space, where they can move into the cornea. Belmonte, C., Tervo, T. T., & Gallar, J. (2011), CHAPTER 16—Sensory Innervation of the Eye, *Adler's Physiology of the Eye* (Eleventh Edition, pp. 363-384), Elsevier Inc.

The peri-choroidal space is located between the sclera, the outermost layer of the eyeball, and the choroid, the heavily vasculated layer that is responsible for providing nutrients to the structures of the eye. There are about 8-10 short ciliary nerves that puncture the sclera, but these nerves branch into about 15-20 divisions once inside the peri-choroidal space. In regard to the long ciliary nerves, there are over 50 branches that pierce the sclera and divide again inside the peri-choroidal space. At the limbus, the junction between the sclera and cornea, the nerves lose their myelin sheath and continue as free nerve endings. The nerves collect sensory signals from the cornea and send them backwards, towards the brain stem. Belmonte, C., Tervo, T. T., & Gallar, J. (2011). CHAPTER 16—Sensory Innervation of the Eye, *Adler's Physiology of the Eye* (Eleventh Edition, pp. 363-

384), Elsevier Inc. Not all the details of corneal innervation are entirely well-understood and may vary somewhat patient to patient. There may be some contribution from other nerve fibers or some normal anatomical variations in the routes of innervation.

The free nerve endings are located under the corneal epithelium, the anterior layer protecting the corneal structure, and often contribute to painful ocular sensations. When patients are bothered by these symptoms, the condition is termed dry eye syndrome ("DES"), also known as ocular surface disease ("OSD"). Causes of this condition are multifactorial. One important cause is inadequate amounts of aqueous tear production, causing the eye to lack hydration and lubrication. Other causes of ocular surface disease can include meibomian gland dysfunction or damage to the corneal epithelium.

These "dry eye-induced alterations to the properties of corneal afferent neurons and the central processing of corneal input may have significant consequences for both the regulation of tearing and ocular pain." Mcmonnies, C. W., The potential role of neuropathic mechanisms in dry eye syndromes, *Journal of Optometry,* 10, 5-13 (2017). Importantly, some patients continue to have ocular surface pain even though their ocular surface returns to a clinically normal appearance. This situation presents a clinical challenge because the cause is thought to be somatosensory dysfunction of the corneal innervation that persists long after the original insult that excited the nerves.

Other sources of corneal discomfort can include postoperative pain, potentially after photorefractive keratectomy, which is a procedure used to treat refractive error that requires removal of the corneal epithelium before applying excimer laser ablation. Other surgical procedures can also lead to corneal discomfort, including procedures that do not necessarily involve removal of the epithelium, but where the epithelium undergoes a mild to moderate desiccation during the procedure. A patient can also experience ocular discomfort following ocular trauma (e.g., corneal abrasions) and laser in-situ keratomileusis (LASIK) surgery. Other treatments can also cause corneal discomfort, like injections for treating macular degeneration and other treatments for different ocular structures.

There are three different types of nociceptive receptors innervating the cornea. Twenty percent of corneal nociceptors are Aδ mechanoreceptors, which are responsible for fast-conducting sharp, painful stimuli, caused by aggravation to the ocular surface. Seventy percent of corneal nociceptors are polymodal, which are stimulated by corneal nerve damage and cause neuropathic pain and "reflexive tearing." Levitt, A. E., et al., Chronic dry eye symptoms after LASIK: parallels and lessons to be learned from other persistent postoperative pain disorders, Molecular Pain, 11:21 (2015). The last ten percent of corneal nociceptors are C-fiber cold receptors, which play a crucial role in maintaining basal tear secretion. These receptors are highly sensitive to temperature change within corneal tissue, and LASIK surgery can cause evaporation of tears on the tear film surface, lowering the temperature by about 0.3 degrees per second, thus influencing C-fiber signals. (Levitt et al., 2015).

Many mechanisms, including dryness, prior surgery, dysfunction of the eyelid glands, or prior chemical irritation, may lead to the clinical syndrome of OSD, notable for signs of ocular irritation and symptoms characterized as dryness, burning, or discomfort. Even after the initial insult for the mechanism has resolved, i.e., normal lubrication of the eye has been restored, patients may still report significant symptoms of ocular surface discomfort, despite their ocular surface having only minimal signs of disease, suggesting a component of hypersensitization or allodynia. Indeed, literature references note "the status of the ocular surface alone is not sufficient to understand dry eye and that corneal somatosensory function . . . must be considered when evaluating a patient with dry eye." Spierer O, Felix E R, McClellan A L, et al. Corneal mechanical thresholds negatively associate with dry eye and ocular pain symptoms, *Invest Ophthalmol Vis Sci.,* 57:617-625 (2016). This situation presents a quandary for the treating physician—the patient has residual pain and discomfort with a normal appearing ocular surface (corneal somatosensory dysfunction). Additional lubrication and other therapies targeted to improve the ocular surface are, as expected, no longer of any help to these patients.

Current treatment methods for ocular pain, including that associated with dry eye syndrome/ocular surface disease, PRK, or LASIK surgery, or corneal somatosensory dysfunction are either limited, of transient value, or associated with negative side effects. Dry eye syndrome is most commonly treated with warm compresses, over-the-counter artificial tears, or prescription eye drops targeting improved tear production or reducing inflammation. Physicians may also recommend topical ocular lubricants, hygiene products that clear debris from underneath the eyelids. These methods work by softening meibum, the oily, lipid-rich secretion from meibomian glands, in order to help spread tear production over the cornea. The limitation to these therapies is the short-term relief and need for continuous application. Lubricants or artificial tears may soothe irritation, but do not actually address the cause of dry eye and may also contribute to increased debris collecting under the eyelid. Shen Lee, B., et al., Managing dry eye disease and facilitating realistic patient expectations: A review and appraisal of current therapies, *Clinical Ophthalmology,* 14 119-126 (January 2020).

Regarding postoperative pain management for photorefractive keratectomy and LASIK eye surgery, topical NSAIDs and soft bandage contact lenses are the most common treatment. NSAID medications prevent the production of prostaglandin, a hormone-like substance involved in inflammation, that occurs with corneal tissue damage. Pathak, A. K., & Karacal, H., (2019), Pain reduction after photoablation, *EyeWiki by the American Academy of Ophthalmology*. Topical NSAIDs carry a risk of corneal damage, such as erosions, defects, delayed corneal epithelial healing, or corneal melting (which can lead to vision loss). With soft bandage contact lenses, this method can stimulate the regrowth of epithelial cells, and act as a delivery system for antibiotics or topical NSAIDs. However, bandage contact lenses can promote bacterial growth and are often not be efficient in relieving pain. Shetty, R., et al., Pain management after photorefractive keratectomy, Journal of Cataract Refract Surgery, 45(7):972-976 (2019).

Acute ocular pain can also be treated with topical ophthalmic anesthetic drops, such as Proparacaine Hydrochloride and Tetracaine Hydrochloride. These aqueous solutions are given as short-term treatment for pain, or when measuring intra-ocular pressure, removing foreign bodies, soothing sutures in the cornea, or as a preoperative anesthetic for ophthalmic surgery. Topical anesthetics can block corneal nerves from sending painful stimuli for about 15-20 minutes per dose. With this short-term pain relief, patients require continuous application, but chronic use can eventually lead to corneal toxicity. Toxic effects on the cornea include damaging stromal keratocytes, which are cells that play a significant role in healing trauma to the cornea. If epithelial cells cannot migrate across the cornea, the epithelium will eventually start to slough off and lead to chronic non-healing of corneal epithelium.

Maintaining some perception of pain, however, is critical to the normal function of the healthy cornea. Neuropathic keratopathy, also known as neurotrophic keratitis, is a syndrome where due to a pathological lack of sensation of the corneal and conjunctiva, the ocular surface experiences a syndrome that progresses from tear film abnormalities, to epitheliopathy, to eventual stromal lysis. For true neuropathic keratopathy, an eye must have a lack of sensation of the cornea and conjunctiva due to pathological destruction to the trigeminal nerve, which can occur from surgery intended to treat trigeminal neuralgias, surgery of acoustic neuromata, or from infections such as herpes zoster ophthalmicus or leprosy. Other forms of neuropathic keratopathy occur from the misuse of topical anesthetics. In rabbit models, typical trophic changes in the corneal epithelium have been shown after controlled thermocoagulation of the trigeminal ganglion in rabbits. This denervation was found to markedly affect the proliferative activity of the epithelium, and mitosis was sparse.

As explained above, the cornea is exquisitely sensitive to pain or perturbation. There are a host of human clinical conditions that cause mild to severe corneal pain and discomfort, all of which could potentially be addressed by the development of a safe and efficacious treatment for corneal pain. The current state of topical numbing drops only numb the cornea for a matter of minutes and chronic use is associated with severe morbidities including corneal infections and corneal melting. Further, traditional approaches for treating ocular pain result in complete anesthesia of sensation to the eye, which can be very problematic in the chronic context due to the risk of development of neuropathic keratopathy. Furthermore, in eyes that are chronically inflamed and painful, a corneal somatosensory dysfunction becomes the predominant feature of the pain syndrome. In summary, there are many patients with debilitating ocular surface discomfort that can be associated with active corneal pathology or can persist long after the original injury with no detectable ongoing pathology. Clearly there is a large unmet clinical need for development of a longer-acting safe corneal anesthetic therapy that partially blocks corneal sensation and significantly decreases patient discomfort.

SUMMARY

The following embodiments recite non-limiting permutations of combinations of features of the inventions described. Other permutations of combinations of features are also contemplated and/or described throughout the disclosure. In particular, each of these numbered embodiments is contemplated as depending from or relating to every previous or subsequent numbered embodiment, independent of the listed order.

In certain aspects, the present disclosure provides a cold slurry formulation for alleviating symptoms of ocular surface discomfort, the cold slurry formulation comprising: water; and a freezing point depressant, wherein the cold slurry formulation is configured to be directly or indirectly applied to a target ocular surface to cause a numbing of the target ocular surface, and wherein an ocular sensation of the eye is restored following the application of the cold slurry to the target ocular surface. In certain embodiments, the cold slurry formulation further comprises a lipid. In certain embodiments, the formulation comprises a freezing point depressant, wherein the freezing point depressant is at a concentration of about 10%-40% (v/v). In certain embodiments, the formulation comprises a lipid, wherein the lipid is at a concentration of about 0.1%-10%, 10%-20%, 20%-30%, or 30%-45% (v/v). In further embodiments, the formulation comprise a freezing point depressant, wherein the freezing point depressant is at a concentration of about 10%-20%, 20%-30%, or 30%-40% (v/v). In certain embodiments, the formulation comprises a lipid, wherein the lipid is at a concentration of about 15%-45% (v/v). In certain embodiments, the formulation comprises a freezing point depressant, wherein the freezing point depressant is at a concentration of about 10%-25% (v/v). In certain embodiments, the slurry is injectable through a needle. In other embodiments, the slurry is not injectable through a needle. In certain embodiments, the slurry has a percentage of solid ice of between about 0.1% and about 75% of the slurry by weight. In certain embodiments, the slurry has a percentage of solid ice of between about 0.1% and 1%, between about 1% and 10%, between about 10% and about 20%, between about 20% and about 30%, between about 30% and about 40%, between about 40% and about 50%, between about 50% and about 60%, between about 60% and about 70%, and greater than about 50%. In certain embodiments, the slurry has a percentage of solid ice particles that constitutes between about 0.1% and about 50% of the slurry by weight.

In certain aspects, the present disclosure provides a method of alleviating symptoms of ocular surface discomfort, the method comprising: applying a cold slurry formulation on a surface of an eye of a patient adjacent to a corneal limbus, wherein the cold slurry formulation comprises water, and a freezing point depressant, wherein the application of the cold slurry formulation is configured to cause a degree of numbing of a cornea of the eye for a period of time, and, after that period of time, an ocular sensation of the eye is restored. In certain embodiments, the cold slurry formulation further comprises a lipid. In further embodiments, methods are provided wherein a cold slurry formulation is applied posterior to a corneal limbus. In further embodiments, methods are provided wherein the cold slurry remains on the surface of the eye for more than about 4 hours without applying the cold slurry formulation an additional time on any day following the first day of application. In certain embodiments, methods are provided wherein the cold slurry formulation comprises a freezing point depressant, wherein the freezing point depressant is glycerol. In further embodiments, methods are provided wherein the cold slurry formulation comprises a lipid, wherein the lipid comprises soy-Phosphatidylcholine (soy-PC). In further embodiments, methods are provided wherein the cold slurry formulation comprises a lipid, wherein the lipid comprises fatty acids selected from a group consisting of stearic acid, palmitic acid, lauric acid, and myristic acid, and a combination thereof. In further embodiments, methods are provided wherein the cold slurry formulation comprises a hyaluronic acid. In certain embodiments, methods are provided wherein the cold slurry formulation comprises an excipient. In certain embodiments, methods are provided wherein the cold slurry formulation comprises an excipient, wherein the excipient is a poloxamer. In further embodiments, methods are provided wherein the ocular sensation of the eye is restored about 21 days following the application of the cold slurry formulation. In further embodiments, methods are provided wherein the ocular sensation of the eye is restored about between about 7 days and about 90 days following the application of the cold slurry formulation. In further embodiments, methods are provided wherein a sclera of the eye of the patient is cooled to a temperature of between about −6° C. and about 4° C. during the application of the cold slurry. In further embodiments, methods are provided wherein the cold slurry is applied for between about 2 minutes and about 15 minutes. In further embodiments, methods are provided wherein an additional amount of the cold slurry is re-applied at about 90 seconds after the first application of cold slurry. In further embodiments, methods are provided wherein the administration of the cold slurry formulation is topical application. In further embodiments, methods are provided wherein the administration of the cold slurry formulation is via injection.

In certain aspects, a device for protecting a cornea on an ocular surface from negative effects of the cooling treatment is provided, the device comprising: a structure that is configured to adhere to the ocular surface through the formation of a vacuum, the structure comprising: an enclosing wall having an inner surface, an outer surface, and an opening surface, the enclosing wall extending from a first end to a second end and the inner surface forming an internal cavity, wherein the opening surface is configured to contact and encircle the perimeter of the cornea and the vacuum is formed within the internal cavity when the structure is activated. In certain embodiments, the adhering of the structure to the ocular surface substantially seals the cornea within the opening surface of the enclosing wall. In certain embodiments, the structure comprises a suction cup to ensure it is properly aligned on the eye and remains in place. In certain embodiments, the enclosing wall comprises a nonporous material having low thermal conductivity, selected from the group consisting of polymers, polyvinyl chloride (PVC), neoprene, polyethylene (PE), polytetrafluorethylene (PTFE), and combinations thereof. In certain embodiments, the enclosing wall comprises a thermally insulating material selected from the group consisting of polyurethane (PU) foam, polyisocyanurate foam, extruded polystyrene foam (XPS), expanded polystyrene foam (EPS), aerogel, and combinations thereof. In certain embodiments, the enclosing wall comprises an optically transparent or semi-transparent material. In certain embodiments, the enclosing wall comprises an optically opaque material. In certain embodiments, the structure is activated by constricting the internal cavity and then releasing the constriction of the internal cavity. In certain embodiments, the structure is activated by squeezing the enclosing wall and then releasing the enclosing wall. In certain embodiments, the vacuum is a partial vacuum.

In certain embodiments, a method for protecting a cornea on a surface of an eye of a subject is provided, the method comprising: a) positioning a cornea-protecting device comprising an internal cavity over the cornea of the subject; b) constricting and releasing a portion of the cornea protecting device to form a vacuum within the internal cavity; and c) adhering the cornea-protecting device to the surface of the eye; wherein the cornea-protecting device comprises an enclosing wall having an inner surface, an outer surface, and an opening surface, the enclosing wall extending from a first end to a second end, wherein the inner surface forms the internal cavity. In certain embodiments, the method further comprises administering a cold slurry formulation to the surface of the eye after the cornea-protective device has been placed. In further embodiments, the cornea-protecting device is configured to protect the cornea physically and thermally from the cold slurry formulation. In certain embodiments, the formation of the vacuum within the internal cavity of the cornea-protecting device comprises squeezing the cornea-protecting device. In certain embodiments, the vacuum is a partial vacuum.

In certain aspects, the present disclosure provides a device for protecting an eyelid of a subject, the device comprising: a first surface that is configured to contact an upper eyelid; and a second surface that is configured to contact a lower eyelid, wherein the first surface and the second surface are configured to reversibly attach with each other so as to create an opening between the first surface and the second surface, and wherein when inserted on top of an eye, the device prevents the upper eyelid and the lower eyelid from closing and protects the eyelids by physically and thermally separating the eyelids from an ocular surface or a material deposited on the ocular surface. In certain embodiments, the device further comprises a channel in one or more of the first surface and the second surface, wherein the channel is configured to allow fluid to escape from the ocular surface when the device is inserted on top of the eye. In certain embodiments, the device further comprises a platform on one or more of the first surface and the second surface configured to facilitate handling and manipulation of the device. In further embodiments, the first surface comprises a first end and a second end, the second surface comprises a first end and a second end, wherein the first end of the first surface is attached to the first end of the second surface, and the second end of the first surface is attached to the second end of the second surface. In certain embodiments, the first surface and the second surface are curved in shape. In further embodiments, one or more of the first surface and the second surface is an arc. In certain embodiments, the first surface and the second surface are adjustable in size. In certain embodiments, the first surface and the second surface are adjustable relative to each other to adjust the size of the opening. In certain embodiments, the first surface and the second surface are separate components of the device that can be assembled to form the device. In certain embodiments, one or more of the first surface and the second surface comprises segments of curvilinear links that can be articulated relative to each other to adjust the size of the opening. In certain embodiments, one or more distances across the opening between the first surface and the second surface can be adjusted to accommodate the eyelid and the eye of various shapes and sizes. In certain embodiments, the device comprises one or more types of plastic. In certain embodiments, the device comprises one or more porous materials. In further embodiments, the one or more porous materials comprises a thermally insulating material selected from the group consisting of polyurethane (PU) foam, polyisocyanurate foam, extruded polystyrene foam (XPS), expanded polystyrene foam (EPS), aerogel, and combinations thereof. In further embodiments, one or more of the first surface and the second surface comprises a thermal insulating material and a wicking material. In further embodiments, the wicking material selected from the group consisting of PVA, open cell foam materials, and a combination thereof. In certain embodiments, the device further comprises a receiving structure configured to receive a cornea-protecting device. In further embodiments, the cornea-protecting device comprises: a structure that is configured to adhere to the ocular surface through the formation of a vacuum, the structure comprising: an enclosing wall having an inner surface, an outer surface, and an opening surface, the enclosing wall extending from a first end to a second end, wherein the inner surface forms an internal cavity, wherein the opening surface is configured to contact and encircle the perimeter of the cornea and the vacuum is formed within the internal cavity when the structure is activated. In further embodiments, the receiving structure is situated in the opening of the device such that the receiving structure is placed substantially over the cornea when the device is inserted on top of an eye. In further embodiments, the receiving structure comprises a substantially circular shape, and is attached to the first surface and the second surface. In certain embodiments, the device is configured to protect both the eyelid and the cornea. In certain embodiments, the device further comprises one or more structures configured to serve as a speculum to keep the eyelid open while the device is inserted into the eye.

In certain aspects, a method for protecting an upper and a lower eyelid of a subject is provided, the method comprising: inserting an eyelid-protecting device on top of an eye of the subject; contacting a first surface of the eyelid-protecting device around a contour of an upper eyelid; contacting a second surface of the eyelid-protecting device around a contour of a lower eyelid; wherein the first surface and the second surface are configured to attach with each other so as to create an opening between the first surface and the second surface, and wherein when inserted on top of the eye, the device prevents the upper eyelid and the lower eyelid from closing and protects the eyelids by physically and thermally separating the eyelids from an ocular surface or a material deposited on the ocular surface. In certain embodiments, the method further comprises administering a cold slurry formulation to the ocular surface. In further embodiments, the cold slurry formulation comprises water, a freezing point depressant, and, optionally, a lipid.

In certain aspects, a kit is provided, the kit comprising: one or more syringes comprising a cold slurry formulation; and a packaging enclosing the multiple syringes, wherein the packaging is configured to store, seal, and provide thermal and moisture protection for the one or more syringes. In certain embodiments, the kit comprises at least two syringes comprising the cold slurry formulation. In certain embodiments, the kit comprises from 2-20, from 2-15, from 2-10, or from 2-5 syringes. In further embodiments, one or more of the syringes comprising the cold slurry formulation contains about 1-20 ml of the cold slurry formulation. In certain embodiments, the packaging comprises a phase change material, thermal insulation, reflective barrier, or a combination thereof. In further embodiments, the packaging is configured to protect the one or more syringes against contamination, temperature changes, environmental exposure, or a combination thereof. In certain embodiments, the cold slurry formulation comprises water, a freezing point depressant, and, optionally, a lipid.

In certain aspects, a kit is provided, the kit comprising: one or more syringes; a first packaging enclosing the one or more syringes; a container comprising a cold slurry formulation; and a second packaging enclosing the one or more syringes and the container, wherein the second packaging is configured to store, seal, and provides thermal and moisture protection for the one or more syringes and the container. In certain embodiments, the cold slurry formulation comprises water, a freezing point depressant, and, optionally, a lipid.

In certain aspects, a self-contained cooling device for cooling a target tissue surface, such as an ocular surface, is provided, the self-contained cooling device comprising: a formulation chamber comprising a hollow chamber with an open end and a closed end, wherein the formulation chamber is configured to receive and hold a cold slurry formulation or other formulation that can maintain below 0° C. temperatures; a removable lid configured to fit over and seal the open end of the formulation chamber; and a target surface interface comprising a first surface and a second surface, wherein the first surface is configured to contact the target tissue surface and the second surface is configured to form or contact the closed end of the formulation chamber. In certain embodiments, the self-contained cooling device further comprises a movable plate disposed within the formulation chamber, wherein, when the movable plate is advanced within the formulation chamber toward the closed end of the formulation chamber, a liquid phase of the cold slurry formulation is displaced away from the closed end of the formulation chamber and replaced with a substantially non-liquid phase of the cold slurry formulation, and wherein the movable plate is disposed within the formulation chamber and has a size smaller than the open end of the formulation chamber. In certain embodiments, the self-contained cooling device further comprises: a force spring having a first end and a second end, wherein the first end is operably connected to the movable plate and the second end is operably connected to the removable lid; and one or more side pins operably connected to the hollow chamber; wherein the one or more side pins, when depressed, is configured to cause the first end of the force spring to extend beyond an original length so as to allow the movable plate to advance within the formulation chamber toward the closed end of the formulation chamber. In certain embodiments, the target surface interface is configured to contact an ocular surface, and the self-contained cooling device is configured to maintain the ocular surface at a temperature suitable for alleviating ocular surface discomfort. In certain embodiments, the formulation chamber is configured to receive the cold slurry formulation according to the present disclosure. In certain embodiments, the target surface interface is structurally integrated with the formulation chamber. In certain embodiments, the target surface interface is configured to contact a sclera of the ocular surface. In certain embodiments, the target surface interface comprises an opening configured to fit over a cornea of the ocular surface to avoid contact of the target surface interface with the cornea when the target surface interface is in contact with the ocular surface. In certain embodiments, the target surface interface is configured to permit thermal energy transfer from the target surface interface to the formulation chamber. In certain embodiments, the target surface interface is configured to promote uniform cooling of the target tissue surface when the formulation chamber is filled the cold slurry formulation. In certain embodiments, the opening in the target surface interface is configured to receive a cornea-protecting device. In certain embodiments, the cornea-protecting device is a cornea-protecting device according to the present disclosure. In certain embodiments, the cornea-protecting device is configured to be disposed within the opening of the ocular surface interface and physically and thermally protect a cornea when the ocular surface interface is in contact with the ocular surface. In further embodiments, the force spring is an extension spring, torsion spring, or a combination thereof. In certain embodiments, the target surface interface comprises thermally conductive materials selected from the group consisting of Al, Cu, stainless steel, metal alloys, and combinations thereof. In certain embodiments, the target surface interface comprises one or more encapsulated phase change materials (PCM), shape-stabilized PCMs, or a combination thereof. In certain embodiments, the first surface of the target surface interface comprises a non-stick coating. In further embodiments, wherein the non-stick coating is PTFE. In certain embodiments, wherein the first surface of the target surface interface comprises a hydrophobic coating. In certain embodiments, the first surface of the target surface interface comprises a surface coating that protects the target tissue from adhering to the target surface interface. In certain embodiments, the first surface of the target surface interface comprises a geometric design feature that protects the target tissue from adhering to the target surface interface. In further embodiments, the geometric design feature comprises one or more of a hierarchical microstructure, a hierarchical nanostructure, a bioinspired surface pattern, or a combination thereof. In further embodiments, the first surface of the target surface interface comprises a hydrophilic surface coating. In certain embodiments, the first surface of the target surface interface comprises a low surface energy material. In certain embodiments, the target surface interface comprises an embedded thermoelectric Peltier cooler. In certain embodiments, the target surface interface comprises a thin film of a material.

In certain aspects, a method of alleviating symptoms of ocular surface discomfort is provided, the method comprising: positioning a self-contained cooling device over a target ocular surface; wherein the self-contained cooling device comprises: a formulation chamber comprising a hollow chamber with an open end and a closed end, wherein the formulation chamber is configured to receive and hold a cold slurry formulation; a removable lid configured to fit over and seal the open end of the formulation chamber; and a target surface interface comprising a first surface and a second surface, wherein the first surface is configured to contact the target ocular surface and the second surface is configured to form or contact the closed end of the formulation chamber. In certain embodiments, the cold slurry formulation comprises water, a freezing point depressant, and, optionally, a lipid. In certain embodiments, the self-contained cooling device further comprises a movable plate disposed within the formulation chamber, wherein, when the movable plate is advanced within the formulation chamber toward the closed end of the formulation chamber, a liquid phase of the cold slurry formulation is displaced away from the closed end of the formulation chamber and replaced with a substantially non-liquid phase of the cold slurry formulation, and wherein the movable plate is disposed within the formulation chamber and has a size smaller than the open end of the formulation chamber. In certain embodiments, the method further comprises advancing the movable plate of the self-contained cooling device disposed within the formulation chamber toward the closed end of the formulation chamber. In certain embodiments, the self-contained cooling device further comprises: a force spring having a first end and a second end, wherein the first end is operably connected to the movable plate and the second end is operably connected to the removable lid; and one or more side pins operably connected to the hollow chamber; wherein the one or more side pins, when depressed, is configured to cause the first end of the force spring to extend beyond an original length so as to allow the movable plate to advance within the formulation chamber toward the closed end of the formulation chamber. In certain embodiments, the method further comprises depressing one or more side pins of the self-contained device operably connected to the hollow chamber to cause the first end of the force spring to extend beyond an original length so as to cause the movable plate to advance within the formulation chamber toward the closed end of the formulation chamber.

In certain aspects, a self-contained cooling device for cooling a target tissue surface is provided, the self-contained cooling device comprising: a housing; a heat exchanger, wherein the heat exchanger comprises a formulation chamber configured to receive and hold a formulation, wherein the formulation is configured to freeze to a subzero temperature in a cold environment; an aperture, wherein the aperture is configured to allow a clinician to visualize a cornea of a subject; a target surface interface comprising a first surface and a second surface, wherein the first surface is configured to contact the target tissue surface and the second surface is configured to form or contact the formulation chamber. In certain embodiments, the cold environment is a standard freezer. In certain embodiments, the formulation comprises water and a freezing point depressant. In certain embodiments, the freezing point depressant is at a concentration of about 20% (wt/wt). In certain embodiments, wherein the freezing point depressant is glycerol. In certain embodiments, the first surface is configured to adhere to the target tissue surface upon contact. In certain embodiments, the target surface comprises a sclera. In further embodiments, the sclera is adjacent a corneal limbus. In certain embodiments, the subzero temperature is between about −20° C. and about 0° C. In certain embodiments, the target surface interface comprises copper.

In certain aspects, the self-contained cooling device is configured to receive an accessory. In certain embodiments, the accessory is a speculum. In certain embodiments, the accessory is configured to hold open an eye of a subject during a procedure. In certain embodiments, the accessory is configured to protect an eyelid of a subject from subzero temperatures during a procedure. In certain embodiments, the accessory comprises silicone. In certain embodiments, the accessory comprises thermoplastic elastomer (TPU) or thermoplastic polyurethane (TPE).

In certain aspects, the self-contained cooling device is further configured to receive a cap, wherein the cap is configured to prevent condensation from forming on the target surface interface prior to a procedure.

In certain aspects, a method of alleviating symptoms of ocular surface discomfort is provided, the method comprising: positioning a self-contained cooling device over a target ocular surface; wherein the self-contained cooling device comprises: a housing; a heat exchanger, wherein the heat exchanger comprises a formulation chamber configured to receive and hold a formulation, wherein the formulation is configured to freeze to a subzero temperature in a standard freezer; an aperture, wherein the aperture is configured to allow a clinician to visualize a cornea of a subject; a target surface interface comprising a first surface and a second surface, wherein the first surface is configured to contact the target tissue surface and the second surface is configured to form or contact the formulation chamber. In certain embodiments, the subzero temperature is between about −20° C. and about 0° C. In certain aspects, the formulation comprises water and a freezing point depressant. In certain embodiments, the freezing point depressant is glycerol. In certain embodiments, the treatment time is between about 2 minutes and about 10 minutes.

In certain aspects, the self-contained cooling device is configured to receive an accessory, and wherein the accessory is configured to be positioned adjacent the target ocular surface and prevent an eye of a subject from closing. In certain embodiments, the accessory is configured to thermally protect one or more eyelids from contacting the contact surface interface. In certain embodiments, the accessory is configured to provide an aperture for visualization of a cornea. In certain embodiments, the accessory is configured to provide ease in positioning of the device. In certain embodiments, the accessory is configured to protect an eyelid of a subject from subzero temperatures during a procedure. In certain embodiments, the target surface comprises a sclera. In certain embodiments, the sclera is adjacent a corneal limbus.

In certain embodiments, the target surface interface comprises copper. In certain embodiments, the target surface interface is configured to adhere to the target surface upon contact. In certain embodiments, the target surface interface is configured not to adhere to the target surface interface upon contact. In certain embodiments, the target surface interface is configured to detach from the target surface following a treatment time.

In certain embodiments, methods provided herein further comprise rinsing the target tissue surface with a liquid formulation prior to removing the target surface interface from the target tissue surface. In certain embodiments, the liquid formulation comprises saline. In certain embodiments, the liquid formulation is warmed prior to use.

BRIEF DESCRIPTION OF THE DRAWINGS

The following figures depict illustrative embodiments of the invention.

FIG. 2 is a table showing the breakdown by volume and weight of components of an exemplary biomaterial that can form an injectable cold slurry.

FIG. 13A is a perspective view of an exemplary cornea protecting device and FIG. 13B shows the placement of an exemplary cornea protecting device on the ocular surface to enclose and seal the perimeter of the cornea.

DETAILED DESCRIPTION

Figure 1:
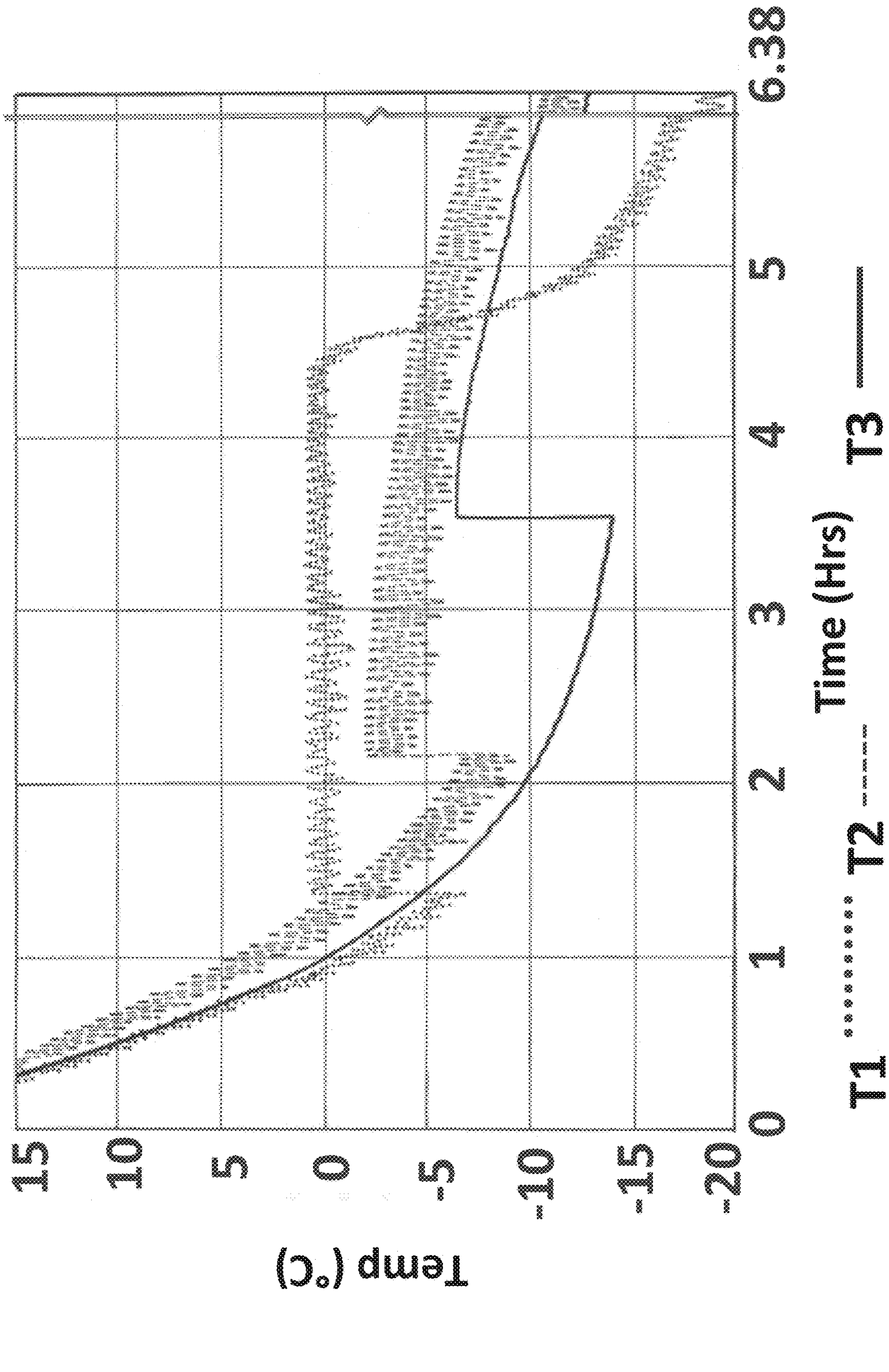
FIG. 1 depicts a freezing point depression graph for liquid water, a solution containing 10% glycerin volume by volume (v/v), and a solution containing 20% glycerin (v/v).

The present disclosure is drawn to apparatuses, devices, systems, and methods of treating ocular surface discomfort with a biological material, such as a cold slurry, or a cooling device. In some embodiments, the biomaterial is a cold slurry (e.g., ice slurry) that can be delivered via topical application directly or indirectly to the surface of the eye or via injection into the eye of a human patient or a subject (e.g., a human who is not a patient or a non-human animal) for prophylactic or therapeutic purposes to reduce ocular discomfort. The systems and methods disclosed herein provide for a hypesthesia (also referred to as hypoesthesia) of the eye that is unexpectedly long-lasting. The hypesthesia may cause a long-lasting corneal numbing followed by a restoration of ocular sensation within days or weeks following application of cold slurry treatment or cooling device, without causing permanent damage to the cornea or disrupting the progress of corneal healing.

The present disclosure provides novel cooling treatments to relieve ocular surface discomfort by applying a cold treatment (e.g., −20° C. to 0° C.) to an eye of a subject for a period of time (e.g., between about 6 minutes and about 10 minutes or between about 2 minutes and about 10 minutes). For example, in certain embodiments, the present disclosures provides a self-contained cooling device and methods for using the same, wherein the self-contained cooling device comprises an ocular (i.e., target) surface interface configured to freeze to a sclera of the eye rapidly upon contact wherein the ocular surface interface adheres to the surface of the eye for the duration of the treatment thereby providing subzero temperatures (e.g., between about −20° C. to about 0° C.) to a precise treatment zone adjacent the corneal limbus. In certain embodiments, the self-contained cooling device lowers the temperature of the sclera to cold temperatures (e.g., −20° C. to about 4° C.) and maintains that low temperature for a period of time that is sufficient to cause ocular surface hypesthesia. This treatment does not cause harmful side effects to the eye, or damage tissue in or around the eye.

In some embodiments, the cold slurry can be applied topically directly or indirectly to the surface of the eye to achieve a desired therapeutic effect such as amelioration or treatment of ocular surface discomfort through long-term corneal numbing. In some embodiments, the therapeutically effective cold slurry is comprised entirely of water and excipient materials (i.e., materials without an active pharmaceutical compound). In other embodiments, the cold slurry further comprises a known active pharmaceutical compound. In some embodiments, a layer of protection, like a contact lens or a cornea-protecting device that covers the cornea and provides a protective barrier around the perimeter of the cornea, is applied to the cornea prior to topical application of the slurry. In some embodiments, the eyelid is protected from topical application of the slurry by using an eyelid-protecting device, for example by inserting a plastic, or other non-thermally conductive material, and/or speculum into a subject's eye.

In some embodiments the length of time that the slurry or cooling treatment is applied to a subject's eye can be varied to induce a greater or milder hypesthesia. In some embodiments, the temperature of the slurry or cooling treatment applied directly or indirectly to the surface of the eye or injected into a subject's eye is varied to induce a greater or milder hypesthesia. In some embodiments, the hypesthesia induced after treatment decreases over time to the point where it is not noticeable. In other embodiments, where a subject's eye may be particularly sensitive, a greater hypesthesia is induced to numb more of the nerves in the subject's eye.

In some embodiments, a container (e.g., vial, syringe, self-contained cooling device) containing a biomaterial is received at a clinical point of care. The biomaterial may be received in a crystallized (or partially crystallized) state. In some embodiments, the final product to be administered via topical application or injection to a human patient or a subject (such as a human who is not a patient or a non-human animal) is a cold slurry comprised of sterile ice particles of water and varying amounts of excipients or additives such as freezing point depressants. For example, the percentage of ice particles in the cold slurry can constitute less than about 10% by weight of the slurry, between about 10% by weight and about 20% by weight, between about 20% by weight and about 30% by weight, between about 30% by weight and about 40% by weight, between about 40% by weight and about 60% by weight, more than about 60% by weight, and the like. In some embodiments the sizes of the ice particles will be controlled to allow for flowability of the slurry through a vessel of various sizes (e.g., needle gauge size of between about 7 and about 43) as described in U.S. application Ser. No. 15/505,042 (Publication No. US2017/0274011), which is incorporated herein by reference in its entirety. Further, in certain embodiments other methods may be used to condition the size of the ice particles to allow for flowability of the slurry through a vessel of various sizes. In some embodiments, the majority of ice particles have a diameter that is less than about half of the internal diameter of the lumen or vessel used for application or injection. For example, in certain embodiments ice particles can be about 1.5 mm or less in diameter for use with a 3 mm catheter.

There are a variety of techniques that may be used to prepare a cold slurry. This disclosure is not limited to any particular method or technique. Exemplary cold slurry formulations and methods for preparing the same have been disclosed previously, for example in U.S. Pat. Nos. 11,241,330; 11,564,830; 11,471,401; U.S. patent application Ser. No. 18/358,795 (filed on Jul. 25, 2023, not yet published); International Application No. PCT/US2022/33095 (Publication No. WO/2022/261494); and International Application No. PCT/US2023/62443 (Publication No. WO/2023/154902); which are hereby incorporated by reference in their entireties.

In some embodiments, one or more excipients may be included in the cold slurry. An excipient is any substance, not itself a therapeutic agent, used as a diluent, adjuvant, and/or vehicle for delivery of a therapeutic agent to a subject or patient, and/or a substance added to a composition to improve its handling, stability, and/or storage properties. In certain embodiments, excipients can constitute less than about 10% volume by volume (v/v) of the cold slurry, between about 10% v/v and about 20% v/v of the slurry, between about 20% v/v and about 30% v/v, between about 30% v/v and 40% v/v, and greater than about 40% v/v. Various added excipients can be used to alter the phase change temperature of the cold slurry (e.g., reduce the freezing point), alter the ice percentage of the cold slurry, alter the viscosity of the cold slurry, prevent agglomeration of the ice particles, prevent dendritic ice formation (i.e., crystals with multi-branching "tree-like" formations, such as those seen in snowflakes), keep ice particles separated, increase thermal conductivity of fluid phase, and/or improve the overall prophylactic, therapeutic, or aesthetic efficacy of the cold slurry.

In some embodiments, one or more freezing point depressants can be added as excipients to form cold slurries with freezing points below 0° C. In certain embodiments, depressing the freezing point of the slurry allows it to maintain flowability and remain applicable through vessels of various sizes (e.g., remain injectable) while still containing a desirable and effective percentage of ice particles. Suitable freezing point depressants include, but are not limited to, salts (e.g., sodium chloride, betadex sulfobutyl ether sodium), ions, Lactated Ringer's solution, sugars (e.g., glucose, sorbitol, mannitol, hetastarch, sucrose, (2-Hydroxypropyl)-β-cyclodextrin, or a combination thereof), biocompatible surfactants such as glycerol (also known as glycerin or glycerine), other polyols (e.g., polyvinyl alcohol, polyethylene glycol 300, polyethylene glycol 400, propylene glycol), other sugar alcohols, or urea, and the like. Other exemplary freezing point depressants include, but are not limited to, those disclosed in U.S. application Ser. No. 15/505,042 (Publication No. US2017/0274011) and are incorporated by reference in their entirety herein. In other embodiments, a slurry paste is formed that has the consistency of toothpaste, which may aid in topical application.

The concentrations of freezing point depressants will determine the ice particle percentage of the cold slurry and its flowability and ability to be applied through vessels of different sizes (e.g., its injectability). The degree of freezing point depression can be calculated using the following formula as described in U.S. application Ser. No. 15/505,042 (Publication No. US2017/0274011), which is incorporated herein by reference in its entirety:

$$\Delta T_F = K_F bi$$

wherein $\Delta T_F$ is the freezing point depression (as defined by $T_{F\ (pure\ solvent)} - T_{F\ (solution)}$), $K_F$ is the cryoscopic constant, b is molality, and i is the van't Hoff factor representing the number of ion particles per individual molecule of solute. Other methods of computing freezing point depression can also be used, for example those disclosed in U.S. application Ser. No. 15/505,042 (Publication No. US2017/0274011).

Referring to FIG. 1, a freezing point depression graph is shown for pure water T1, a mixture of water and 10% (v/v) glycerin T2, and a mixture of water and 20% (v/v) glycerin T3. In this graph, all the substances were placed in a freezer having a constant temperature of −20° C. The temperature was measured using a thermometer placed in each substance. The graph shows that a mixture of water and glycerin will have a different freezing point than that of pure water, which means the solution can be cooled to below 0° C. and only be partially crystallized. The graph shows that cooling causes pure water T1 to crystallize at an equilibrium freezing point of 0° C. This is indicated by the period of time where the pure water remains at a temperature of about 0° C., from about 1.3 hours to about 4.4 hours, which begins immediately after pure water T1 passes a supercooling point at about −6° C. Having an equilibrium window of crystallization (i.e., the "flat line" portion of pure water T1 in FIG. 1) is typical for a pure solvent. For the 10% glycerin solution T2, cooling causes the solution to begin crystallizing at an initial freezing point of about −3° C. after about 2.2 hours, and the crystallization continues as the temperature of the solution drops further to about −8° C. after about 6 hours. The initial crystallization occurs immediately after 10% glycerin solution T2 passes a supercooling point at about −8° C. (which can vary from sample to sample, e.g., supercooling point of between about −15° C. and about −3° C.), shown at around 2.2 hours. Having a descending temperature window of crystallization for the 10% glycerin solution T2 is typical for a solution (i.e., impure mixture). Similarly, for the 20% glycerin solution T3, cooling causes the solution to begin crystallizing at an initial freezing point of about −7° C. after about 3.5 hours (following an initial supercooling point which can vary from sample to sample, e.g., between about −25° C. and about −5° C.), and the crystallization continues as the temperature of the solution drops further to about −11° C. after about 6 hours and continues to decline thereafter past 6.5 hours. The initial crystallization occurs immediately after 20% glycerin solution T3 passes a supercooling point at about −14° C., shown at around 3.5 hours. Similar to the trace for 10% glycerin solution T2, the descending temperature window of crystallization for 20% glycerin solution T3 is typical for a solution.

Referring to FIG. 2, this chart shows the components of an exemplary biomaterial that can form a cold slurry. This chart shows that the percentage of ice for an exemplary biomaterial can be calculated for a particular temperature. The exemplary slurry contains 30% ice by mass (weight by weight; w/w) at −10° C. This exemplary slurry has 80 mL of saline (0.9% NaCl) and 20 mL of glycerol (i.e., glycerin). In weight, such a slurry has about 79.6 g of pure water, about 0.72 g of sodium chloride, and about 25.2 g of glycerol (approximately 20% v/v). In other embodiments, the slurry could contain higher or lower percentages of glycerol by adjusting the relative volume of glycerol to saline. For example, other suitable slurries contain about 10% glycerol (v/v), between about 10% and about 20% glycerol, about 30% glycerol, or more than about 30% glycerol. If an active pharmaceutical compound is to be added to the slurry, the concentration of saline can be adjusted accordingly to maintain the desired concentration of excipients such as glycerol. The percentage of ice will vary depending on the composition of the biomaterial.

Figure 3:
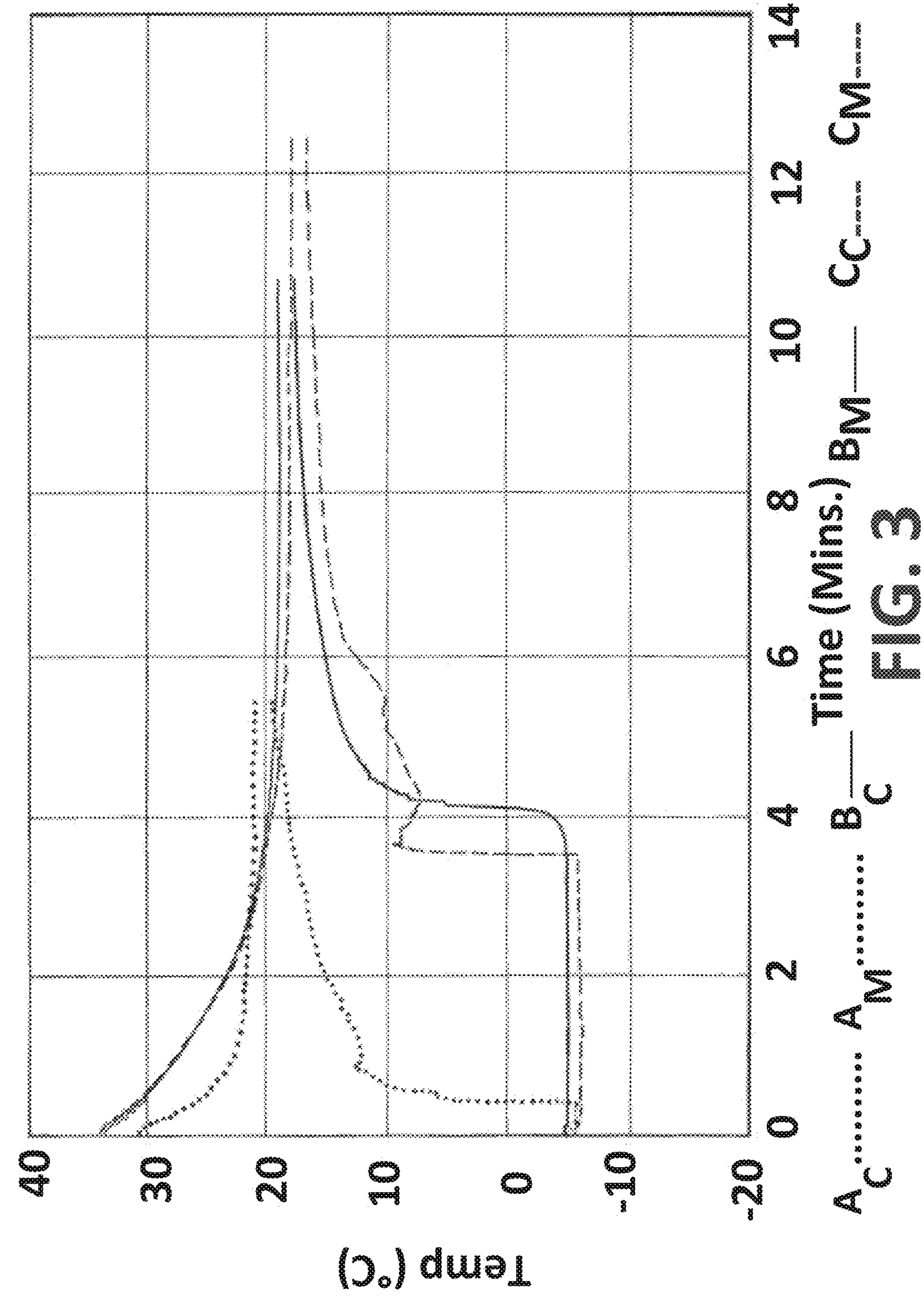
FIG. 3 is a graph showing the characterization of ice content of cold slurries having crystallization set points of −5.5° C. and −8.1° C.

Referring to FIG. 3, different slurry compositions (batches) are characterized with respect to their temperature profiles and ice content. The different slurry batches were placed into a copper plate that is heated to 40° C. and has thermocouple wires that measure changes in temperature of the slurry over time. The plotted data shows temperature change over time for three different slurry batches. The temperatures are measured at two different positions for each slurry: embedded inside of the copper plate (traces $A_C$, $B_C$, and $C_C$) and in the middle of the copper plate exposed to the outside of the plate (traces $A_M$, $B_M$, and $C_M$). The temperature traces show three separately created slurry batches: a slurry composition having 15% glycerin (having a temperature setpoint of −8.1° C.) is represented by traces $A_C$ and $A_M$, and two different slurry batches both having 10% glycerin (having a temperature setpoint of −5.5° C.) are represented by traces $B_C$ and $B_M$, as well as traces $C_C$ and $C_M$. When a slurry batch is first introduced into the copper plate, the thermocouple wire embedded inside the plate (traces $A_C$, $B_C$, and $C_C$) initially measures the warm temperature of the heated plate (e.g., 31° C. for trace $A_C$ at timepoint 0) and then reaches an equilibrium at a lower temperature due to the cooling effect of the introduced slurry (e.g., 22° C. for trace $A_C$ at around 2 minutes). On the other hand, for the thermocouple wire located in the middle of the plate, when a slurry is first introduced into the copper plate it immediately contacts the thermocouple wire since that wire is exposed. This causes an initially negative temperature reading in the middle position due to the crystallized slurry contacting the wire (e.g., −5° C. for trace $A_M$ at timepoint 0) followed by an equilibrium at a warmer temperature as the slurry begins to melt on the heated plate (e.g., 18° C. for trace $A_M$ at around 4 minutes). The thermocouple wire exposed to the outside of the plate (traces $A_M$, $B_M$, and $C_M$) can be used to detect phase transitions during which the crystallized slurry begins to melt. The graph shows that the two slurry compositions with 10% glycerin reach their phase transition at similar timepoints (at around 4 minutes for trace $B_M$, and at around 2.7 minutes for trace $C_M$), which differ from the phase transition for the 15% glycerin slurry (phase transition occurs at around 0.2 minutes for trace $A_M$). The graph also shows that the two slurry batches having the same composition (10% glycerin: traces $B_C$ and $B_M$ and traces $C_C$ and $C_M$) reach equilibrium (as measured by the two thermocouple wire positions) in a similar time frame and at similar temperatures of between about 15° C. and 19° C. depending on the location of the thermocouple (middle/bottom). On the other hand, the slurry with a different composition (15% glycerin: traces $A_C$ and $A_M$) has a different temperature profile from the other two, reaching an equilibrium sooner at the temperature of between about 19° C. and 22° C. depending on the location of the thermocouple (middle/bottom). FIG. 3 therefore demonstrates that slurries of different compositions have different temperature profiles and batch to batch consistency exists across slurries having the same composition (e.g., the slurry represented by $B_C$ and $B_M$ and slurry represented by $C_C$ and $C_M$ have similar temperature profiles which is different from that of slurry represented by $A_C$ and $A_M$).

Figure 4A:
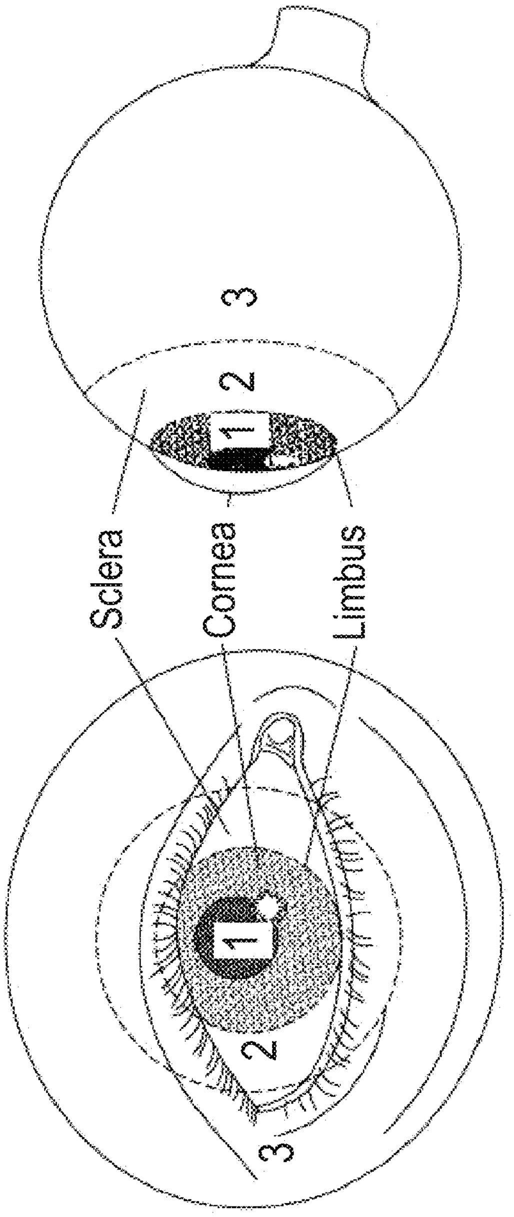
FIGS. 4A and 4B shows diagrams of a human eye showing different areas of the eye (4A) and degrees for anatomical reference (4B).
Figure 4B:
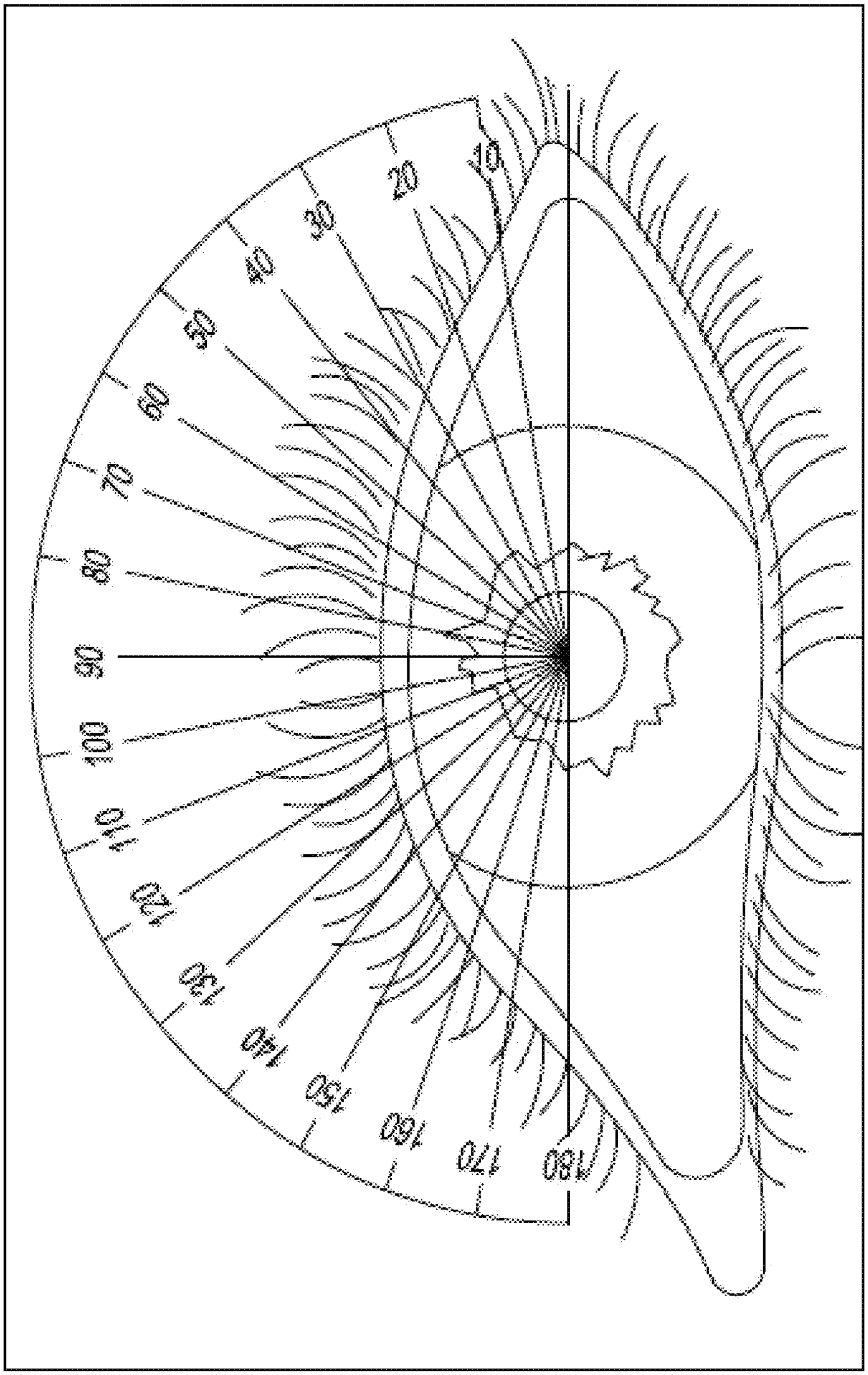

With reference to FIG. 4A, a diagram of an eye is shown depicting the sclera zone 2, sclera zone 3, cornea 1, and the corneal limbus (dotted line between cornea 1 and sclera zone 2. FIG. 4A is reproduced from Andreoli C M, Gardiner M F. Open globe injuries: Emergent evaluation and initial management. In: UpToDate, Post TW (Ed), UpToDate, Waltham, MA, available at https://eye.hms.harvard.edu/eye-insights/2014-april/benchmark-protocols-managing-eye-trauma. FIG. 4B shows a diagram of an eye with a superimposed protractor showing angles in degrees (°) with respect to the eye. In this diagram, 90° represents the superior most position along the eye.

In some embodiments, the cold slurries described herein can be applied topically directly or indirectly to the surface of the eye, or alternatively injected, to achieve long-lasting hypesthesia that reduces ocular surface discomfort. Hypesthesia, also referred to as hypoesthesia, refers to a reduction of discomfort or pain without a complete blockage of sensation, which, in the present disclosure, is related specifically to the sensation of the ocular surface or ocular structures. Hypesthesia is therefore distinguished from anesthesia, anesthesia being characterized as a more profound blockage of ocular sensation. Hypesthesia of the ocular surface may include corneal numbing which causes a reduction in pain response, while maintaining an otherwise normal functioning of the eye, including a normal healing process. Anesthesia, on the other hand, may lead to abnormal functioning of the eye since all corneal sensation is lost. Corneal sensation is important for normal functioning of the eye including the initiation of protective mechanisms such as blinking and tear production.

In certain embodiments, the cold slurries or devices described herein can be configured to cause a complete loss of corneal sensation, i.e., anesthesia. This can be advantageous for surgical procedures or other eye treatments.

In certain embodiments drops of the cold slurry are applied directly to the ocular surface. In some embodiments, the amount of slurry applied directly to the surface of the eye may vary in volume from 1 to 100 milliliters. In certain embodiments, the amount of slurry applied directly to the surface of the eye may be approximately 10 to 80 milliliters.

In some embodiments, the formulation may be directly administered to the ocular surface. In alternative embodiments, the cornea may be scraped first, and drops may be subsequently administered directly to the surface of the eye. In some embodiments, the topically applied cold slurry has a flowable paste consistency, and a large quantity could be applied topically (e.g., 3-50 ml) to the ocular surface as a treatment.

In some embodiments, the cold slurries or self-contained cooling devices as described herein are applied topically to the surface of the eye, directly or indirectly, for between about 1 minute and about 20 minutes, between about 2 minutes to about 5 minutes, between about 10 minutes to about 15 minutes, or between about 15 minutes to about 20 minutes. In some embodiments, the cold slurry or self-contained cooling device is applied for between about 5 minutes and about 10 minutes. In some embodiments, cold slurry or self-contained cooling device is administered about every 1 to about 10 seconds for about 1 to about 20 minutes into each eye. This treatment could be repeated several times over a short period of time (e.g., 5-20 min). In some embodiments, the cold slurry or self-contained cooling device is applied topically to the surface of the eye, directly or indirectly, for about 10 minutes, with fresh slurry or a fresh device re-applied about every 90 seconds until about 10 minutes is reached. In certain embodiments, the slurry is applied directly or indirectly to the surface of the eye posterior to the corneal limbus, e.g., the area denoted as sclera zone 2 in FIG. 4A.

In some embodiments, during the topical application, sensitive ocular structures are protected from encountering the cold slurry in order to limit potential side effects. For example, protection of the corneal surface may limit some or all corneal cell damage or refractive changes caused by freezing the corneal tissue. Protection of the palpebral conjunctiva and eye lids may prevent redness, swelling and inflammation that would not be related to the treatment effect. By selectively applying the slurry directly or indirectly to the ocular surface posterior to the limbus over the bulbar conjunctiva (corresponding to the anterior anatomical area known as zone 2, FIG. 4A), potential adverse effects to the cornea may be minimized.

In some embodiments, a protective contact lens or other protective cover such as those described further herein can be applied to sit on the cornea to protect the cornea from potential damage from the slurry. In some embodiments, a corneal covering completely blocks the cold slurry from contacting the cornea surface directly. In some embodiments, a lid protecting device is used to keep the eye lids open during cold slurry topical application. In some embodiments, the lid protecting device is made of a thermally non-conductive material such as plastic or another non-conductive material known in the art. A thermally non-conductive material may be used for the lid protecting device to prevent the eyelids (inside and outside) from contacting the slurry and potentially freezing, which could cause damage to the eyelids, during cold slurry treatment. In certain embodiments, the lid protecting device comprises a speculum to assist in keeping the eyelids open. In some embodiments, the cold slurry is applied to the sclera only and the cornea is protected from contacting the slurry and potentially freezing.

In certain embodiments, as described further herein a device could be used to control the areas exposed to the cold slurry to just the bulbar conjunctiva/sclera so that the cold slurry does not physically contact or freeze adjacent tissues that are not relevant to the desired clinical effect. In some embodiments, the cold slurry formulation does not have direct contact with the ocular surface at all. In certain embodiments, the cold slurry formulation may be contained within a device and contact a material that is thermally conductive and that contacts the surface of the eye, e.g., a small metal or polymeric donut, other protective ring, or a concave surface capable of contacting the surface of the eye, thus providing a barrier against direct contact of the formulation with the ocular surface but allowing the requisite cooling of the ocular surface to occur. In some embodiments, the device directs cooling only to the areas of potential therapeutic effect and prevents the device/cooling from contacting and affecting adjacent tissues in order to minimize potential undesired side effects (e.g., potential irritation of the eye from the application of a hyperosmolar solution directly to the eye).

In some embodiments, the cold slurries described herein are injected as a subconjunctival bolus. In certain embodiments, the cold slurries are injected at about every 2 minutes. In some embodiments, each injection provides approximately 0.5-1.5 ml of frozen slurry. In certain embodiments an injection may be repeated approximately every 2 minutes for the duration of desired treatment. In some embodiments, the duration of the treatment is about 10 minutes, about 15 minutes, about 20 minutes, or more than about 20 minutes in total. In some embodiments, the cold slurry is injected more directly near the axons of the ciliary nerves. The ciliary nerves are located at approximately 0° and 180° of the eye (FIG. 4B).

In some embodiments, a standard syringe is used to inject slurry. In certain embodiments, a syringe that has conditioned the slurry for injection may be used. In some embodiments, the syringe may have a needle of about 18 G to about 25 G.

In some embodiments, real-time temperature sensing on the surface of the eye is performed during the treatment (e.g., cold slurry injection, slurry topical application, or topical application of a self-contained cooling device). In some embodiments, the cold slurry or self-contained cooling device is applied to cool the tissue (e.g., corneal surface, conjunctiva, or any other part of the eye) to less than about 0° C., less than about −1° C., less than about −2° C., less than about −3° C., less than about −4° C., or less than about −5° C. In some embodiments, the cold slurry or self-contained cooling device is applied for over about one minute, for between about 2 minutes and about 10 minutes, between about 5 minutes and about 10 minutes, between about 10 minutes and about 20 minutes, between about 10 minutes and about 15 minutes, or between about 15 minutes and about 20 minutes. The temperature of the cooled tissue and the length of time that the slurry or self-contained cooling device is applied can be varied to vary the hypesthesia experienced by a subject.

In some embodiments, the cold slurry or cooling treatment is periodically readministered to a subject's eye over time to maintain therapeutic effects. There is a range of possible frequencies for topical administration and/or injection. For example, treatment could be administered any one of the following: once a week, once every other week; once a month; once every other month; once every third month, etc.

In some embodiments, the cold slurry is used as a safe corneal numbing treatment to treat corneal discomfort or pain. Various formulations of cold slurries can be used with the methods described herein, including those described above. Additional specific embodiments of cold slurries are described with reference to FIGS. 5-9. "ETX-4143" is a slurry formulation that comprises 15% glycerol, 30% L-α-phosphatidylcholine liposomes, and 0.9% saline (or phosphate buffered saline). In some embodiments, ETX-4143 is administered to the eye (topically or via injection) at a temperature of between about −25° C. and −10° C. (temperature of the slurry). In some embodiments, ETX-4143 is administered to the eye (topically or via injection) at a temperature of about −18° C. (temperature of the slurry, such as in the embodiments described below with reference to FIGS. 5-9). ETX-4143 is administered every approximately 90 seconds, with approximately 2-3 ml per application, until a total treatment time of 10 minutes is reached.

"ECT-1719" is a slurry formulation that comprises 15% glycerol and 0.9% saline (or phosphate buffered saline). In some embodiments, ECT-1719 is administered to the eye (topically or via injection) at a temperature of between about −20° C. and −5° C., or between about −15° C. and about −10° C. (temperature of the slurry). In some embodiments, ECT-1719 is administered to the eye (topically or via injection) at a temperature of about −11° C. (temperature of the slurry, such as in the embodiments described below with reference to FIGS. 5-9). In some embodiments, ECT-1719 is injected in 0.7 ml volume per injection, with four total injections making up 2.8 ml of total injected volume. ECT-1719 is administered every approximately 120 seconds until a total treatment of 10 minutes is reached.

Figure 5:
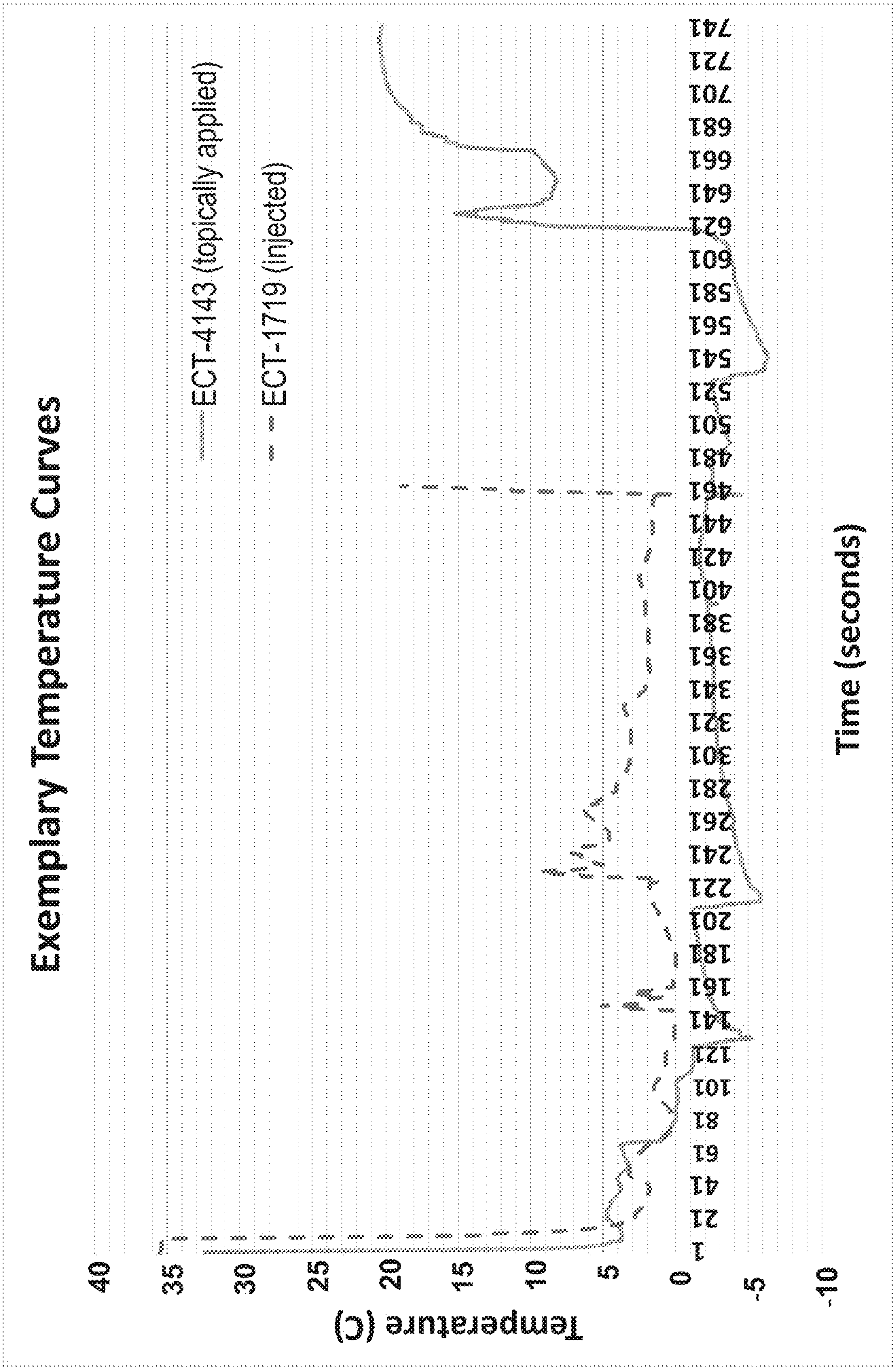
FIG. 5 is a graph showing real-time scleral temperature monitoring in rabbits following administration to the eye of a topically applied cold slurry (solid line) and an injected cold slurry (dashed line).

Referring to FIG. 5, real-time scleral temperature monitoring was performed in rabbits following administration to the eye of a topically applied cold slurry (ETX-4143, solid line) in one rabbit and an injected cold slurry (ECT-1719, dashed line) in a second rabbit. The temperature monitoring is achieved by cannulating the subtenon's space with a 25 G needle containing a temperature probe at its distal end. As can be seen in FIG. 5, the scleral temperature of the rabbit that received the injected cold slurry (ECT-1719) fluctuated between about 0° C. and about 8° C. throughout the duration of the procedure (from about 0 seconds following cold slurry injection to about 463 seconds following cold slurry injection). The sharp line in the graph at about 463 seconds represents conclusion of the study after 7.5 minutes and removal of the temperature probe from the ocular tissue. The scleral temperature of the rabbit that received the topically applied cold slurry (ETX-4143) was lower than for the injected cold slurry with fluctuations between about −6° C. and about 4° C. for the majority of the time during which temperature was recoded (between about 0 seconds following topical application and about 600 seconds following topical application). Following topical application, the temperature of the sclera continued to drop from about 4° C. at the time of application (about 0 seconds in FIG. 5) to about 0° C. after about 120 seconds. Following the initial period of scleral cooling, the temperature remained relatively stable at between about 0° C. and −5° C. from about 120 seconds after topical application to about 520 seconds after topical application. Additionally, for a duration of between about 220 seconds and about 520 seconds following topical application, the scleral temperature showed very little variability, remaining stable at about −2° C. to about −3° C. After about 620 seconds following topical application, the treatment is concluded and the temperature probe is removed, showing a sharp increase in measured temperature as shown in FIG. 5.

The hypesthetic effect following the cooling treatment (whether by injection or application of a cold slurry or application of a self-contained cooling device) may be measured as a response to tactile stimulation of the eye using a monofilament/esthesiometer. Starting at 6 cm filament length and decreasing by 0.5 cm increments, the eye is probed three times at each length until a blink response is elicited. The filament gets stiffer as it is shortened, therefore imparting more pressure on the eye when probed into the eye. The hypesthesia for each time point is based on a given length of the monofilament. At each time point, the specific monofilament length that is recorded is the shortest length (highest pressure) at which blink response is not present. For example, starting with the longest monofilament of 6 cm, if the rabbit does not blink when probed, the next monofilament of 5.5 cm length is used to probe the eye. If the rabbit does not blink again, the next monofilament length of 5 cm is used. Now, if the rabbit does blink, the previous length of 5.5 cm is recorded because this is the shortest length at which there was no blink response (reflecting a certain degree of hypesthesia). The deepest level of hypesthesia is when a rabbit does not blink when probed with the shortest filament length (e.g., 0.5 cm). Zero degree of hypesthesia (no blockage of pain/no numbing) is when a rabbit blinks when probed with the longest filament length (e.g., 6 cm). The filament length can be converted into a pressure ($g/mm^2$) such that 6 cm filament produces 0.4 $g/mm^2$ pressure (the lowest pressure), while 0.5 cm filament produces 15.9 $g/mm^2$ pressure (the highest pressure). Therefore, the recorded pressure is the pressure that corresponds to the shortest filament length where blink response is not present.

Figure 6:
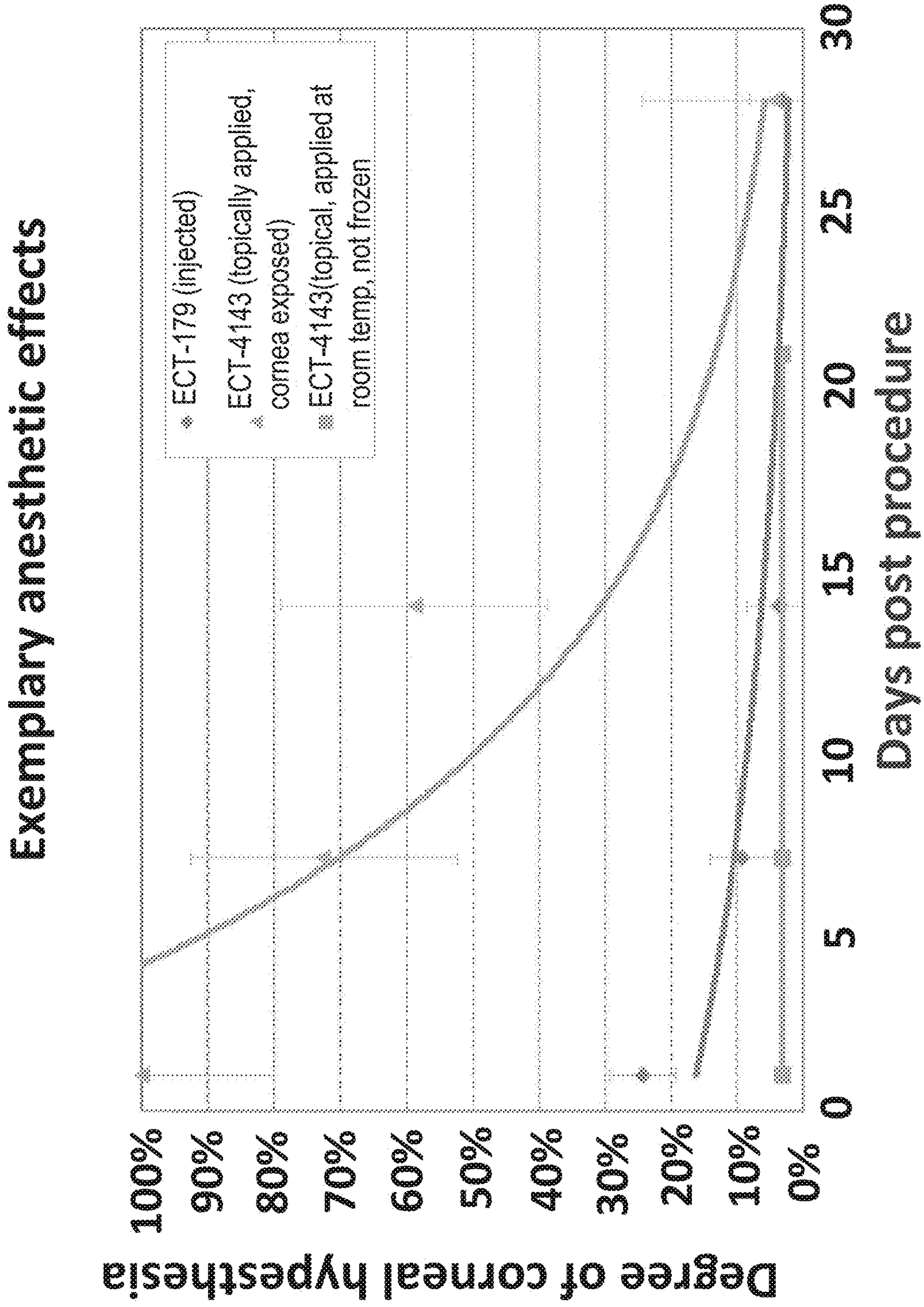
FIG. 6 is a graph showing hypesthesia in rabbits' eyes over time following administration to the eye, with the cornea exposed, of an injected cold slurry (diamond), a topically applied cold slurry (triangle), and a topically applied slurry at room temperature (square).

Referring to FIG. 6, the hypesthetic effect (degree of corneal numbing measured using tactile stimulation as described herein) was measured in rabbits over time following administration to the eye, with the cornea exposed, of an injected cold slurry (ECT-1719, 3 rabbits in this group, shown with a diamond), a topically applied cold slurry (ETX-4143, 3 rabbits in this group, shown with a triangle), and a topically applied slurry at room temperature (ETX-4143, 1 rabbit in this group, shown with a square). In FIG. 6, the degree of hypesthesia is shown as a percentage of the recorded pressure (i.e., based on the shortest monofilament in which there is a lack of blink response) relative to the highest possible pressure (i.e., shortest monofilament used of 0.5 cm corresponding to 15.9 $g/mm^2$ pressure). The degree of hypesthesia is shown for days 1, 7, 14, and 28 following cold slurry administration. For the injected cold slurry (ECT-1719, shown with a diamond), the hypesthetic effect at day 1 was about 20% and continued to taper off reaching baseline levels by day 14 (error bar overlaps with 0%). For the topically applied cold slurry (ETX-4143 applied at 18° C., shown with a triangle), the hypesthetic effect at day 1 was 100% (maximal corneal numbing that could be measured), which then continued to drop, tapering off at day 28 during which the pain response returned to baseline levels (error bar overlaps with 0%). For the topically applied slurry at room temperature (ETX-4143, shown with a square), no hypesthetic effect could be observed at any time point following treatment. FIG. 6 therefore demonstrates an unexpectedly strong hypesthetic effect for topically applied cold slurry which results in long-lasting hypesthesia (almost 1 month). Injected cold slurry results in moderate hypesthesia which also lasted longer than expected (e.g., between about 1 week and 2 weeks). Importantly, for both topical and injection methods, cold slurry treatment produced long-lasting hypesthesia which normalized back to baseline levels without causing any permanent numbing effect.

Figure 7:
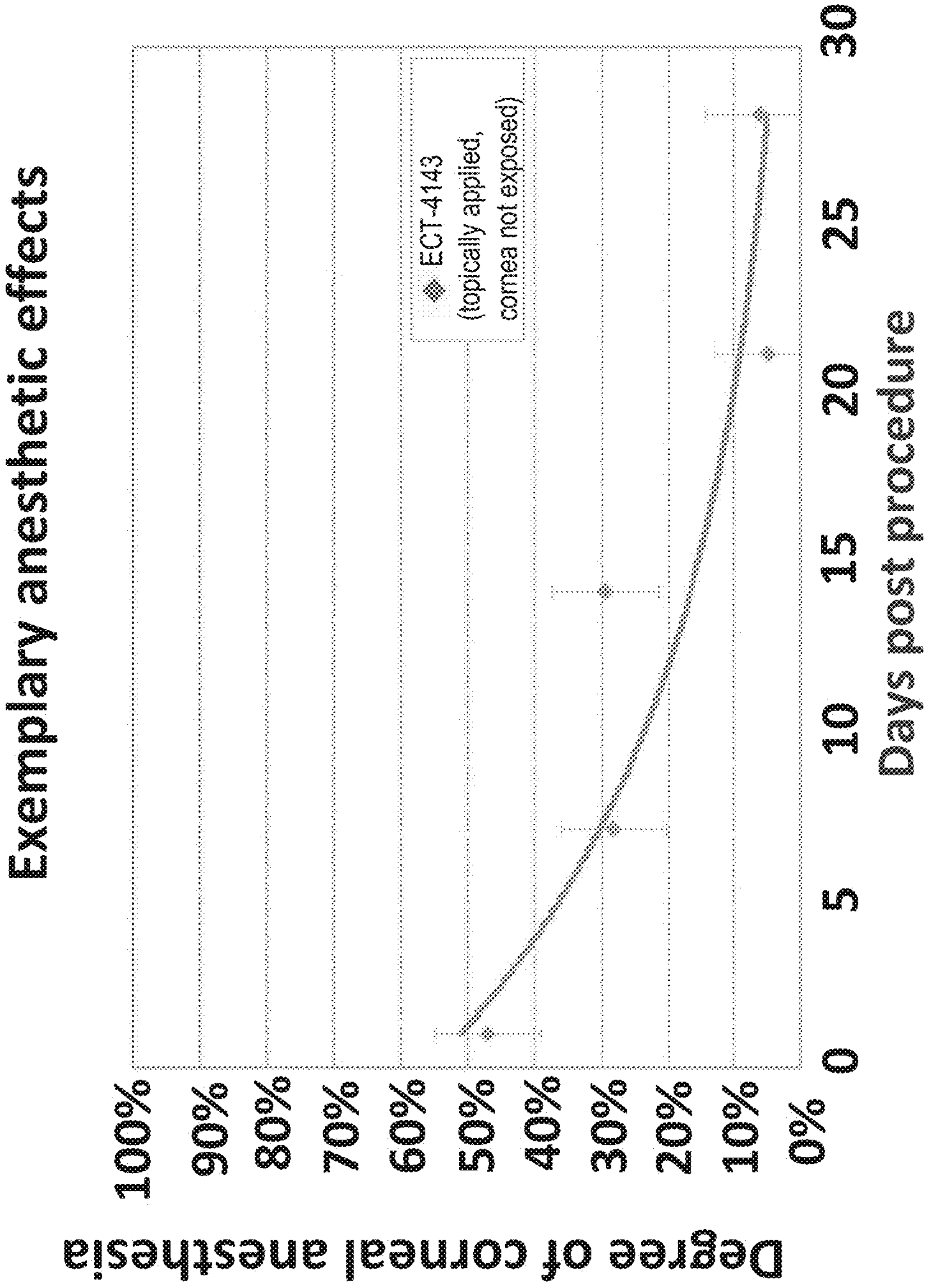
FIG. 7 is a graph showing hypesthesia in rabbits' eyes over time following administration to the eye, with the cornea not exposed, of a topically applied cold slurry.

FIG. 7 shows hypesthetic effect in rabbits over time following administration to the eye of a topically applied cold slurry (6 rabbits, ETX-4143) similar to FIG. 6, except with the cornea not exposed (protected with a contact lens). The hypesthetic effect was measured in the same way as described above with respect to FIG. 6. The hypesthetic effect is shown for days 1, 7, 14, 21, and 28 following treatment with the topically applied cold slurry. The hypesthetic effect was at about 50% at day 1 and tapered off slowly reaching baseline levels by day 21 (error bar overlaps with 0%). FIG. 7 therefore demonstrates an unexpectedly moderate-to-strong hypesthetic effect for topically applied cold slurry (with corneal protection) which results in long-lasting hypesthesia (about 3 weeks) without causing permanent corneal numbing or any corneal damage.

Figure 8A:
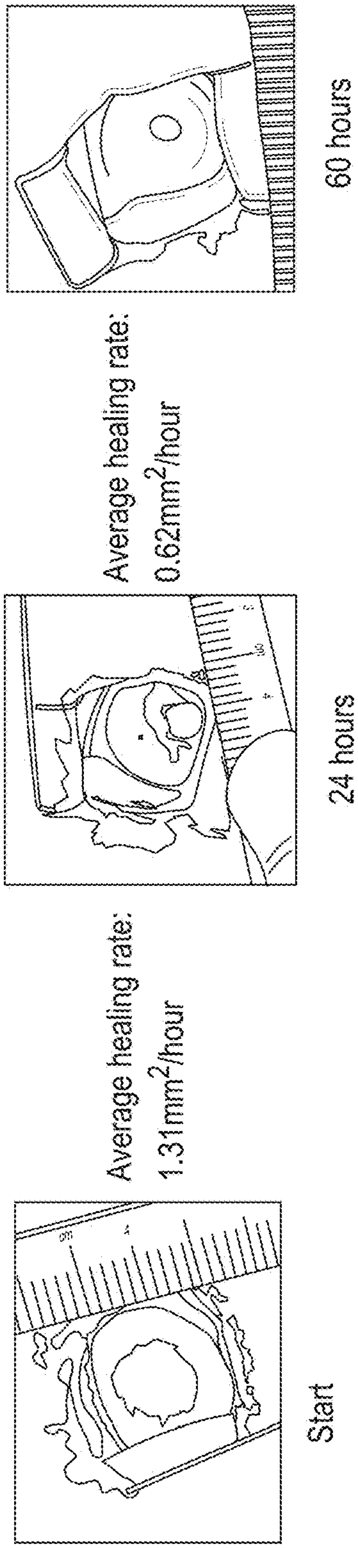
FIGS. 8A and 8B are images of fluorescein stained rabbit cornea showing corneal healing over time following intentional 8 mm corneal abrasion (8A) as a control group and following topical application of cold slurry (8B).
Figure 8B:
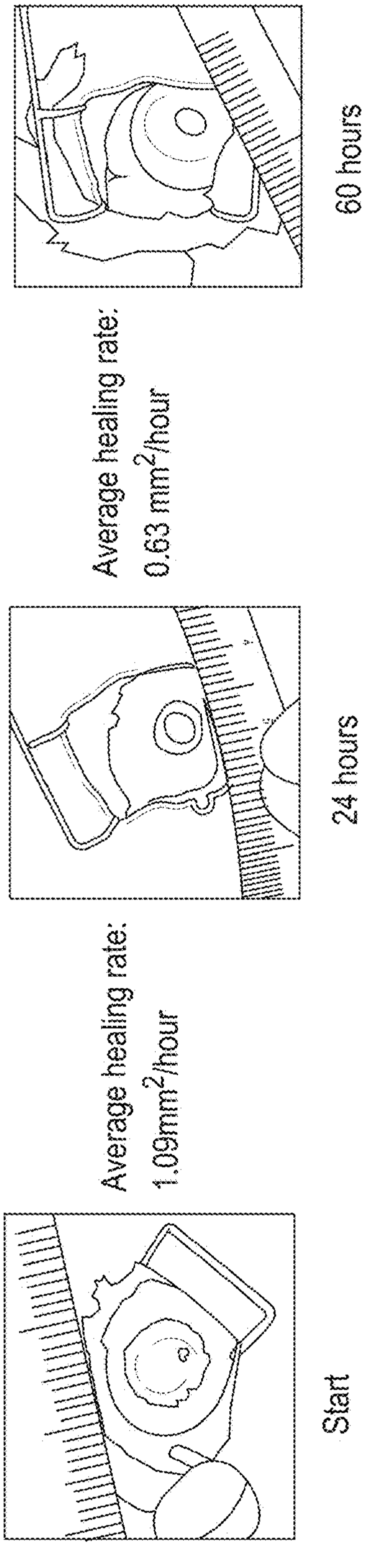

Referring to FIG. 8, representative images of rabbit corneas using fluorescein staining demonstrate corneal healing over time following intentional 8 mm corneal abrasion applied to both the control group (FIG. 8A) and following topical application of cold slurry in the treatment group (FIG. 8B) with protection applied to the corneas and eyelids. The progress of the injury is determined by measuring the size of the injury over time. As can be seen in FIG. 8A, corneal healing in the control group (3 rabbits) occurred at an average healing rate of 1.31 $mm^2$/hour in the first 24 hours following corneal abrasion and 0.62 $mm^2$/hour between 24 hours and 60 hours following corneal abrasion. Unexpectedly, as shown in FIG. 8B, corneal healing was not impaired compared to the control group for rabbits that received topically applied cold slurry (ETX-4143). In this group (3 rabbits), corneal healing following cold slurry treatment occurred at an average healing rate of 1.09 $mm^2$/hour in the first 24 hours following cold slurry treatment and 0.63 $mm^2$/hour between 24 hours and 60 hours following cold slurry treatment.

Figure 9:
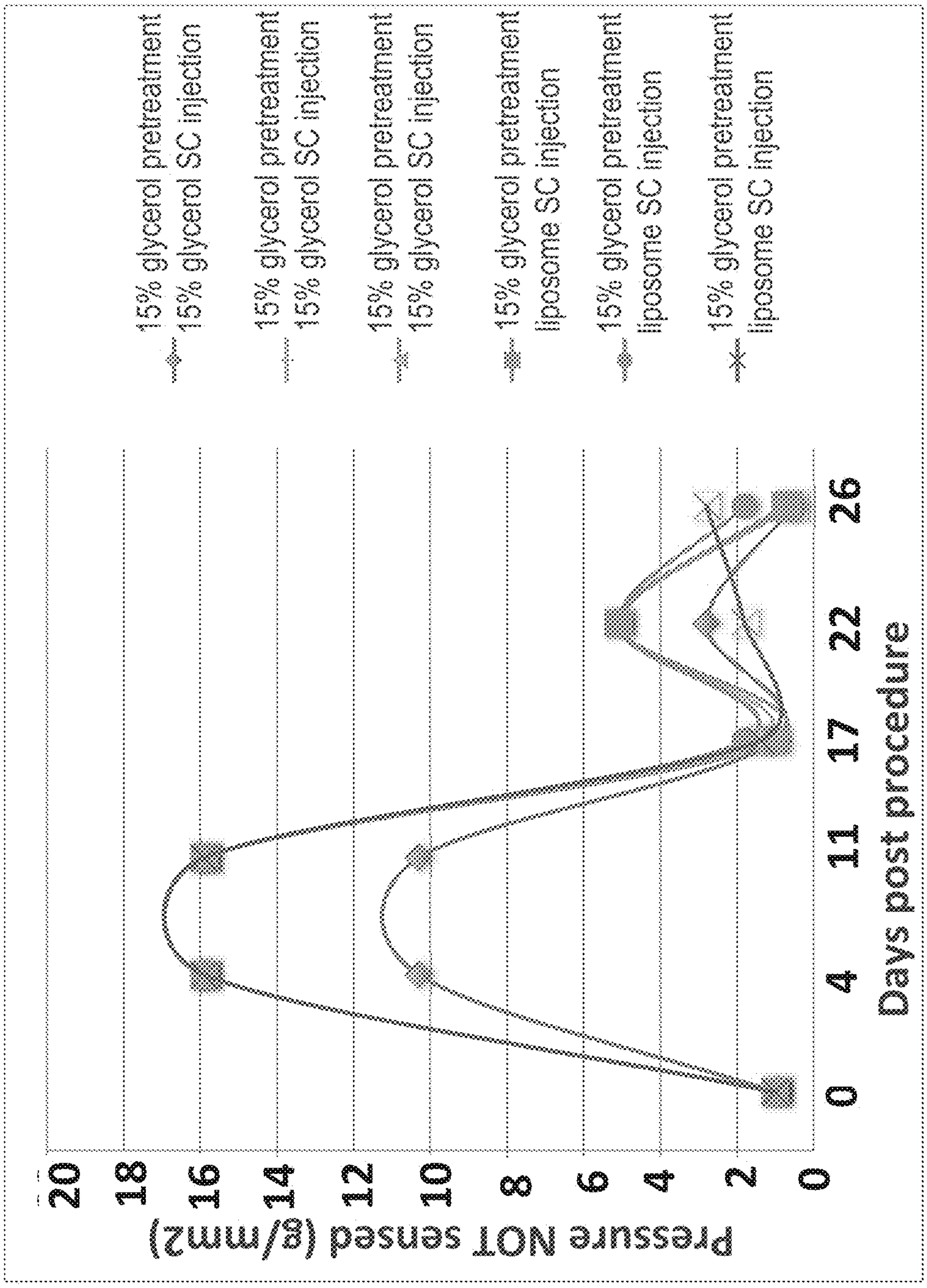
FIG. 9 is a graph showing hypesthesia in 6 rabbits' eyes over time after a combination treatment in which a cold slurry was topically applied first and then injected. In three rabbits (shown with a diamond, square, and triangle), the injected slurry did not contain liposomes, while in the other three rabbits (shown with an "X", star, and circle), the injected slurry contained liposomes.

Referring to FIG. 9, a graph shows the hypesthetic effect in 6 rabbits over time after a combination treatment in which a cold slurry was topically applied first and then injected. In 3 rabbits (shown with a diamond, square, and triangle), the topically applied cold slurry was ECT-1719 which does not contain liposomes which was followed by an injection of the same cold slurry formulation (ECT-1719). In the other 3 rabbits (shown with an "X", star, and circle), the topically applied cold slurry was again ECT-1719 (which does not contain liposomes) which was followed by an injection of cold slurry that contains liposomes (ETX-4143). The hypesthetic effect is shown as the greatest pressure to which rabbits did not produce a blink (as described herein with reference to FIGS. 6 and 7). As shown in FIG. 9, the hypesthetic effect continued to increase following treatment, likely peaking somewhere between days 4 and 11, irrespective of combination treatment (liposomal or non-liposomal injection). The hypesthetic effect tapered off returning to baseline levels at about day 17. Surprisingly, a second, less pronounced period of hypesthesia spontaneously occurred at around day 22, tapering back to baseline levels by day 26.

Cold Slurry Formulations Comprising One or More Lipids

In certain embodiments, it is desirable to increase the ice fraction in the slurry because this translates into a greater amount of thermal energy being carried away from the ocular surface. However, adding more ice to the cold slurry generally makes the slurry less flowable, causing difficulty in its injection or topical administration to the site of interest. As described further herein, certain embodiments of the invention are directed to the cold slurry formulations described herein further comprising one or more lipids that enhance flowability of the slurry. In certain embodiments, the one or more lipids enhances the flowability and flow characteristics of the slurry while also allowing for the desired amount of ice fraction in the slurry. In some embodiments, an enhanced flowability leads to improved properties of the slurry to better allow for application through devices (e.g., syringes) of various sizes for injectable and/or topical administration of the slurry.

In some embodiments, the slurry comprises one or more lipids, which results in the formation of an emulsion with the ice and/or ice-freezing point depressant mixture in the slurry, preventing or reducing agglomeration of the ice particles into larger crystal sizes that reduce flowability of the slurry. In some embodiments, the slurry comprises one or more lipids, which prevent, or reduce the amount of, agglomeration of smaller ice crystals into larger crystals by encapsulating the ice and/or ice-freezing point depressant crystals while they are of smaller size.

In some embodiments, the slurry comprises an amount of lipid that varies between about 0%-45% (v/v). In some embodiments, the slurry comprises an amount of lipid that varies between about 0%-10%, about 10%-20%, about 20%-30%, or about 30%-45. In some embodiments, the slurry comprises an amount of freezing point depressant that varies between about 0%-10%, about 10%-40%, about 10%-30%, about 10%-20%, or about 40%-50% (v/v). In some embodiments, the slurry comprises amounts of lipid and freezing point depressant (e.g., glycerol) that vary between about 15%-45% (v/v) and 10%-25% (v/v), respectively. In some embodiments, the slurry comprises an amount of lipid that is between about 0%-45% (v/v) and/or an amount of freezing point depressant (e.g., glycerol) that is between about 0%-45% (v/v).

In some embodiments, the slurry, which may comprise water, one or more freezing point depressants, and/or one or more lipids, is prepared by flash freezing. In certain embodiments, the slurry, which may comprise water, one or more freezing point depressants, and/or one or more lipids, is prepared by freezing the slurry in a −20° C. freezer, a −80° C. freezer, an ultra-low temperature ("ULT") freezer, or by flash freezing (e.g., using liquid nitrogen, etc.) that results in an emulsified slurry. In certain embodiments, such an emulsified slurry can be stored in a standard freezer and will retain its flowability when taken out from the freezer for use (e.g., in a treatment procedure).

In some embodiments, the slurry, which may comprise water, one or more freezing point depressants, and/or one or more lipids may be contained within one or more syringes. In some embodiments, the one or more slurry-containing syringes is prepared by flash freezing the one or more syringes containing the slurry. In certain embodiments, the one or more slurry-containing syringes is prepared by cooling the slurry-containing syringe in a −20° C. freezer, a −80° C. freezer, an ultra-low temperature ("ULT") freezer, or by flash freezing (e.g., using liquid nitrogen, etc.) that results in emulsification of the slurry. In certain embodiments, the one or more slurry-containing syringes may be conveniently stored in a standard freezer without experiencing any noticeable loss in flowability characteristics.

In some embodiments, the slurry comprises one or more lipids that has low degradability characteristics, resulting in long-term stability of the slurry mixture. In some embodiments, the slurry comprises one or more lipids comprising soy-Phosphatidylcholine (soy-PC). In some embodiments, the slurry comprises one or more lipids comprising one or more fatty acids. In certain embodiments, the one or more fatty acids are selected from the group consisting of stearic acid, palmitic acid, lauric acid, and myristic acid. In some embodiments, the slurry comprises one or more lipids that is derived from a non-animal source, including soy-based and synthetic alternatives. In some embodiments, the slurry comprises a non-lipid, including hyaluronic acid, polysorbate, and other hydroscopic molecules.

Figure 10:
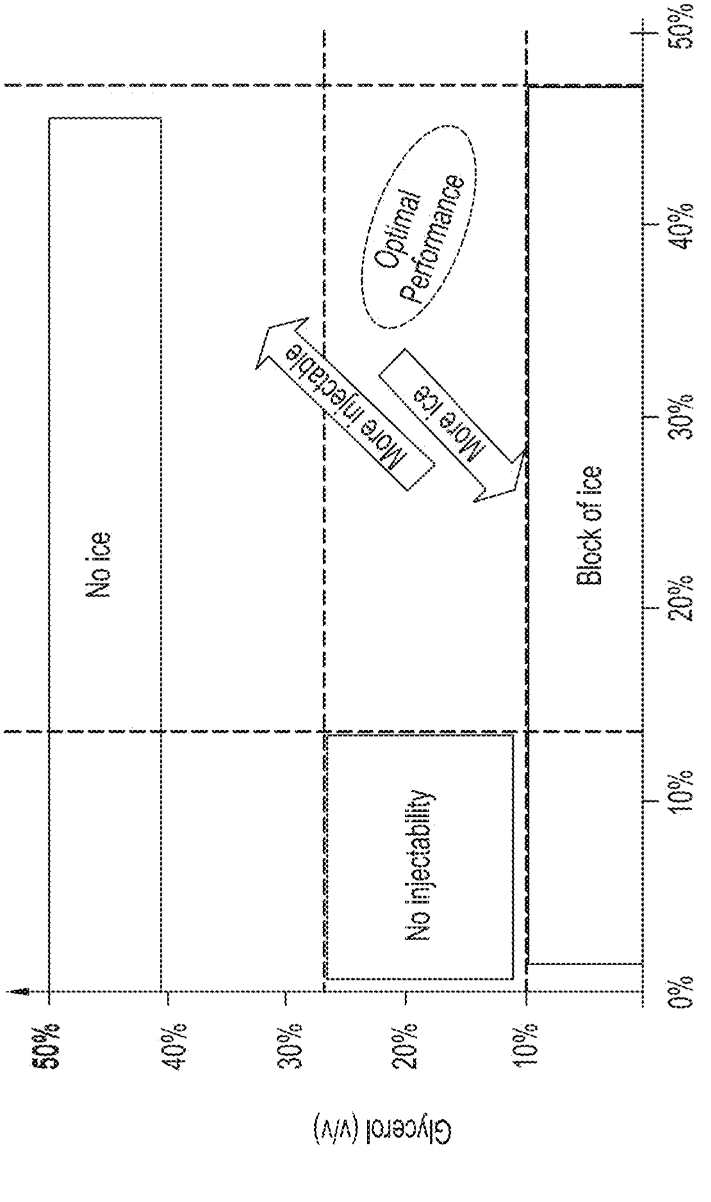
FIG. 10 is a graph showing degree of injectability of an embodiment of a cold slurry comprising ice, the freezing point depressant glycerol, and lipid as a function of the volumetric fractions of the glycerol and lipid in the cold slurry.

Referring to FIG. 10, a diagram of degree of injectability of an exemplary cold slurry comprising ice, glycerol, and lipids as a function of volumetric fractions of glycerol and lipid is shown. When the amount of glycerol and lipid in the cold slurry is in the range of about 0%-10% (v/v) and about 0%-45% (v/v), respectively, the slurry is not flowable or injectable because the ice within the cold slurry aggregates into large blocks. When the amount of glycerol and lipid in the cold slurry is in the range of about 10%-25% (v/v) and about 0%-15% (v/v), respectively, the slurry remains non-flowable and non-injectable because the ice within the cold slurry aggregates into crystal sizes large enough to prevent free flow of the cold slurry from the syringes of appropriate sizes. When the amount of glycerol and lipid in the cold slurry is in the range of about 40%-50% (v/v) and about 0%-45% (v/v), respectively, no ice is present in the slurry as the freezing point of the water is depressed such that any water present in the slurry is in liquid form, rendering the cold slurry ineffective for the cold slurry application. When the amount of glycerol and lipid in the cold slurry is in the range of about 25%-40% (v/v) and about 0%-45% (v/v), respectively, the cold slurry is more flowable and is injectable as the ice crystals are small enough in size to allow them to flow freely; however, the amount of ice in the cold slurry remains low, making the cold slurry not as effective in carrying away the heat as is required in the cold slurry application. When the amount of glycerol and lipid in the cold slurry is in the range of about 10%-25% (v/v) and about 15%-45% (v/v), respectively, the cold slurry is flowable and both injectable and an effective heat carrier. In this performance range, depending on the desired degree of injectability of the cold slurry, the heat carrying capacity of the cold slurry can be maximized. In some embodiments, the lipid used in FIG. 10 is soy-PC.

In general, the cold slurry containing higher amounts of ice will remove more heat from the eye surface but will be less flowable because of the presence of ice particles. On the other hand, adding a freezing point depressant (e.g., glycerol) and lipid to the slurry is expected to improve the flowability of the slurry but reduces the amount of ice and thus the heat carrying capacity of the slurry. When the amount of glycerol in the cold slurry is in the range of about 0%-10% (v/v), the amount of glycerol is not sufficient to depress the freezing temperature enough to prevent enough of the water from freezing. Regardless of the amount of lipid added to the slurry, small ice crystals will begin to form and then start agglomerating into larger crystals that further coalesce to result in large blocks of ice. Such large blocks of ice cause the slurry to become non-flowable, rendering the cold slurry mixture to become unworkable for injection or direct topical administration to the eye, though a non-flowable cold slurry can be used in combination with a self-contained cooling device to apply cooling treatment to the ocular surface. When the amounts of glycerol and lipid in the slurry are in the range of about 10%-25% and 0%-15% (v/v), respectively, the cold slurry still lacks the flowability needed for injection or topical administration purposes. When the amounts of glycerol and lipid in the slurry are in the range of about 25%-40% and 0%-40% (v/v), respectively, there is enough glycerol present in the cold slurry to lower the freezing point of the ice to a desired level while still exhibiting flow characteristics that permit some degree of injectability. For example, in this range, even when the cold slurry contains no lipid, the slurry may nevertheless exhibit a depressed freezing point and a flowability that may allow its use in the cold slurry treatment. When the amounts of glycerol and lipid in the slurry are in the range of about 25%-40% and 15%-45% (v/v), respectively, the increasing amount of lipid increases the flowability of the slurry; however, this also results in decreasing amount of ice and thus a reduced heat carrying capacity of the cold slurry. When the amount of glycerol in the slurry is more than about 40% v/v, the water component of the slurry will remain liquid at the target temperature at which the eye surface needs to be maintained at (i.e., about −6° C. and 4° C.). Since the cold slurry treatment relies on the latent heat of the ice (and not the sensible heat of the liquid water which results in significantly less heat carrying capacity for the temperature differences experienced in the treatment) to maintain low temperature of the eye surface for prolonged periods of time, this range is not suitable for the cold slurry treatment. An optimized cold slurry consists of amounts of glycerol and lipids that vary between about 25%-40% and 15%-45% (v/v), respectively. Such cold slurry will maximize the heat carrying capacity of the cold slurry without compromising its flowability and thus injectability required for the slurry application (e.g., desired injectability depending on the size of the syringe, treatment temperature, etc.).

In some embodiments, the invention is directed to a cold slurry formulation comprising water, one or more freezing point depressants, and one or more lipids. In certain embodiments, the slurry formulation is configured to maintain the desired temperature of an eye surface for prolonged periods of time. In certain embodiments, the slurry formulation comprises about 25%-40% (v/v) of a freezing point depressant. In some embodiments, the freezing point depressant is glycerol. In certain embodiments, the slurry formulation comprises about 15%-45% (v/v) lipid. In some embodiments, the lipid is soy-Phosphatidylcholine (soy-PC).

In some embodiments, the invention is directed to a method of alleviating symptoms of ocular surface discomfort, the method comprising: topically applying a cold slurry adjacent to a corneal limbus of an eye of a patient, wherein the cold slurry comprises water, a freezing point depressant, and one or more lipids, wherein the topical application of the cold slurry is configured to cause a degree of numbing of a cornea of the eye for a period of time, and wherein an ocular sensation of the eye is restored following the period of time.

In some embodiments, the invention is directed to a method for preparing a cold slurry formulation, the method comprising mixing the desired fractions of water, one or more freezing point depressant, and one or more lipids at a mixing speed of 1-20,000 RPM. In some embodiments, the invention is directed to a method for preparing a cold slurry formulation by gently agitating the desired fractions of water, one or more freezing point depressant, and one or more lipids. In certain embodiments, the slurry formulation comprises about 25%-40% (v/v) of a freezing point depressant. In some embodiments, the freezing point depressant is glycerol. In certain embodiments, the slurry formulation comprises about 15%-45% (v/v) lipid. In some embodiments, the lipid is soy-Phosphatidylcholine (soy-PC). In some embodiments, such a method for preparing a cold slurry formulation provides an emulsified slurry comprising an emulsion of water with the one or more lipids or water and freezing point depressant constituents with the one or more lipids. In some embodiments, such method for preparing a slurry formulation provides a stable dispersion of one or more lipid particles in water or water and freezing point depressant constituents. In certain embodiments, such method for preparing a slurry formulation causes the water constituent to form small micro and/or mm-sized droplets that are encapsulated by one or more lipids. In certain embodiments, such a method for preparing a slurry formulation causes the water and freezing point depressant constituents to form small micro and/or mm-sized droplets that are encapsulated by one or more lipids.

Devices for Protecting the Cornea

In some embodiments, aspects of the invention are directed to devices for protecting the cornea. In certain embodiments, the devices described herein for protecting the cornea may be used when applying the slurry described herein to the eye of a subject. In certain embodiments, contacting certain portions of the eye (e.g., the cornea) with the cold slurry described herein may pose a risk of damage to the area (e.g., cornea) such as: 1) subzero temperature of the cold slurry may cause the cornea to freeze, and/or 2) chemicals used in the slurry may be harmful to (e.g., may irritate) the cornea. Therefore, in certain embodiments of contacting the eye of a subject with the slurry described herein, a physical and thermal protection/isolation of the cornea from the cold slurry may be desired.

In some embodiments, a device for protecting the cornea, as described herein, comprises a member that provides suction force, such as a suction cup. In certain embodiments, the member providing suction force is placed over the cornea, covers the cornea, and is held in place by suction force. In certain embodiments the member providing suction force of the cornea-protecting device forms a seal around the perimeter of the cornea. In some embodiments in which the cornea-protecting devices is used in combination with the application of the slurry to the surface of the eye, the member providing suction force provides a seal around the perimeter of the cornea preventing the deposited (i.e., topically administered or injected) slurry from coming in direct contact with the cornea. The diameter of the member providing suction force (e.g., suction cup) of the cornea protecting device may be of various sizes to accommodate corneas of different sizes, allowing for the device to be used on different subjects, including animals and humans, of different ages and sizes (e.g., children, adults, etc.). For example, the diameter of the opening of the member providing suction force (e.g., suction cup) may range from 11-14 mm.

Figure 11:
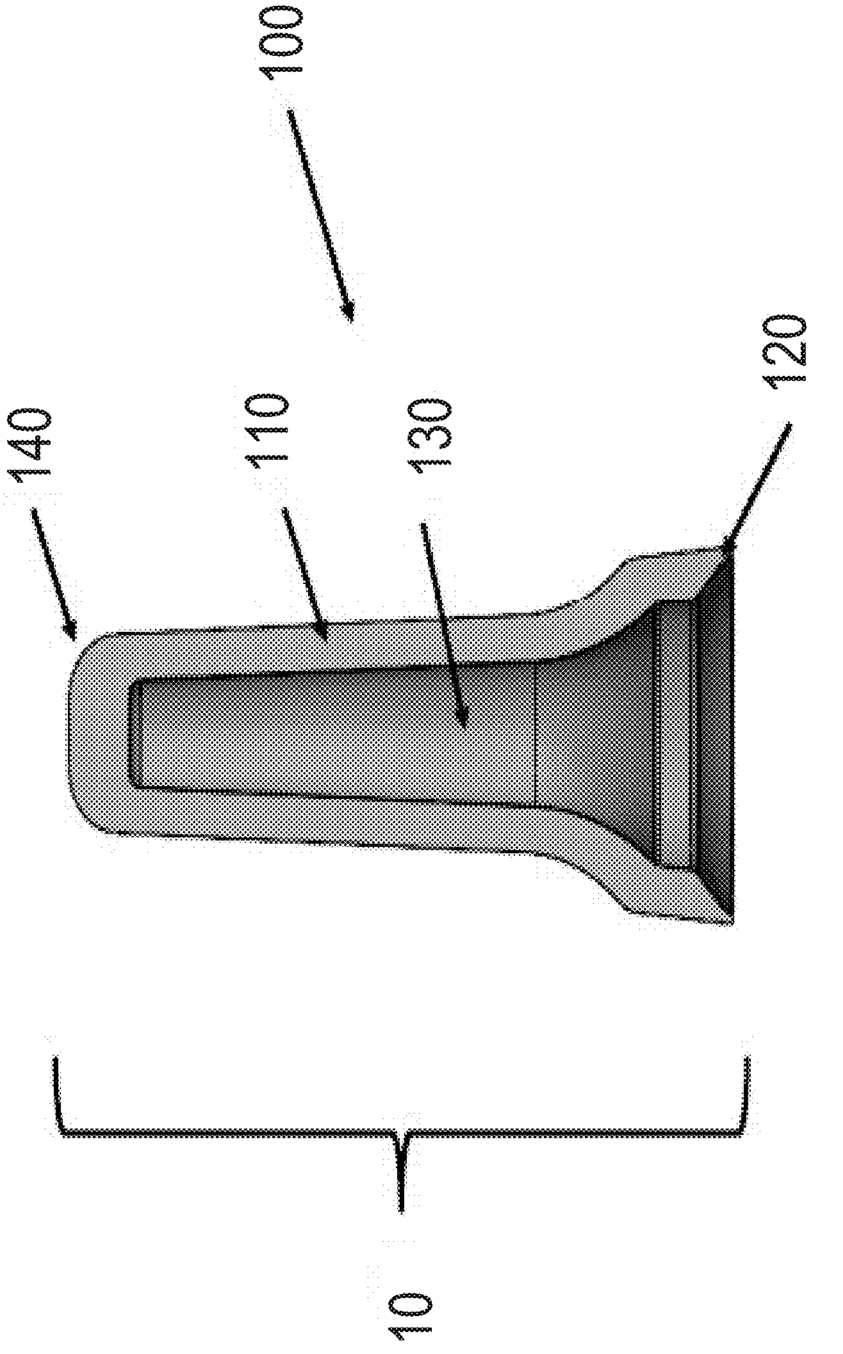
FIG. 11 is a cross-sectional view of a cornea-protecting device according to certain embodiments described herein.

Referring to FIG. 11, in some embodiments, the member of the cornea-protecting device 10 that provides suction force comprises a suction cup 100 comprising one or more curved round walls 110, wherein the diameter of the wall gradually decreases until it reaches a tip 140, and wherein the suction cup 100 comprises an opening surface 120 that is configured to contact the ocular surface and enclose the perimeter of the cornea. In some embodiments, the cornea-protecting device comprises an internal cavity 130 and is configured so that when the one or more curved walls 110 is squeezed or pinched, air is ejected from the internal cavity 130 and after the opening surface of the suction cup 120 is placed on the ocular surface, the pinching or squeezing force on the one or more curved walls 110 is released, resulting in a vacuum or partial vacuum being formed within the internal cavity 130, which causes the suction cup to adhere to the ocular surface and seal off the cornea enclosed by the opening surface 120 of the suction cup. In certain embodiments, the one or more curved walls 110 and/or the entirety of the cornea protecting device 10 comprise a thermally insulating material to further protect the cornea from lateral heat diffusion from the surrounding environment, including if cold slurry has been applied to the sclera adjacent to the cornea. In some embodiments, the evacuated internal cavity 130 that may comprise a partial or complete vacuum provides additional thermal protection to the enclosed cornea from the surrounding environment by retarding the conduction, convection and radiation heat transfer from the surrounding environment. In some embodiments, the one or more curved walls 110 and/or the entirety of the cornea-protecting device 10 comprise a nonporous material having low thermal conductivity such as polymers, polyvinyl chloride (PVC), neoprene, polyethylene (PE), polytetrafluorethylene (PTFE), silicone, ethylene propylene diene monomer rubber (EPDM), elastomeric materials, silicone, thermoplastic elastomer (TPE), thermoplastic polyurethane (TPU), etc.

In some embodiments, the one or more curved walls 110 and/or entirety of the cornea-protecting device 10 comprises one or more layers of low thermal conductivity material. In certain embodiments, the thermal conductive material is selected from the group consisting of polyurethane (PU) foam, polyisocyanurate foam, extruded polystyrene foam (XPS), expanded polystyrene foam (EPS), aerogel, silicone, EPDM, elastomeric materials, etc.

In some embodiments, the member that provides suction force (e.g., suction cup) and/or one or more of the curved walls 110 of the cornea-protecting device provides high thermal resistance to retard the heat transfer rate from the surrounding cold slurry to the cornea. In some embodiments, the suction cup and/or one or more walls of the cornea-protecting device comprises optically transparent or semi-optically transparent material such as optically clear silicone. In some embodiments, the suction cup and/or one or more walls of the cornea-protecting device comprises optically opaque material such as silicone and dyed elastomeric materials.

In some embodiments, the member that provides suction force (e.g., suction cup) comprises the following design parameters: suction area/diameter, wall thickness, vertical height, etc.

In some embodiments, when the member that provides suction force (e.g., suction cup) of the cornea-protecting device is held in place by suction force, a vacuum or partial vacuum is formed between the one or more walls 110 in the internal cavity 130 of the cornea protector. This vacuum or partial vacuum provides thermal protection for the cornea from its surroundings, including the deposited cold slurry that may contact the outside walls of the cornea-protecting device.

Figure 12:
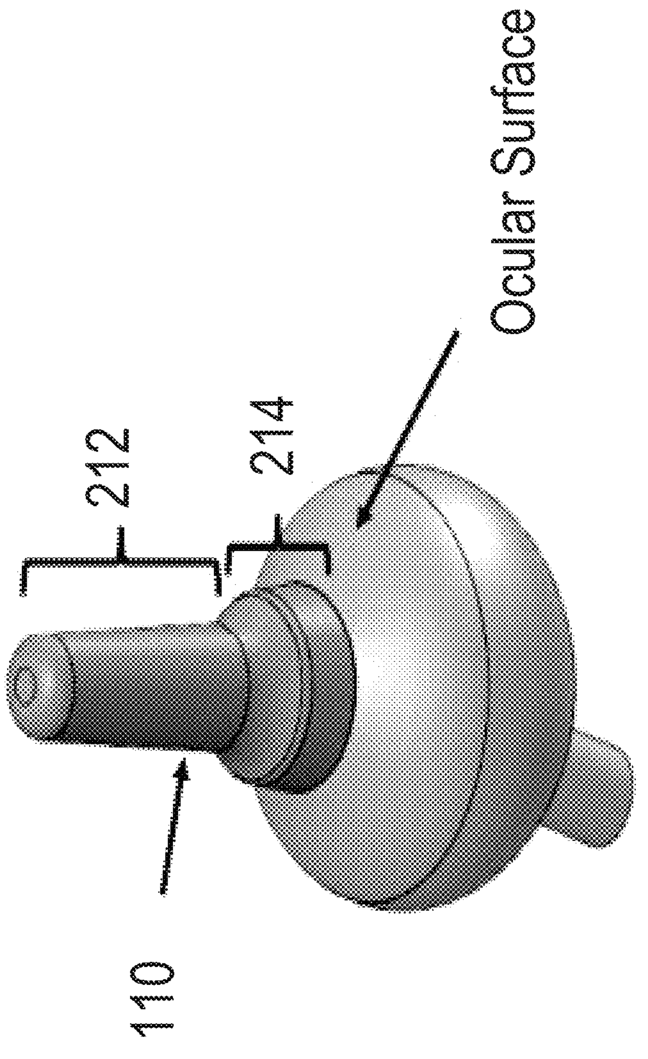
FIG. 12 is a perspective view of an exemplary cornea-protecting device, with the cornea-protecting device placed on the ocular surface around the perimeter of the cornea to enclose and seal the cornea according to certain embodiments described herein.

Referring to FIG. 12, in some embodiments, the cornea-protecting device comprises an upper portion 212 for activating and deactivating the suction force. The suction force may be activated by squeezing and releasing the walls of cornea-protecting device in the area of the upper portion 212. In certain embodiments, the cornea-protecting device comprises a bottom element 214 forming a member that provides suction force (e.g., suction cup) with an opening that positions on the ocular surface to cover the cornea and when held in place by suction force creates a barrier between the perimeter of the cornea and sclera.

In some embodiments, the member that provides suction force (e.g., suction cup) is used to protect the cornea from its surroundings, including any cold slurry applied to the surface of the eye, by first pinching or squeezing the top element 212 of the device to activate the member that provides suction force (e.g., suction cup), then positioning the bottom element 214 on the surface of the eye so that the edges of the device touching the eye encircle the outer edge or perimeter of the cornea, and then release the top element 212 to activate the suction force so that the member that provides suction force adheres to the ocular surface. The suction force ensures that the device remains in place covering and protecting the cornea. The cornea-protecting device may then be removed from the surface of the eye by pinching or squeezing the top element 212 to deactivate the suction force and then carefully removing the device from the surface of the eye. In some embodiments, the member that provides suction force (e.g., suction cup) is used to protect the cornea from its surroundings, including any cold slurry applied to the surface of the eye, by first positioning the bottom element 214 on the surface of the eye so that the edges of the device touching the eye encircle the outer edge or perimeter of the cornea, then pinching/squeezing and releasing the top element 212 of the device so as to push the air out of the member (e.g., suction cup) and create a low-level vacuum inside the member that holds the member in place.

Figure 13A:
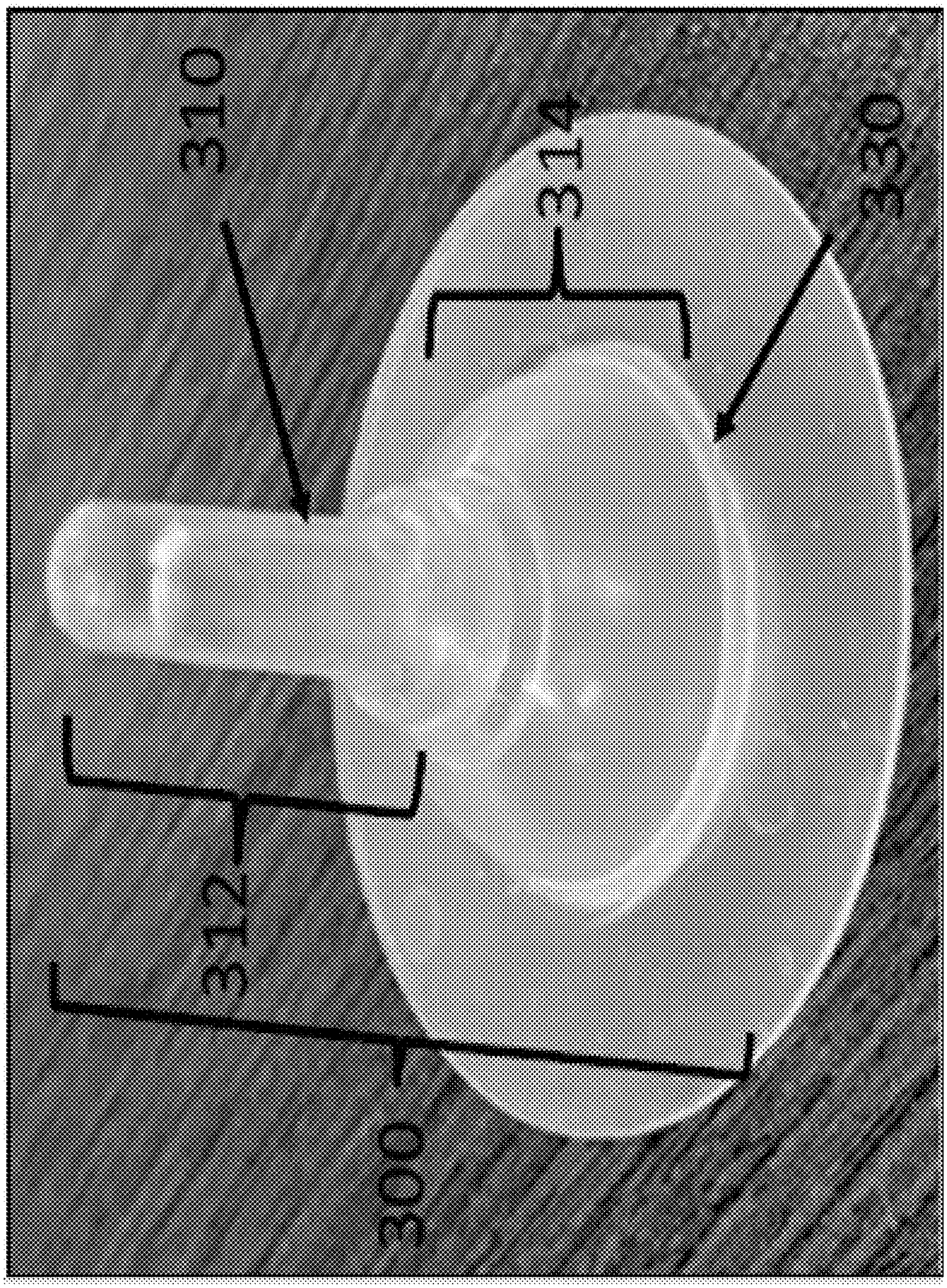
FIGS. 13A and 13B show an exemplary cornea-protecting device as described herein.
Figure 13B:

Referring to FIGS. 13A and 13B, a cornea-protecting device 300 and its application to seal around the perimeter of the cornea is shown. The cornea protecting device 300 comprises one or more walls 310, an opening surface 330 that contacts the target surface (e.g., ocular surface) and encircles the perimeter of an area on the target surface (e.g., cornea), and an internal cavity that is held under a vacuum or partial vacuum when the suction force of the device is activated. In certain embodiments, the one or more walls 310 comprises a top element 312 and a bottom element 314, which is shaped as a cup. The bottom element 314 comprises an opening surface 330 that is positioned over the perimeter of the target area (e.g., cornea) as shown in FIG. 13B and the top element 312 is squeezed or pinched to expel air from the internal cavity and thus create suction (i.e., vacuum) force within the cavity that causes the cornea-protecting device to be held in place on the target surface (e.g., the area over the cornea as shown in FIG. 13B).

Contact Lens for Protecting Cornea

In some embodiments, aspects of the invention are directed to using a contact lens for protecting the cornea, both physically and thermally, during cold slurry treatment. Prior to application of the cold slurry to the eye, a contact lens may be placed on the cornea. The contact lens may serve both as a physical and a thermal barrier layer between the cornea and surrounding cold slurry. Potential advantages of using a contact lens for protecting the cornea in a cold slurry treatment include ease of use and patient familiarity with the product, helping reduce anxiety during the treatment. However, a few challenges with using a contact lens may exist: 1) the contact lens may shift in position during the treatment, exposing the cornea to the slurry, 2) the slurry may still diffuse laterally, i.e., around the corner of the lens to enter from the sclera and into the cornea, 3) typical contact lenses are porous, potentially allowing for surrounding slurry to find its way into the cornea, and 4) the contact lens needs to be thin to be placed over the corneal surface, limiting the thermal resistance provided by the contact lens from the surrounding cold slurry.

In some embodiments, a contact lens may be used that comprises material with low thermal conductivity but which still allows for sufficient suction force, for example, polymethyl methacrylate (PMMA), silicone, hydrogel, etc.

Devices for Protecting an Eyelid

If the eyelid of the subject is contacted with the slurry described herein, subzero temperature and duration of the cold slurry contacting the eyelid can potentially cause inflammation and/or physical damage to the eyelid. Described herein are eyelid-protecting devices that can be used alone or in conjunction with cold slurry treatment to physically and thermally separate the eyelid from materials, such as the cold slurry, that have been applied to the ocular surface. The eyelid-protecting devices are generally shaped to fit between the upper and lower eyelids of a patient and act as a physical and thermal barrier between the eyelid and the material (e.g., cold slurry) deposited on the ocular surface. In some embodiments, the eyelid-protecting device also serves as a speculum to keep the eye open during treatment.

Figure 14A:
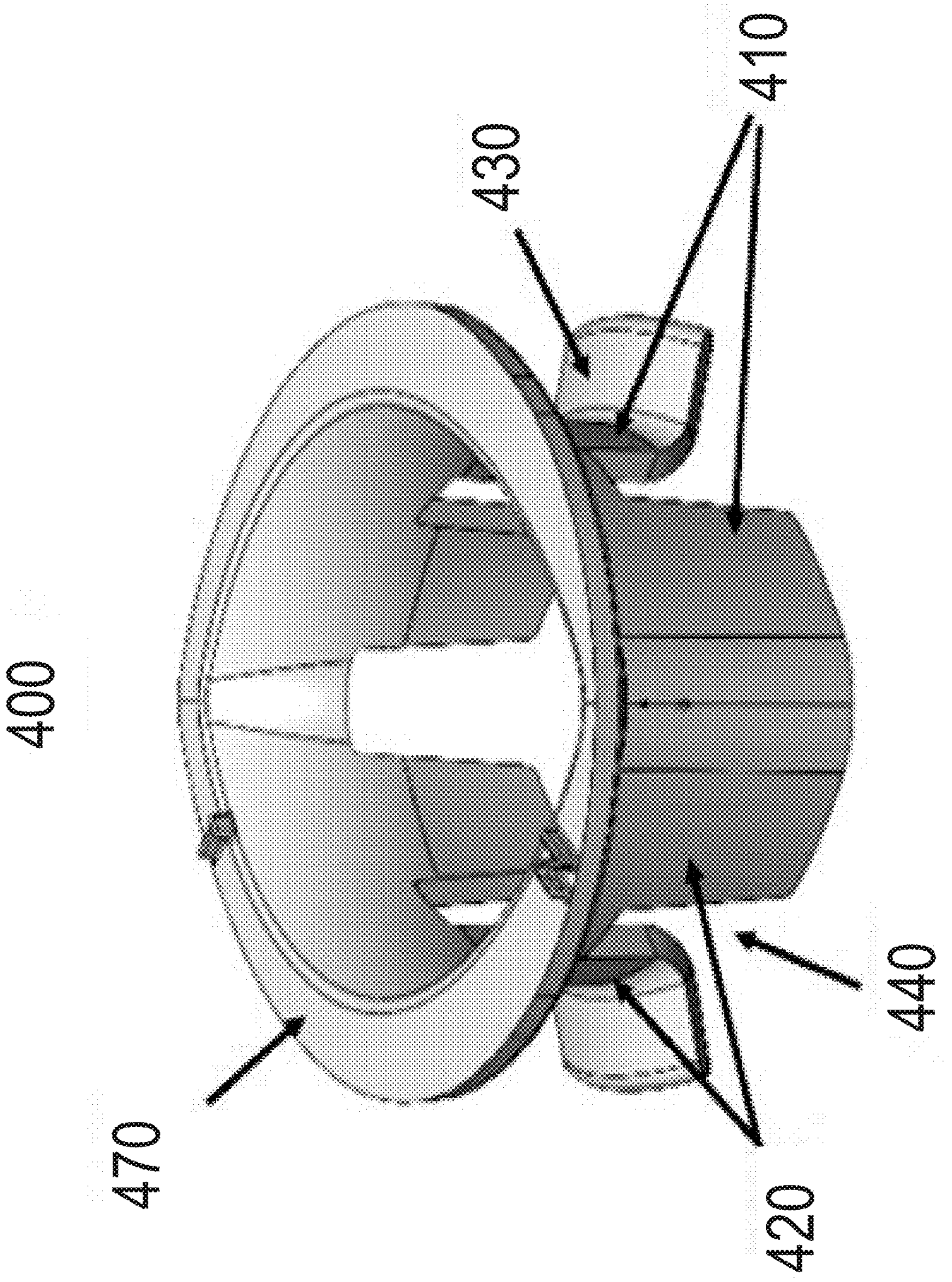
FIGS. 14A and 14B are perspective views of exemplary eyelid protector devices according to certain embodiments described herein.
Figure 14B:
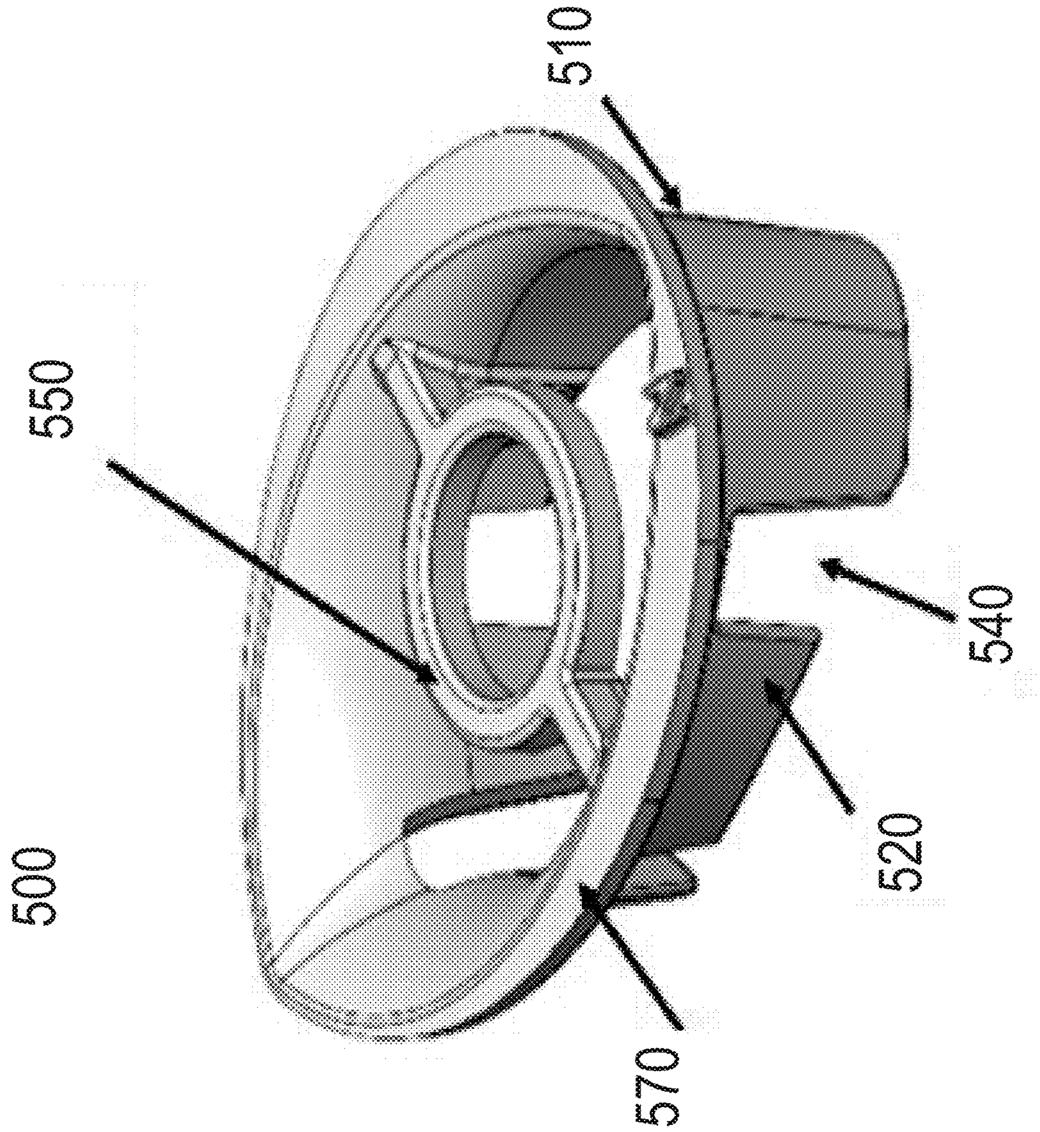

Referring to FIGS. 14A and 14B, in some embodiments, the eyelid-protecting device 400, 500 comprises a surface 410, 510 that contacts the upper eyelid and a surface 420, 520 that contacts the lower eyelid. In certain embodiments, one or both of surfaces 410, 510 and 420, 520 are curved (e.g., convex) in shape in order to better fit the contours of the eyelid and eye. In some embodiments, one or more of surfaces 410, 510 and 420, 520 of the eyelid-protecting device comprises a member (e.g., platform) 470, 570 to assist the practitioner in handling and manipulating the device, for example, for insertion into and retrieval from the eye. In certain embodiments, one or more of the surfaces 410, 510 and 420, 520 of the eyelid protecting device comprises one or more structures 430 that serve as a speculum to keep the eyelids opening while the device is inserted into the eye. In some embodiments, the eyelid-protecting device comprises an opening in between or encircled about by the surfaces 410, 510, and 420, 520 that fits over the surface of the eye. The size of the opening can vary depending on the size of the eye of the subject. In certain embodiments, the eyelid-protecting device comprises a single continuous component comprising both surfaces 410, 510 and 420, 520. In some embodiments, the eyelid-protecting device comprises more than one component in which surfaces 410, 510 and 420, 520 are separate components that can be reversibly attached to one another to form the complete device. In some embodiments, one or more of the surface components 410, 510 and 420, 520 of the eyelid protector device comprises segments of curvilinear links that can be moved relative to each other to adjust the size of the opening in the device to accommodate eyelids of various shapes and sizes. In certain embodiments, the distances across the opening of the eyelid-protecting device between or encircled by surfaces 410, 510 and 420, 520 can be adjusted to accommodate eyelids and eyes of various shapes and sizes.

The size of each aspect of the eyelid-protecting device can be adjusted to provide a device to accommodate eyelids and eyes of various shapes and sizes. In some embodiments, the eyelid-protecting device comprises dimensions that allow opening the eyelids in a range of 0-20.83 mm or 17.25-20.83 mm. In some embodiments, the depth of the protrusions of the eyelid-protecting device that are inserted under the eyelids ranges between 2.54-5.85 mm. In some embodiments, the eyelid-protecting device comprises one or more types of plastic, extruded plastic, silicone, EPDM, etc. In some embodiments, the eyelid-protecting device comprises one or more low thermally conductive materials, for example, silicone and EPDM. In some embodiments, the eyelid-protecting device comprises one or more porous materials, such as open cell foams, PVA, etc., that is both a thermal insulator and a wicking material.

In some embodiments, the eyelid-protecting device is configured to allow melted, i.e., liquid or less viscous, slurry to drain away from the surface of the eye. For example, in certain embodiments the eyelid-protecting device comprises gaps or channels 440, 540 in one or more of the surfaces 410, 510, and 420, 520, that allow the melted slurry to drain away from the surface of the eye. Removing the warmer, melted slurry from the surface of the eye is advantageous in certain embodiments as it allows a fresh batch of cold slurry to be supplied to the ocular surface while the eyelid protector remains in place. Such removal of melted slurry during the treatment is desired in certain embodiments to ensure that the ocular surface remains in contact with the ice crystal-containing slurry that is at the desired temperature (as opposed to being covered by the warmer melted slurry), improving the efficiency and effectiveness of the treatment. In some embodiments, the eyelid-protecting device comprises a wicking structure and/or wicking material that assists in removing the melted slurry from the ocular surface. Examples of wicking material and structures that can be incorporated into the eyelid-protecting device include, but are not limited to PVA, open cell foam materials, etc.

Figure 15A:
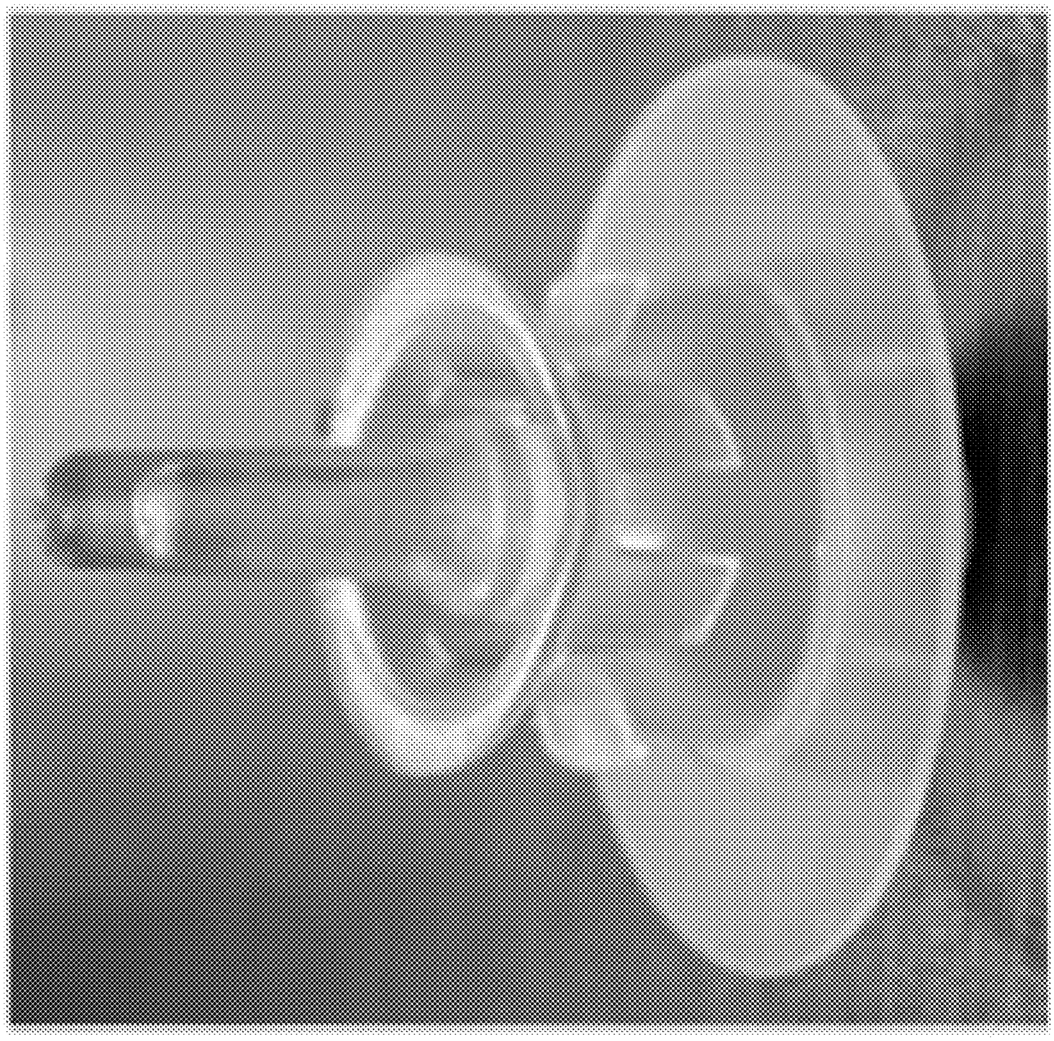
FIGS. 15A and 15B show exemplary eyelid protector devices in conjunction with exemplary cornea-protecting devices according to certain embodiments described herein.
Figure 15B:
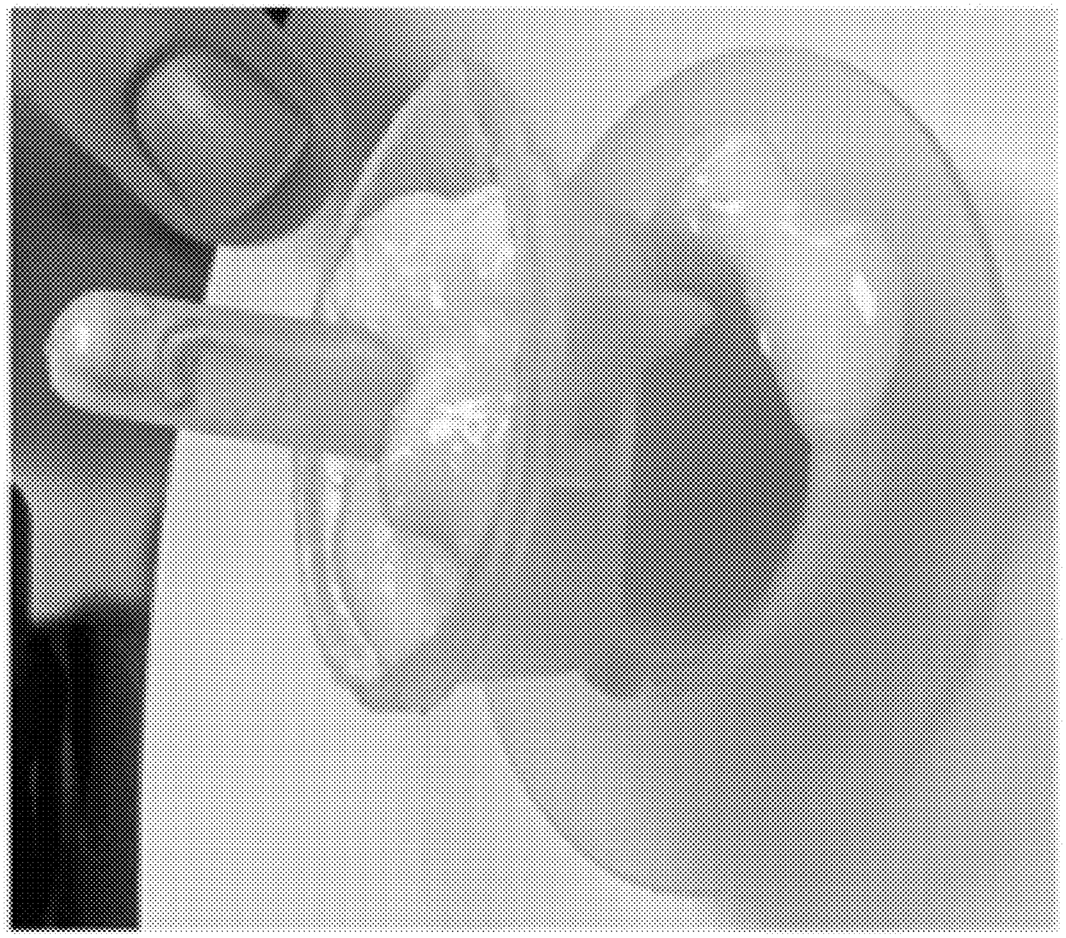

Referring to FIG. 14B, in some embodiments, the eyelid-protecting device comprises a structure, for example, feature 550, for receiving and holding a cornea-protecting device, such as the cornea-protecting devices described herein and shown, for example, in FIGS. 11-13. Such an eyelid-protecting device in conjunction with a cornea-protecting device can be used to protect both the eyelid and cornea, for example, while applying the cold slurries described herein to the surface of the eye. Examples of eyelid-protecting devices and cornea-protecting devices used in conjunction are shown in FIGS. 15A and 15B.

Kits

Figure 16:
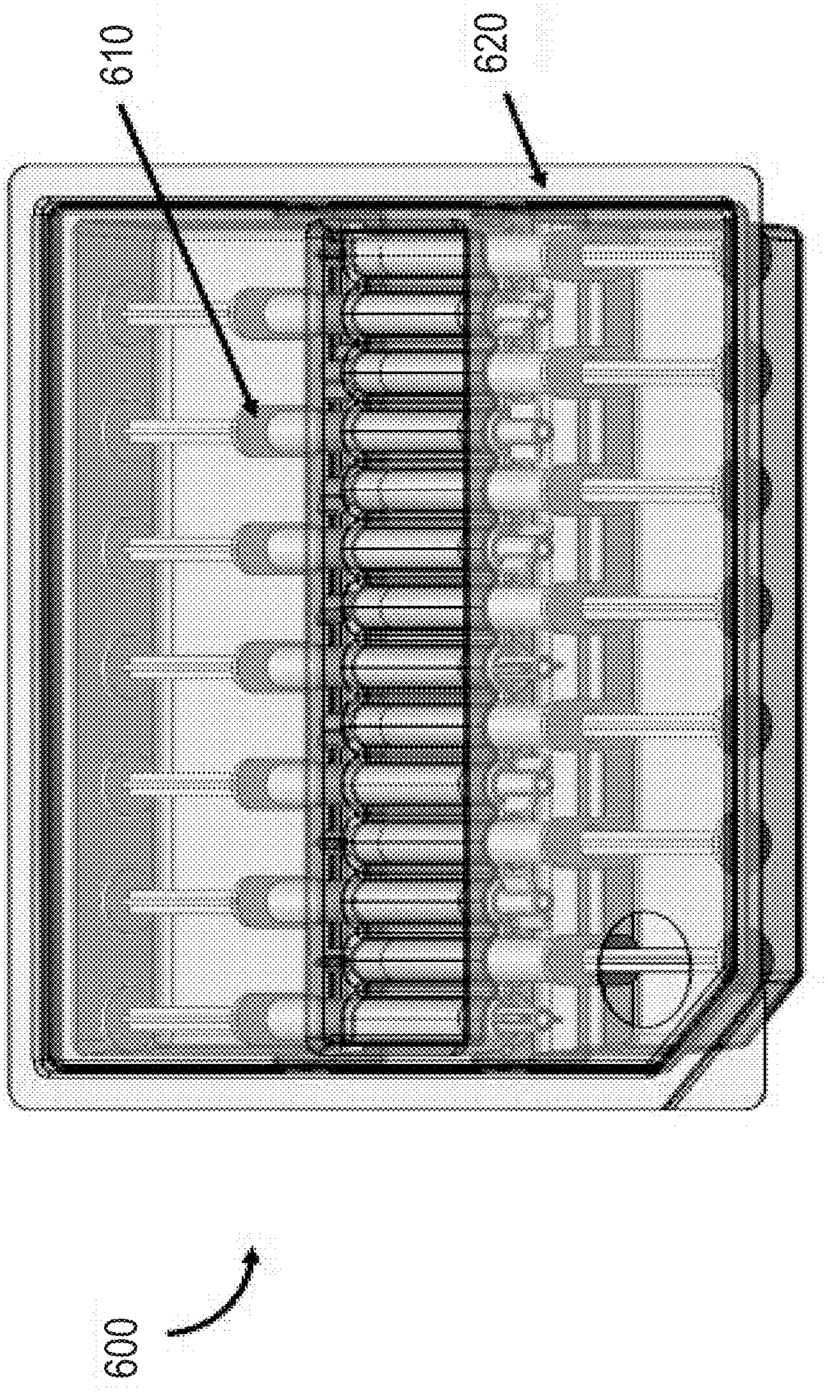
FIG. 16 shows an exemplary kit comprising multiple syringes containing cold slurry according to certain embodiments described herein.

For a more effective cold slurry treatment, the ocular surface should be maintained at a subzero temperature during the entire duration of the treatment. In certain situations, a cold slurry that is topically administered will warm above the critical temperature and melt while on the ocular surface before the treatment is complete, necessitating additional doses to be administered to maintain the desired subzero temperature of the ocular surface. Accordingly, described herein are kits for providing a plurality of cold slurry doses that allows for a treatment comprising multiple administrations of slurry to maintain the ocular surface at a subzero temperature throughout the course of treatment. Referring to FIG. 16, in some embodiments, the kit 600 comprises multiple syringes 610 prefilled with the slurry. In some embodiments, the kit comprises an outer packaging 620 that contains the multiple syringes 610. In some embodiments, the outer packaging 620 is configured to store, seal, and provide thermal and moisture protection for the multiple syringes 610. In certain embodiments, the kit 600 comprises at least two syringes prefilled with the slurry. In some embodiments, the kit 600 comprises from 2-20, from 2-15, from 2-10, or from 2-5 syringes prefilled with slurry. In some embodiments, the kit 600 comprises one syringe prefilled with slurry. The number of syringes in the kit can vary depending on various factors, including the duration of the planned treatment, the size of the eye, and the ability to store kits of different sizes (e.g., the size of freezer available.) The amount of slurry in each syringe can also vary (e.g., 1-20 ml) depending on the same sort of factors listed above relating to specifics of the desired treatment and storage resources. Prior to and during use in a cold slurry procedure, the kit can be stored in a freezer to ensure that the cold slurry in each syringe starts and substantially remains at the desired temperature (e.g., subzero temperature) during the procedure. Such kits may also help promote proper use and effectiveness of the cold slurry treatment because the clinician is more informed about how many doses and at what time interval a new dose is to be administered to the treatment area.

In some embodiments, the kit 600 comprises thermal packaging that is configured to maintain the cold slurry at a subzero temperature for a desired period after the kit is taken out of the freezer and placed in ambient temperature conditions (e.g., during transport or in advance of near term use). This is particularly useful where a freezer is not available during the cold slurry procedure, such as in remote, underdeveloped regions. In some embodiments, the thermal packaging of the kit comprises phase change materials, thermal insulation, reflective barrier, reflective foils, polystyrene foam, or combinations thereof.

In some embodiments, the kit comprises one or more empty syringes and a separate container with slurry. Prior to the procedure, one or more of the empty syringes may be filled with cold slurry by drawing slurry from the container. In certain embodiments, the slurry may be drawn into the one or more empty syringes under ambient temperature conditions where liquid slurry can be easily drawn by the syringe. In such embodiments, the filled syringes can be returned inside the kit and placed and/or stored in a freezer prior to use.

In some embodiments, the kit comprises an outer packaging made of air and/or moisture barriers, e.g., metallized polymeric films, thin metal films, polymeric films, expanded polystyrene foam, etc. to impart long shelf life to the slurry. In certain embodiments, the outer package seals the kit to provide a degree of protection against, for example, potential contamination, temperature changes, and/or other environmental conditions.

Methods for making and shipping cold slurry formulations have been described previously, for example in U.S. Pat. Nos. 11,241,330; 11,564,830; 11,471,401; U.S. patent application Ser. No. 18/358,795 (filed on Jul. 25, 2023, not yet published); International Application No. PCT/US2022/33095 (Publication No. WO/2022/261494); and International Application No. PCT/US2023/62443 (Publication No. WO/2023/154902); which are hereby incorporated by reference in their entireties. In certain embodiments, the kit comprises a prefilled syringe, wherein the syringe is prefilled with a composition according to U.S. Pat. No. 11,471,401; International Application No. PCT/US2022/33095 (Publication No. WO/2022/261494); or International Application No. PCT/US2023/62443 (Publication No. WO/2023/154902); which are hereby incorporated by reference in their entireties. In certain embodiments, the kit is compatible with manufacturing systems and methods described previously, such as in U.S. Pat. Nos. 11,241,330 and 11,564,830, which are hereby incorporated by reference in their entireties. In certain embodiments, the kit comprises at least one prefilled syringe, wherein the kit may be shipped, the contents of the syringe may be transformed into a slurry, and the slurry may be administered according to the disclosure of U.S. Pat. No. 11,471,401, which is hereby incorporated by reference in its entirety.

Self-Contained Cooling Devices

In some embodiments, aspects of the invention are directed to a self-contained cooling device that allows thermal energy transfer from a target surface (e.g., ocular surface) using the cold slurry treatment. In certain embodiments, the self-contained cooling device is used for the purposes of cryoneurolysis. In some embodiments, such a self-contained cooling device is configured to protect the cornea, eyelids, and potentially other sensitive structures (e.g., tissues, skin), from subzero temperatures required during the cryoneurolysis procedure and any physical damage potentially caused during application of the treatment.

In some embodiments, aspects of the invention are directed to a self-contained cooling device comprising a vessel containing a thermal mass (e.g., a liquid, solid, or cold slurry formulation) with a freezing point lower than that of water. In some embodiments, such a device may be shipped and stored within a sterile package at ambient temperature or in a standard freezer. In some embodiments, such package is frozen prior to use. In some embodiments, when ready to use, the device is removed from the freezer and its package (e.g., a sterile barrier) and applied to the target ocular surface to achieve cryoneurolysis. In some embodiments, the device is discarded after use. In some embodiments, the liquid or cold slurry formulation is sealed within the vessel so that it cannot come in direct contact and thus cause any damage to the target ocular surface or surrounding tissues and body parts (e.g., cornea, eyelid, skin).

In certain embodiments, the self-contained cooling device comprises a thermal mass (e.g., a liquid, solid, or cold slurry formulation). In certain embodiments, the thermal mass is contained inside of a heat exchanger. In certain embodiments, the thermal mass comprises a formulation of about 20% wt/wt glycerol in water (e.g., purified water).

In certain aspects, self-contained cooling devices according to the present disclosure can be sterilized. In certain embodiments, the self-contained cooling device is placed into a packaging after being sterilized. In certain embodiments, the self-contained cooling device is sterilized after being placed within the packaging. In certain embodiments, the self-contained cooling device is sterilized before shipping. In certain embodiments, the self-contained cooling device and, optionally, the packaging are sterilized, shipped, received at a point of care, placed into a freezer, and then opened for use, thereby maintaining sterility throughout preparation and shipment prior to a procedure.

In some embodiments, the self-contained cooling device is configured to administer a cryoneurolysis procedure to provide long-term ocular pain relief. In some embodiments, such self-contained cooling device is intended to be used by clinicians or by patients in an out-of-clinic setting without a need for a physician. In some embodiments, the self-contained cooling device is used in combination with an eyelid protective device to protect a subject's eyelids from damage from the cooling treatment. In some embodiments, the self-contained cooling device is formed to balance on a subject's eye while the subject is in a supine position.

In some embodiments, aspects of the invention are directed to a self-contained cooling device capable of maintaining the ocular surface at a subzero temperature. In referring to FIG. 17, in certain embodiments, the self-contained device 700 comprises a target (e.g., ocular) surface interface 710 that is configured to contact the desired portion of the target (e.g., ocular) surface and act as an effective thermal interface that efficiently transfers thermal energy from the ocular surface to a thermal mass to enable cooling and maintenance of the ocular surface at the desired subzero temperature for prolonged hypesthesia. In some embodiments, where the thermal mass is used to carry away thermal energy from the ocular surface, the ocular surface interface 710 of the device acts as a physical barrier between the ocular surface and the thermal mass. In some embodiments, the thermal mass comprises a cold slurry, solid ice, or a liquid formulation. Some of the benefits of such self-contained cooling devices are that the biocompatibility or flowability of the thermal mass (e.g., cold slurry, liquid formulation) are not a concern because the thermal mass is not in direct physical contact with the ocular surface, which may result in a more streamlined and simpler procedure.

Figures 17A, 17B:
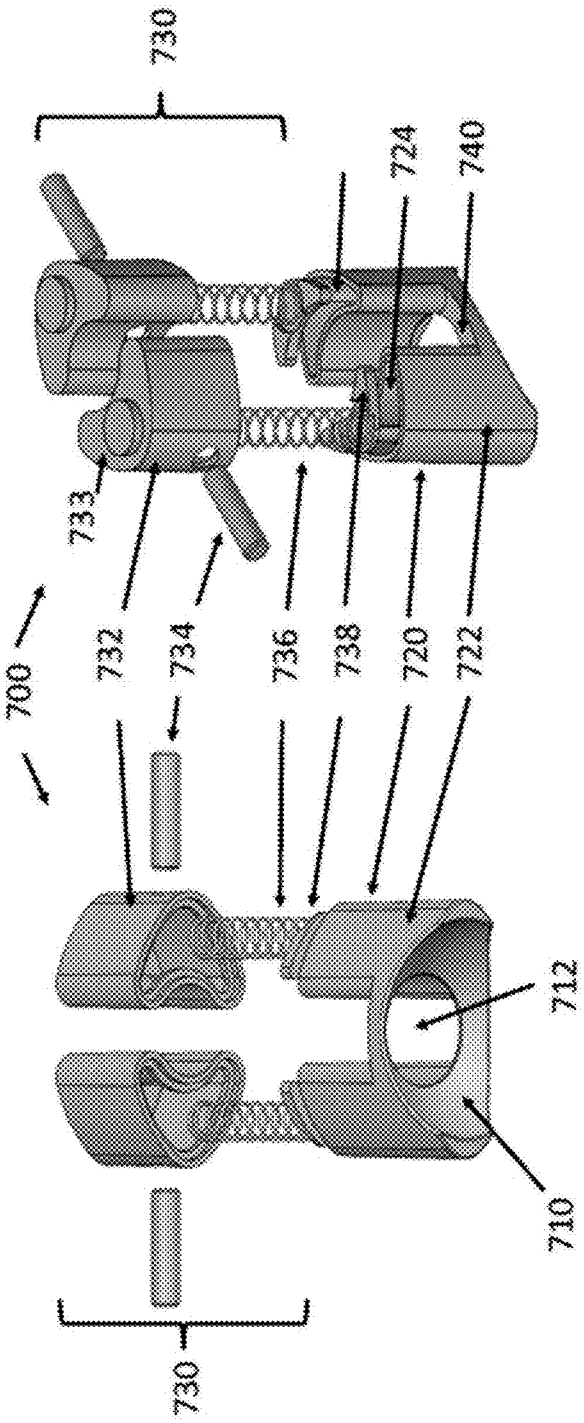
FIGS. 17A and 17B show a front perspective view (17A) and a perspective view (17B) of a self-contained eye cooling device according to certain embodiments described herein.

In some embodiments, the self-contained cooling device comprises a formulation chamber or reservoir 720 for holding a thermal mass (e.g., liquid or slurry formulation), which may have a freezing temperature lower than that of water, such as the cold slurries described herein. In certain embodiments, the formulation may be a liquid that can be cooled or frozen within the chamber or reservoir 720 of the device prior to use, for example, by placing the entire device or the reservoir or chamber 720 portion of the device containing the formulation inside a standard freezer. As shown in FIGS. 17A and 17B, the ocular surface interface 710 can be either an integral part of the reservoir or chamber 720 or be attached to the bottom side of the reservoir or chamber 720. In such configurations, the thermal energy from the ocular surface is dissipated via the ocular surface interface 710 and into the formulation within the chamber or reservoir 720.

In certain embodiments, the ocular (i.e., target) surface interface 710 is curved (e.g., concave) in shape in order to better fit the contours of the ocular surface. In some embodiments, the ocular surface interface 710 has an opening or hole (e.g., circular, rectangular, elliptical, irregular size opening) 712 that is configured to be aligned over a target area of the eye (e.g., the cornea) to prevent a direct cooling of the cornea via the ocular surface interface 710 and through the cold slurry in the chamber 720.

In certain embodiments, the formulation within the chamber 720 utilizes the latent heat of a phase change (e.g., sold-liquid phase transformation) to maintain sub-zero temperature on the target ocular surface for a predetermined duration of time (i.e., volume-controlled amount of thermal energy transfer).

In some embodiments, the ocular (i.e., target) surface interface 710 comprises one or more high thermally conductive materials such as Al, Cu, Au, Ni, stainless steel, metal alloys, thermally conductive plastics including metal impregnated polyimide, or combinations thereof. In some embodiments, the ocular surface interface 710 comprises one or more encapsulated phase change materials (PCM), shape-stabilized PCMs, or combinations thereof. In some embodiments, the surface of the ocular surface interface 710 that contacts the ocular surface comprises a non-stick coating, e.g., PTFE, hard coatings, anodized coatings, diamond-like-coatings (DLC). In some embodiments, the surface of the ocular surface interface 710 that contacts the ocular surface comprises a hydrophobic surface coatings including nanocoatings and composite materials. In some embodiments, the surface of the ocular surface interface 710 that contacts the ocular surface comprises a surface coating that protects the ocular surface from adhering to the frozen ocular surface interface 710 such as hard coatings, anodized coatings, DLC, nanocoatings, composite materials, PTFE, etc. In some embodiments, the surface of the ocular surface interface 710 that contacts the ocular surface comprises geometric design features (e.g., hierarchical micro/nano structures and surfaces, bioinspired hydrophobic surface patterns) that protects the ocular surface from adhering to the frozen ocular surface interface 710. In some embodiments, the ocular surface interface 710 that contacts the ocular surface comprises a thin film of material.

In some embodiments, the surface of the ocular surface interface 710 that contacts the ocular surface comprises a hydrophilic surface coating. In some embodiments, the surface of the ocular surface interface 710 that contacts the ocular surface comprises a low surface energy material. In some embodiments, the ocular surface interface 710 comprises an embedded thermoelectric Peltier cooler. In some embodiments, the self-contained cooling device comprises one or more electromechanical systems that circulates coolant (or cold air) through the ocular surface interface 710. In some embodiments, the self-contained cooling device comprises one or more mechanical systems that delivers coolant to the ocular surface interface 710. In some embodiments, the self-contained cooling device comprises one or more mechanical systems that facilitates manual administration of coolant to the ocular surface interface.

To ensure that the target surface remains at the desired subzero temperature during the treatment, the ocular surface interface 710 should remain in contact with the portion of the formulation (e.g., frozen or slurry formulation) that is at the desired temperature within the chamber or reservoir 720. In certain embodiments, the portion of the slurry or frozen formulation in contact with the ocular surface interface 710 will start to melt as it warms due to the transfer of heat from the ocular surface to the ocular surface interface 710 and then to the formulation within the chamber or reservoir 720. For example, in embodiments in which the formulation comprises water, because liquid water is denser than ice, the melted (i.e., liquid, thawed) portion of the formulation will tend to settle down at the bottom of the chamber or reservoir 720 in contact with the ocular surface interface 710 while the more solid (e.g., ice portion) of the formulation will tend to float toward the top of the chamber or reservoir 720 and lose contact with the ocular surface interface 710, resulting in decreased heat carrying capacity of the formulation in contact with the ocular surface interface 710.

In some embodiments, the self-contained cooling device comprises a mechanism 730 for pushing down the frozen portion of the formulation within the chamber or reservoir 720 in order to maintain contact between the colder (e.g., ice or frozen) portion of the formulation and the ocular surface interface 710 in contact with the bottom of the chamber or reservoir 720 by pushing down on the formulation and forcing the colder (e.g., ice or frozen) portion of the formulation towards the bottom of the chamber or reservoir 720 where it contacts the ocular surface interface 710 and allowing the warmer portion (e.g., melted or thawed liquid) of the formulation, that has lower heat carrying capacity than the colder portion of the formulation, to flow away from the bottom of the chamber or reservoir 720 where it contacts the ocular surface interface 710 toward the top of the chamber or reservoir 720. In some embodiments, the mechanism for pushing down the formulation within the chamber or reservoir 720 in order to maintain contact between the colder (e.g., ice or frozen) portion of the formulation and the ocular surface interface comprises one or more side pins 734 that can be pushed in or out of a hollow chamber 732 above, or forming the upper portion of, the formulation chamber or reservoir 720, an extension spring 736 that has two ends operably connected or physically attached to a removable lid 733 of the hollow chamber 732 and a movable plate 738, or forming the upper portion of, the formulation chamber or reservoir 720, and the movable plate 738 that fits within an opening 724 at the top of the formulation chamber or reservoir 720 and contacts, or is in close proximity to, the walls 722 of the formulation chamber or reservoir 720. In certain embodiments, the movable plate 738 can slide up and down inside the formulation chamber or reservoir 720 while maintaining contact with or close proximity to the interior of the vertical walls 722 of the formulation chamber or reservoir 720. In some embodiments, the sliding plate comprises one or more holes to allow passage of melted liquid through the sliding plate as it moves up and down inside the chamber or reservoir 720. In certain embodiments, when the side pin 734 is pushed inside or pulled out of the hollow chamber 732, it releases the spring 736, which causes the movable plate 738 to translate downward within the formulation chamber or reservoir 720, forcing the colder (e.g., ice or frozen) portion of the formulation toward the bottom of the formulation chamber or reservoir 720 to contact the ocular surface interface 710 of the device while the warmer (e.g., melted or thawed) portion of the formulation is pushed toward the upper portion of the formulation chamber or reservoir 720. In some embodiments, the mechanism used to maintain contact between the colder (e.g., ice or frozen) portion of the formulation and the ocular surface interface 710 relies on a vacuum, gravity, capillary force, magnetism, or a combination thereof.

In some embodiments, the self-contained cooling device 700 may further comprise a structure 740 for receiving additional devices or structures, such as the eyelid-protecting devices and/or cornea-protecting devices described herein. In some embodiments, such self-contained cooling devices further comprise eyelid-protecting and cornea-protecting devices. Such self-containing cooling devices may simplify the treatments with cold slurry described herein by reducing the number of devices and associated steps that a clinician has to assemble/handle and use during the procedure.

In some embodiments, the self-contained cooling device comprises features (e.g., suction, physical locating features) that prevent the self-contained device that is mounted on the ocular surface from shifting during the treatment.

Figures 18A, 18B:
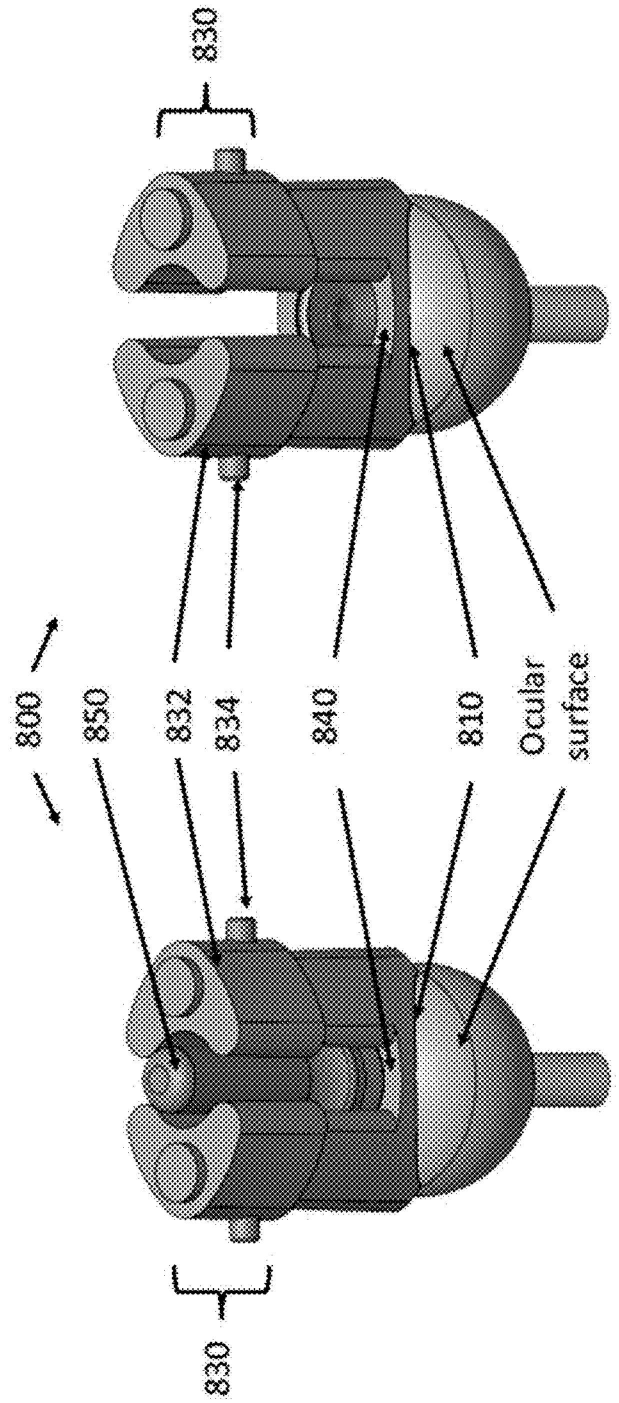
FIGS. 18A and 18B show a front perspective view of an exemplary self-contained eye cooling device with an exemplary cornea-protecting device (18A) and without an exemplary cornea-protecting device (18B) according to certain embodiments described herein.

Referring to FIGS. 18A and 18B, in certain embodiments a self-contained cooling device 800 comprises a cornea-protecting device 850 that is integrated with a structure 840 of the self-contained cooling device 800. Such a self-contained cooling device in conjunction with a cornea-protecting device can be used to protect both the cornea and target ocular surface, from coming in direct contact with the cold slurry, for example, while relying on the cold slurries described herein to affect the cooling of the target ocular surface.

In certain embodiments, when the self-contained cooling device 800 is mounted over the ocular surface so as to allow the ocular surface interface 810 to contact the desired portion of the ocular surface, the cornea protector device 850 contacts the cornea in way to protect the cornea from coming in a physical or thermal contact with any foreign material (e.g., cold slurry). In some embodiments, when the side pins 834 are pressed in toward the hollow chamber 832 to activate the mechanism 830 that enables ocular surface interface 810 to remain in contact with cold frozen slurry and allows liquid slurry to be pushed away from the ocular surface interface 810, the cornea-protecting device 840 maintains its position over the cornea.

Figure 19:
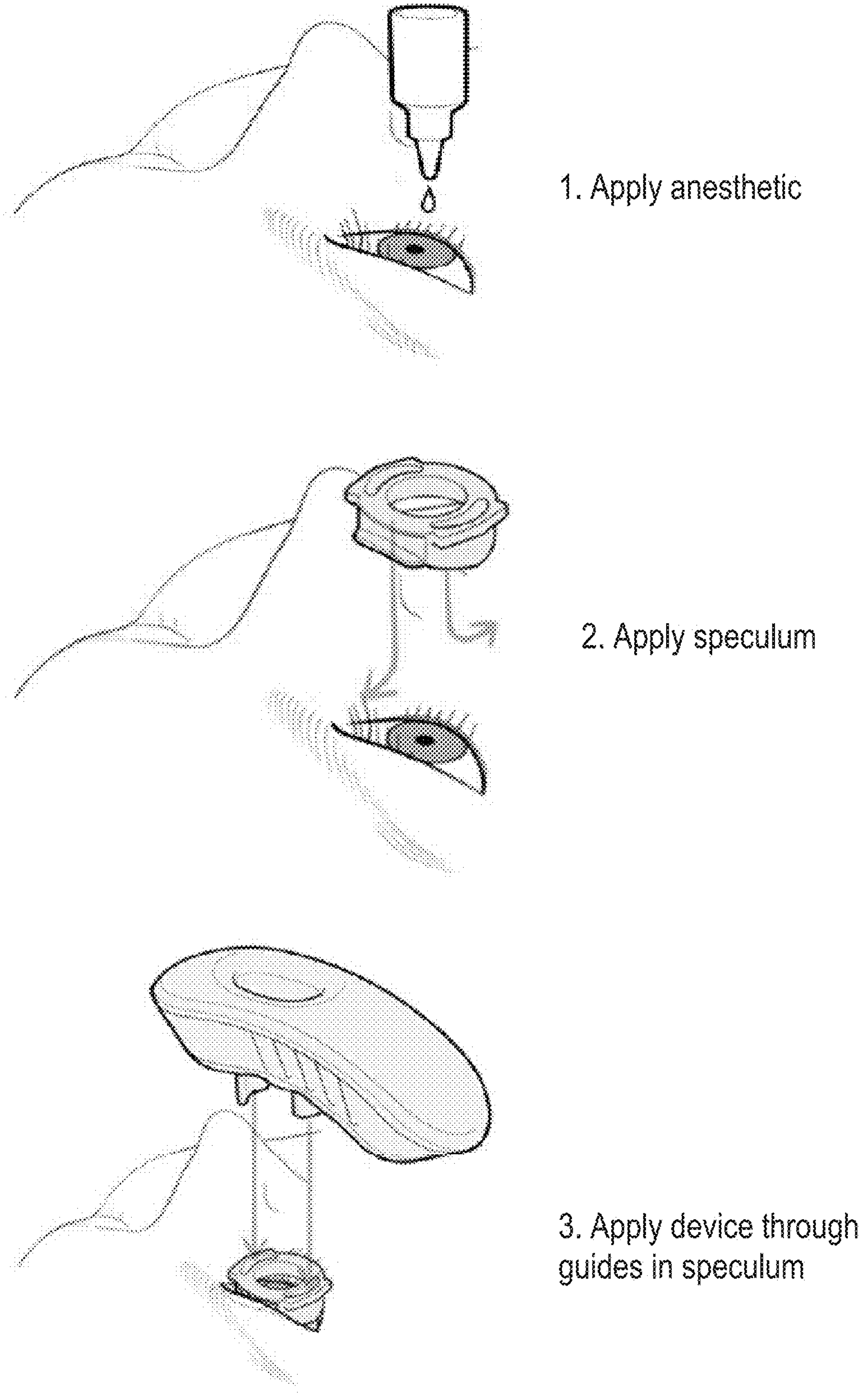
FIG. 19 shows an exemplary treatment protocol using an exemplary self-contained eye cooling device according to certain embodiments described herein.
Figure 19:
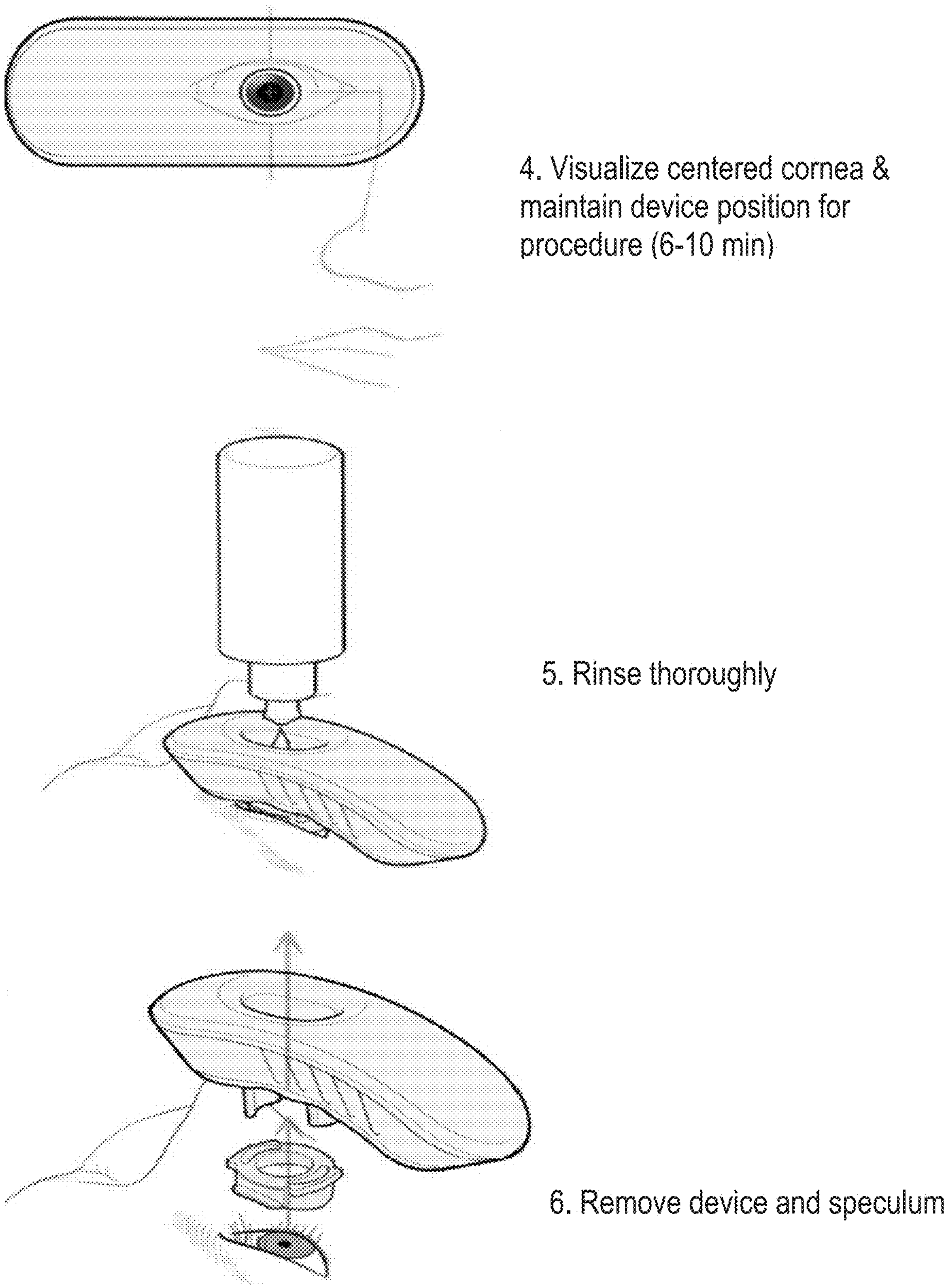
Figure 24:
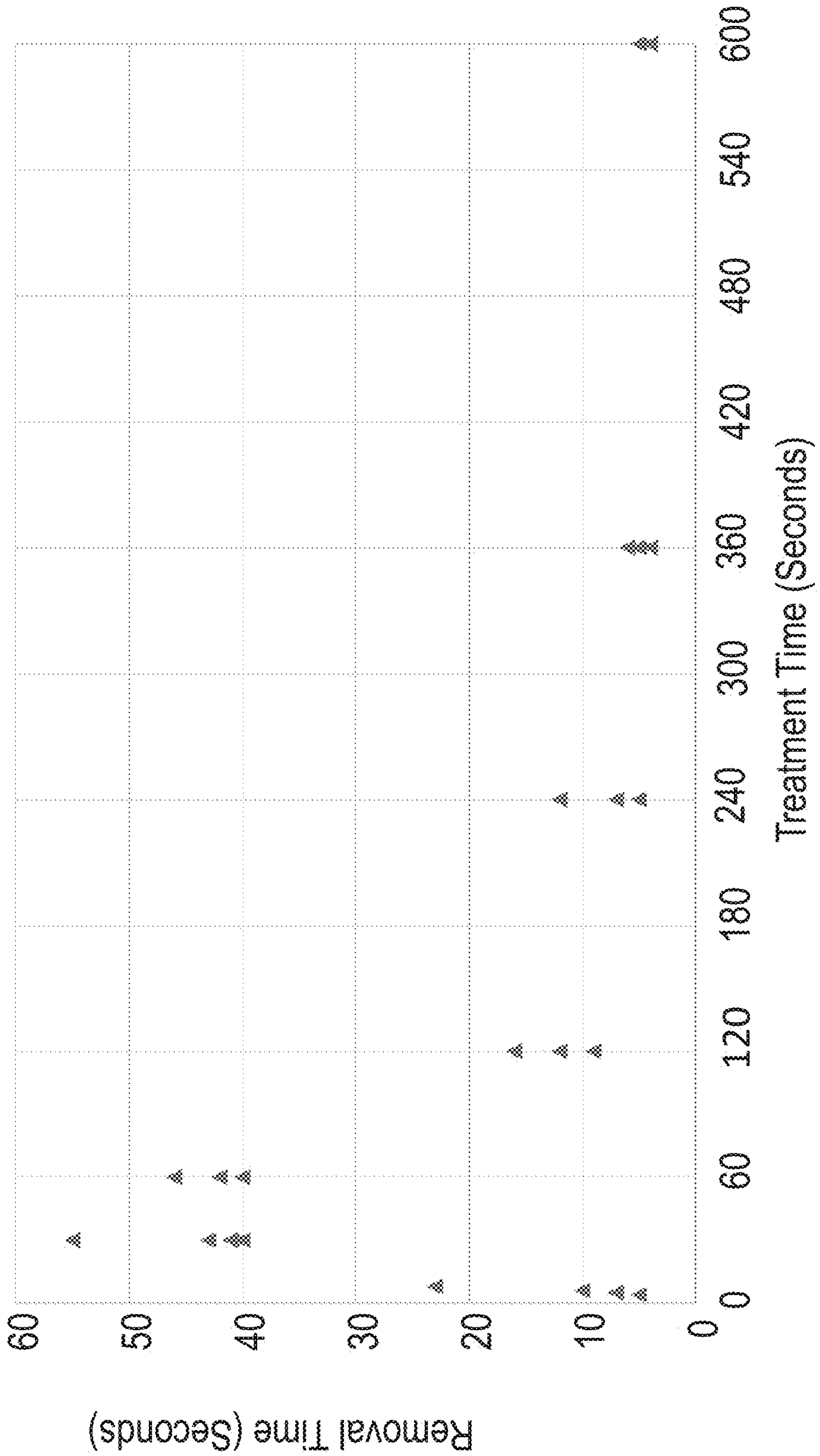
FIG. 24 is a chart plotting treatment time in seconds versus removal time in seconds for treatment with a self-contained eye cooling device according to certain embodiments described herein.

In certain embodiments, a method treating ocular surface discomfort using a self-contained cooling device is provided. An exemplary method according to certain embodiments of the present disclosure is provided in FIG. 19. First, an anesthetic may be applied to an eye of a subject. Next, an accessory (e.g., a speculum) may be placed to hold the eye open. After placing the speculum, the self-contained cooling device is placed. Optionally, the speculum includes guides configured to ensure proper placement of the self-contained cooling device. The self-contained cooling device may comprise an aperture configured to allow the clinician to visualize the cornea of the subject and to maintain proper device position. Once the self-contained cooling device contacts the eye of the subject, the device is allowed to remain in contact with the eye for a treatment time (e.g., between about 2 minutes and about 10 minutes). After the treatment time, the eye is rinsed (e.g., with saline) to avoid adhesion between the eye and the self-contained cooling device following treatment. After rinsing, the device and speculum are removed. FIG. 24 provides a chart showing treatment time versus removal time following treatment using methods according to the present disclosure.

In certain embodiments, the self-contained cooling device achieves cooling of a target surface by conduction. In certain embodiments, the self-contained cooling device first contacts a target surface, e.g., a sclera, and conducts heat away from the target surface into the device, e.g., into a target surface interface and into a heat exchanger, and finally from the heat exchanger into a thermal mass (e.g., liquid, solid, or partially solid cold slurry formulation), wherein the latent heat of fusion (e.g., solid-liquid phase transformation) allows a treatment temperature to be maintained.

In certain aspects, the self-contained cooling device is allowed to remain in contact with the eye for a treatment time. In certain embodiments, the treatment time is about 1 minute, about 2 minutes, about 3 minutes, about 4 minutes, about 5 minutes, about 6 minutes, about 7 minutes, about 8 minutes, about 9 minutes, or about 10 minutes. In certain embodiments, the treatment time is more than 10 minutes. In certain embodiments, the treatment time is about 15 minutes, about 20 minutes, about 25 minutes, about 30 minutes, about 35 minutes, about 40 minutes, about 45 minutes, about 50 minutes, about 55 minutes, about 60 minutes, or more than about 60 minutes. In certain embodiments, the treatment time is between about 1 and about 2 minutes, between about 2 and about 3 minutes, between about 3 and about 4 minutes, between about 4 and about 5 minutes, between about 5 and about 6 minutes, between about 6 and about 7 minutes, between about 7 and about 8 minutes, between about 8 and about 9 minutes, between about 9 and about 10 minutes, between about 2 and about 4 minutes, between about 3 and about 5 minutes, between about 4 and about 6 minutes, between about 5 and about 7 minutes, between about 6 and about 8 minutes, between about 7 and about 9 minutes, between about 8 and about 10 minutes, between about 2 and about 5 minutes, between about 3 and about 6 minutes, between about 4 and about 7 minutes, between about 5 and about 8 minutes, between about 6 and about 9 minutes, between about 7 and about 10 minutes, or between about 2 and about 10 minutes. In certain embodiments, the treatment time is between about 10 and about 15 minutes, between about 15 and about 20 minutes, between about 20 and about 25 minutes, between about 25 and about 30 minutes, between about 30 and about 35 minutes, between about 35 and about 40 minutes, between about 40 and about 45 minutes, between about 45 and about 50 minutes, between about 50 and about 55 minutes, or between about 55 and about 60 minutes.

In certain aspects, the self-contained cooling device is placed into a cold environment prior to use. In certain embodiments, the cold environment is a standard freezer, a −20° C. freezer, a −80° C. freezer, an ultra-low temperature ("ULT") freezer, by flash freezing (e.g., using liquid nitrogen, etc.), or any other suitable cold environment. In certain embodiments, the self-contained cooling device is placed into a standard freezer for at least about 12 hours prior to use in methods treating ocular surface discomfort using a self-contained cooling device provided herein. In certain embodiments, the self-contained cooling device is placed into a standard freezer for at least about 4 hours, about 5 hours, about 6 hours, about 7 hours, about 8 hours, about 9 hours, about 10 hours, about 11 hours, or about 12 hours prior to use in methods treating ocular surface discomfort using a self-contained cooling device provided herein.

In certain aspects, the self-contained cooling device is at a predetermined temperature prior to use in methods provided herein. In certain embodiments, the predetermined temperature is a subzero temperature. In certain embodiments, the predetermined temperature is between about −20° C. and about 0° C. In certain embodiments, the predetermined temperature is about −20° C., about −19° C., about −18° C., about −17° C., about −16° C., about −15° C., about −14° C., about −13° C., about −12° C., about −11° C., about −10° C., about −9° C., about −8° C., about −7° C., about −6° C., about −5° C., about −4° C., about −3° C., about −2° C., about −1° C., or about 0° C. In certain embodiments, the predetermined temperature is between about −20° C. and about −18° C., between about −19° C. and about −17° C., between about −18° C. and about −16° C., between about −17° C. and about −15° C., between about −16° C. and about −14° C., between about −15° C. and about −13° C., between about −14° C. and about −12° C., between about −13° C. and about −11° C., between about −12° C. and about −10° C., between about −11° C. and about −9° C., between about −10° C. and about −8° C., between about −9° C. and about −7° C., between about −8° C., and about −7° C., between about −6° C. and about −4° C., between about −5° C. and about −3° C., between about −4° C. and about −2° C., between about −3° C. and about −1° C., or between about −2° C. and about 0° C.

In certain aspects, once the self-contained cooling device contacts the eye of the subject, the eye reaches a treatment temperature. In certain embodiments, the treatment temperature is a subzero temperature. In certain embodiments, the treatment temperature is between about −6° C. and about 4° C. In certain embodiments, the treatment temperature is about −6° C. In certain embodiments, the treatment temperature is about 4° C. In certain embodiments, the treatment temperature is about −20° C., about −19° C., about −18° C., about −17° C., about −16° C., about −15° C., about −14° C., about −13° C., about −12° C., about −11° C., about −10° C., about −9° C., about −8° C., about −7° C., about −6° C., about −5° C., about −4° C., about −3° C., about −2° C., about −1° C., about 0° C., about 1° C., about 2° C., about 3° C., or about 4° C. In certain embodiments, the treatment temperature is between about −20° C. and about −18° C., between about −19° C. and about −17° C., between about −18° C. and about −16° C., between about −17° C. and about −15° C., between about −16° C. and about −14° C., between about −15° C. and about −13° C., between about −14° C. and about −12° C., between about −13° C. and about −11° C., between about −12° C. and about −10° C., between about −11° C. and about −9° C., between about −10° C. and about −8° C., between about −9° C. and about −7° C., between about −8° C., and about −7° C., between about −6° C. and about −4° C., between about −5° C. and about −3° C., between about −4° C. and about −2° C., between about −3° C. and about −1° C., between about −2° C. and about 0° C., between about −1° C. and about 1° C., between about 0° C. and about 2° C., or between about 2° C. and about 4° C.

In certain aspects, methods and devices provided herein achieve a rapid temperature decrease after an eye is contacted with a self-contained cooling device according to the present disclosure. In certain embodiments, an ocular (i.e., target) surface interface of the self-contained cooling device contacts a sclera of an eye, wherein the sclera reaches a treatment temperature (e.g., below 0° C.) after about 30 seconds. In certain embodiments, the sclera reaches a treatment temperature (e.g., below 0° C.) after about 10 seconds, about 15 seconds, about 20 seconds, about 25 seconds, about 30 seconds, about 35 seconds, about 40 seconds, about 45 seconds, about 50 seconds, about 55 seconds, about 60 seconds, about 70 seconds, about 80 seconds, about 90 seconds, about 100 seconds, about 110 seconds, about 120 seconds, about 130 seconds, about 140 seconds, about 150 seconds, about 160 seconds, about 170 seconds, about 180 seconds, about 190 seconds, about 200 seconds, about 210 seconds, about 220 seconds, about 230 seconds, about 240 seconds, about 250 seconds, about 260 seconds, about 270 seconds, about 280 seconds, about 290 seconds, about 300 seconds, about 310 seconds, about 320 seconds, about 330 seconds, about 340 seconds, about 350 seconds, about 360 seconds, about 370 seconds, about 380 seconds, about 390 seconds, about 400 seconds, about 410 seconds, about 420 seconds, about 430 seconds, about 440 seconds, about 450 seconds, about 460 seconds, about 470 seconds, about 480 seconds, about 490 seconds, about 500 seconds, about 510 seconds, about 520 seconds, about 530 seconds, about 540 seconds, about 550 seconds, about 560 seconds, about 570 seconds, about 580 seconds, about 590 seconds, or about 600 seconds.

In certain aspects, the self-contained cooling device comprises an insulation feature. In certain embodiments, the insulation feature is a gap between a housing and a heat exchanger of the self-contained cooling device. In certain embodiments, the gap is an air gap. In certain embodiments, the gap is filled with an insulating material. Insulating the self-contained cooling device provides advantages by minimizing condensation on the self-contained cooling device, maintaining a desired temperature of the self-contained cooling device including of one or more contact surfaces and/or by maintaining a volume of a thermal mass (e.g., within the heat exchanger).

In certain aspects, the self-contained cooling device is configured to be balanced. A balanced self-contained cooling device may be advantageous because it allows for ease of positioning for a clinician during use.

Figure 20B:
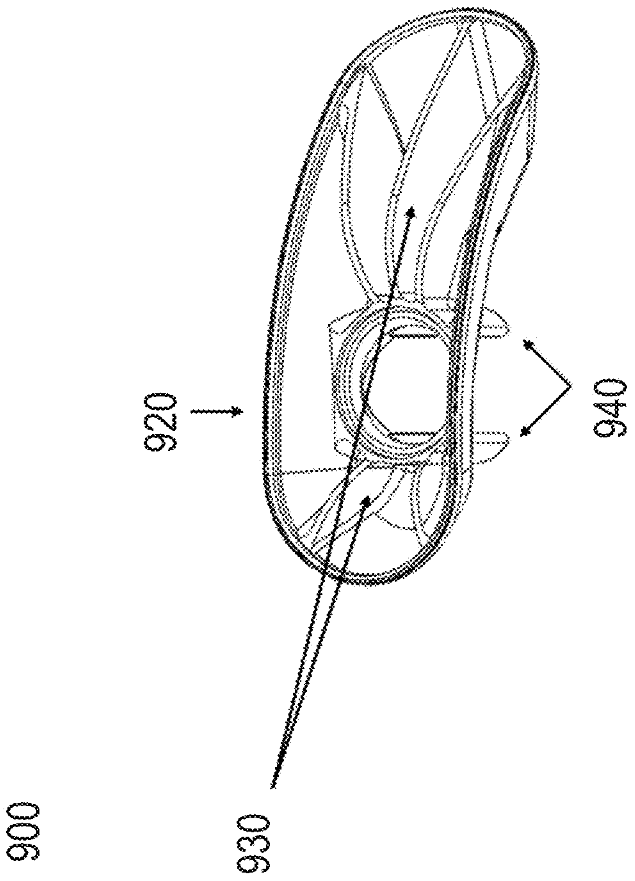
FIGS. 20A and 20B show an exploded view of an exemplary self-contained eye cooling device (20A) with a heat exchanger (20B) according to certain embodiments described herein.
Figure 20A:
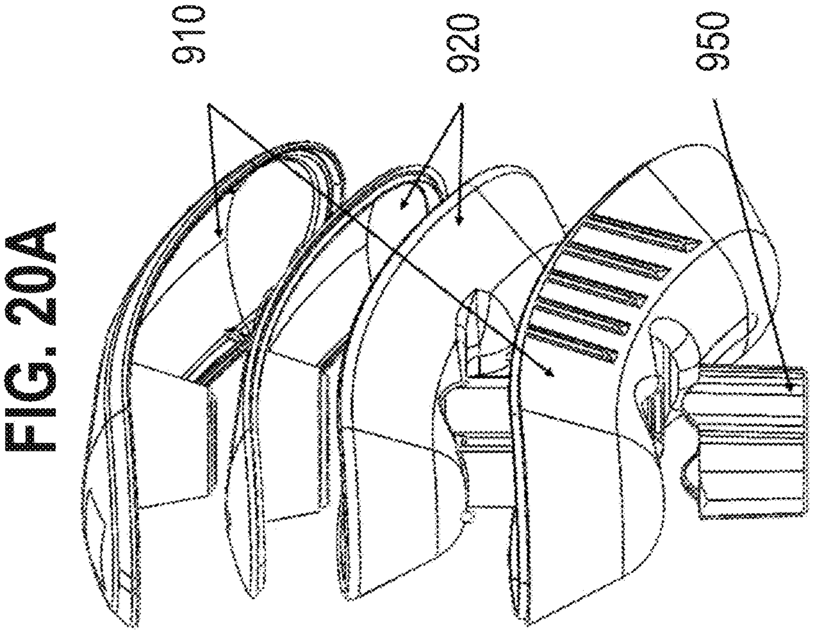
Figure 21B:
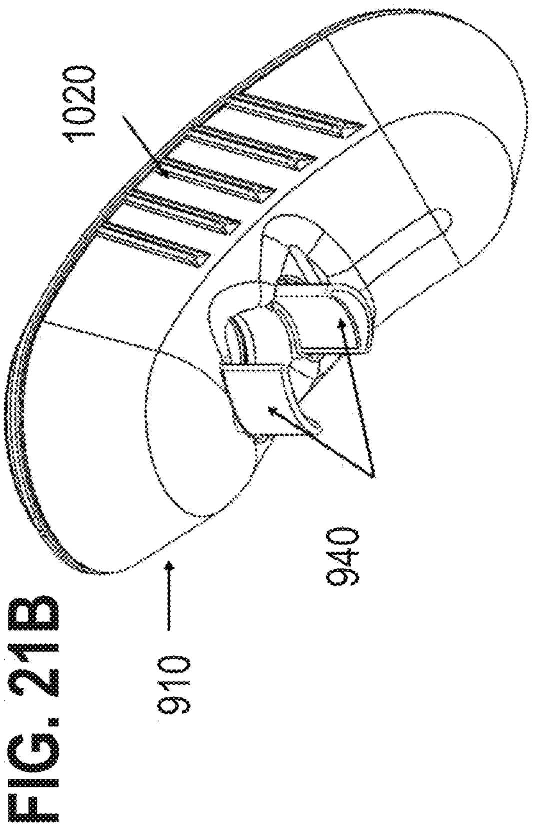
FIGS. 21A-E show an exemplary self-contained eye cooling device from multiple angles according to certain embodiments described herein.
Figure 21A:
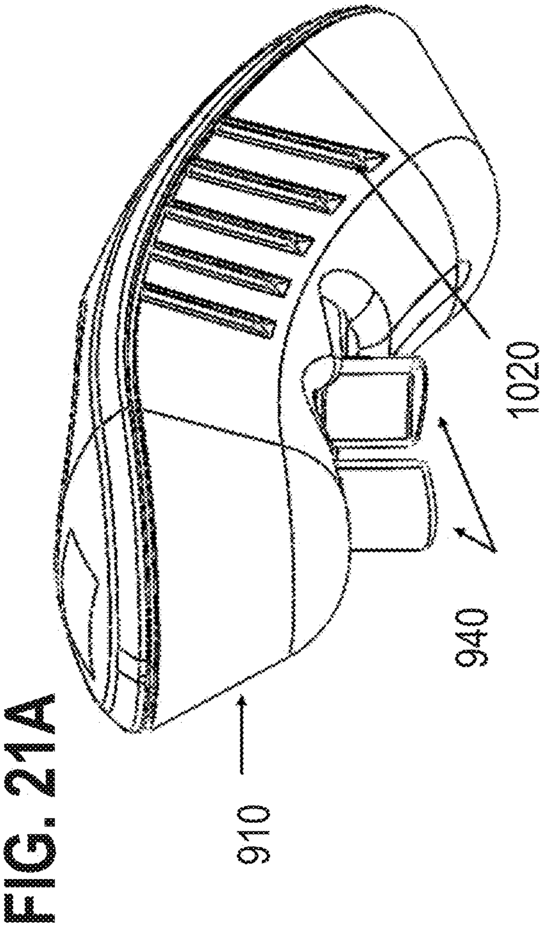
Figure 21D:
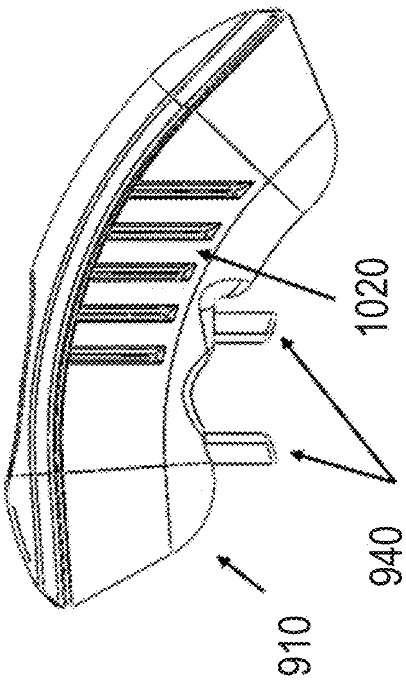
Figure 21E:
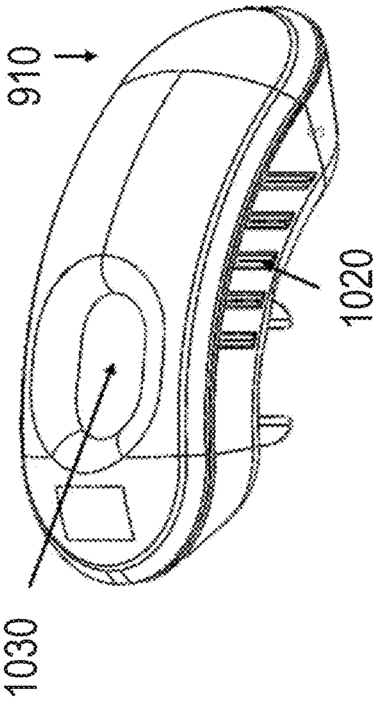
Figure 21C:
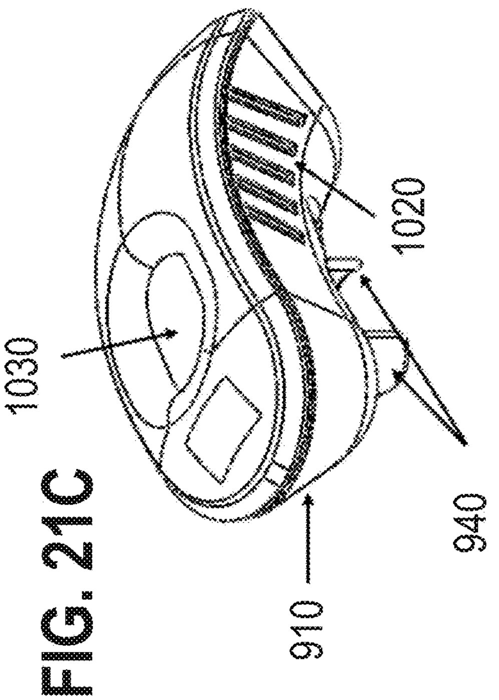

Referring to FIGS. 20A and 20B, an exploded view of a self-contained cooling device according to the present disclosure is provided. In certain embodiments, the self-contained cooling device 900 comprises a housing 910 that houses heat exchanger 920. In certain embodiments, the housing 910 comprises a plurality of pieces, e.g., a top piece and a bottom piece. In certain embodiments, the housing 910 comprises one or more polycarbonate pieces. In certain embodiments, the self-contained cooling device comprises a gap between the housing 910 and the heat exchanger 920. In certain embodiments, the gap provides insulation for the heat exchanger 920, e.g., an air gap. In certain embodiments, the heat exchanger 920 is made of a thermally conductive material. Exemplary thermally conductive materials include but are not limited to Al, Cu, Au, Ni, Ag, stainless steel, metal alloys, diamond, thermally conductive plastics including metal impregnated polyimide, or combinations thereof. In certain embodiments, the heat exchanger 920 comprises a cavity wherein the cavity contains a thermal mass (e.g., liquid, solid, or partially solid cold slurry formulation). In certain embodiments, the thermal mass is contained inside the heat exchanger 920. In certain embodiments, the thermal mass is frozen in a standard freezer. In certain embodiments, heat exchanger 920 contains a bottom piece and a top piece that may be separate components that can be joined together. In certain embodiments, the thermal mass is sealed within the heat exchanger 920, for example by using an adhesive to join the top piece and the bottom piece after the thermal mass has been placed inside the heat exchanger 920 chamber. In certain embodiments, heat exchanger 920 is formed from a single piece of metal, e.g., by being machined out of copper. This allows the self-contained cooling device to cause the ocular surface to reach a cold temperature very quickly by facilitating heat exchange between the ocular surface and the heat exchanger 920. In certain embodiments, the heat exchanger 920 further comprises conductive structures 930 (e.g., fins or walls) to conduct heat from the ocular surface into the frozen thermal mass. In certain embodiments, the self-contained cooling device comprises an ocular (i.e., target) surface interface 940 configured to freeze to a sclera of an eye upon contact. In certain embodiments, the self-contained cooling device comprises an ocular (i.e., target) surface interface 940 configured to not freeze to a sclera of an eye upon contact. In certain embodiments, the self-contained cooling device comprises a cap 950 configured to prevent condensation on the ocular (i.e., target) surface interface prior to use.

Referring to FIGS. 21A-E, a plurality of external drawings of the self-contained cooling device depicted in FIGS. 20A and 20B are provided. In certain embodiments, the self-contained cooling device comprises a housing 910. In certain embodiments, the housing 910 comprises a grip interface 1020. In certain embodiments, the grip interface 1020 is configured to assist the clinician in holding the device, e.g., by indicating proper finger placement or making the device easier to hold. In certain embodiments, the self-contained cooling device comprises an aperture 1030 configured to provide visibility of a cornea during a procedure. In certain embodiments, the self-contained cooling device comprises an ocular (i.e., target) surface interface 940 configured to freeze to a sclera of an eye upon contact.

Figure 22A:
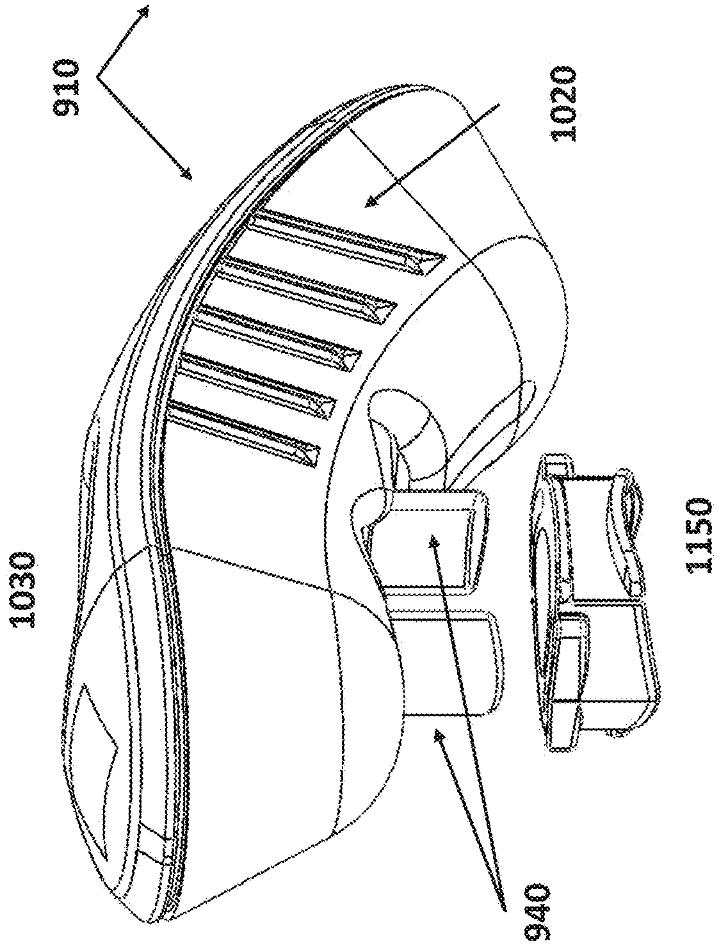
FIGS. 22A and 22B show an exemplary self-contained eye cooling device and an accessory (e.g., speculum) before the self-contained eye cooling device is placed through the accessory (22A) and after the self-contained eye cooling device is placed through the accessory (22B) according to certain embodiments described herein.
Figure 22B:
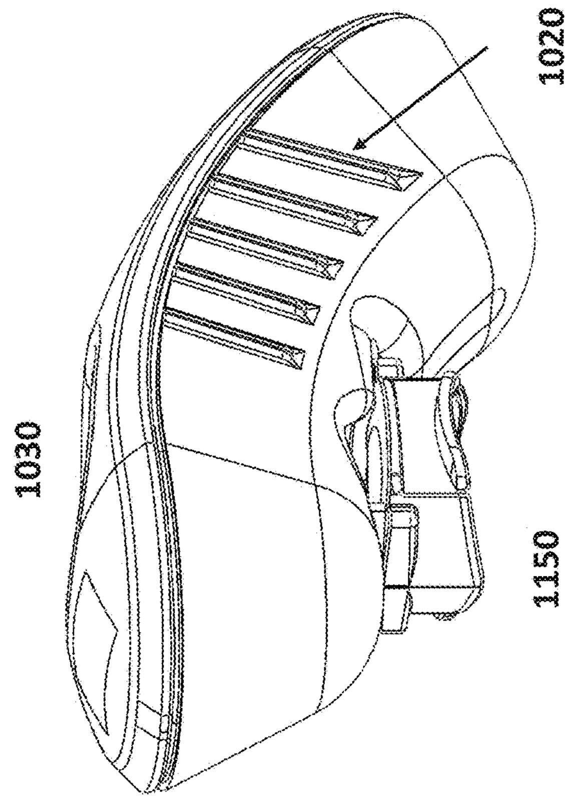
Figure 23B:
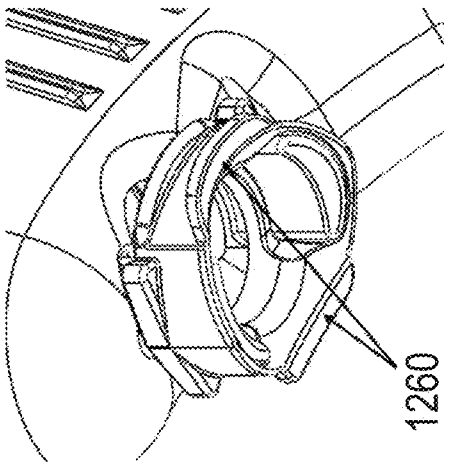
FIGS. 23A-D show multiple views of an accessory (e.g., a speculum) for use with a self-contained eye cooling device according to certain embodiments described herein.
Figure 23D:
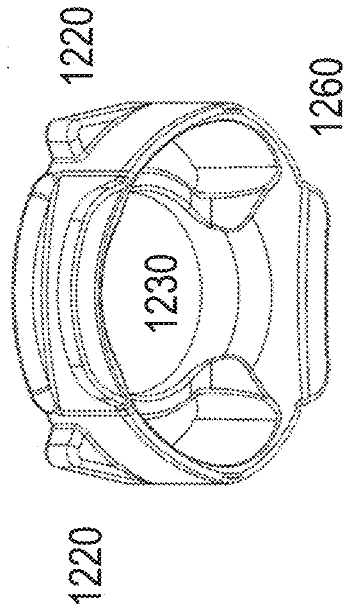
Figure 23A:
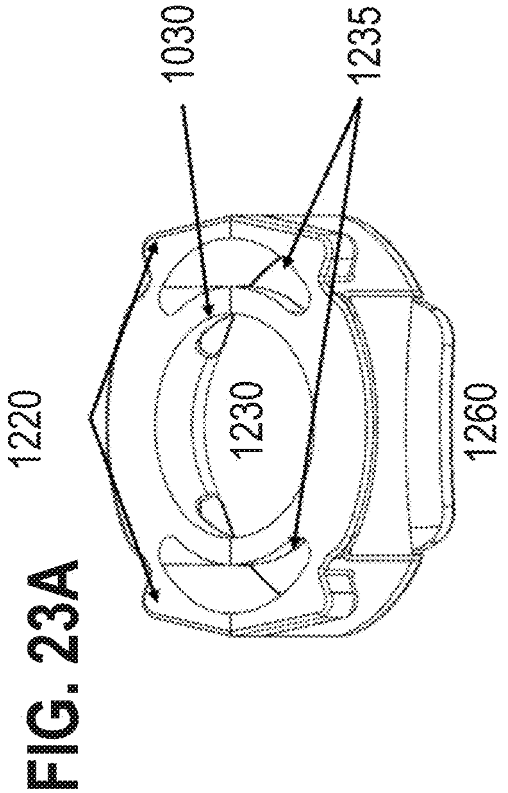
Figure 23C:
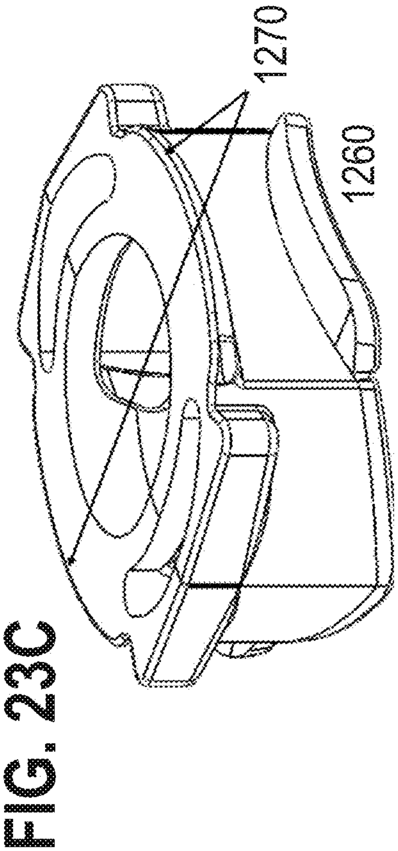

Referring to FIGS. 22A and 22B, drawings of a self-contained cooling device provided in FIGS. 20A, 20B, and 21A-E and an accessory according to the present disclosure are provided. In certain embodiments, the self-contained cooling device comprises a housing 910, a grip interface 1020, an aperture 1030, an ocular (i.e., target) surface interface 940 configured to freeze to a sclera of an eye upon contact. In certain embodiments, an accessory 1150 (e.g., a speculum) is provided, wherein the accessory is configured to assist in holding open an eye of a subject and assist in proper placement of the self-contained cooling device during a procedure. In further embodiments, the accessory insulates the eyelids from the ocular surface interface 940. In certain embodiments, the accessory comprises a flexible, insulating material (e.g., silicone). Drawings of an accessory according to certain embodiments of the present disclosure are provided in FIGS. 23A-D. In certain embodiments, the accessory comprises an aperture 1230 configured to allow a clinician to visualize a cornea of a subject. In certain embodiments, the accessory comprises one or more guide features 1235 (e.g., cutouts) configured to assist the clinician in placing the self-contained cooling device during a procedure. In certain embodiments, the accessory comprises one or more surfaces 1260 configured to fit under the eyelids of the subject to hold open the eyelids during the procedure. In certain embodiments, the accessory comprises one or more features 1270 configured to push the patient's eyelashes away from the self-contained cooling device. In certain embodiments, the accessory further comprises an accessory grip interface 1220. In certain embodiments, the accessory grip interface 1220 is configured to assist the clinician in proper placement of the accessory.

In some embodiments, the self-contained cooling device is reusable. In some embodiments, the self-contained device is disposable.

Figure 25:
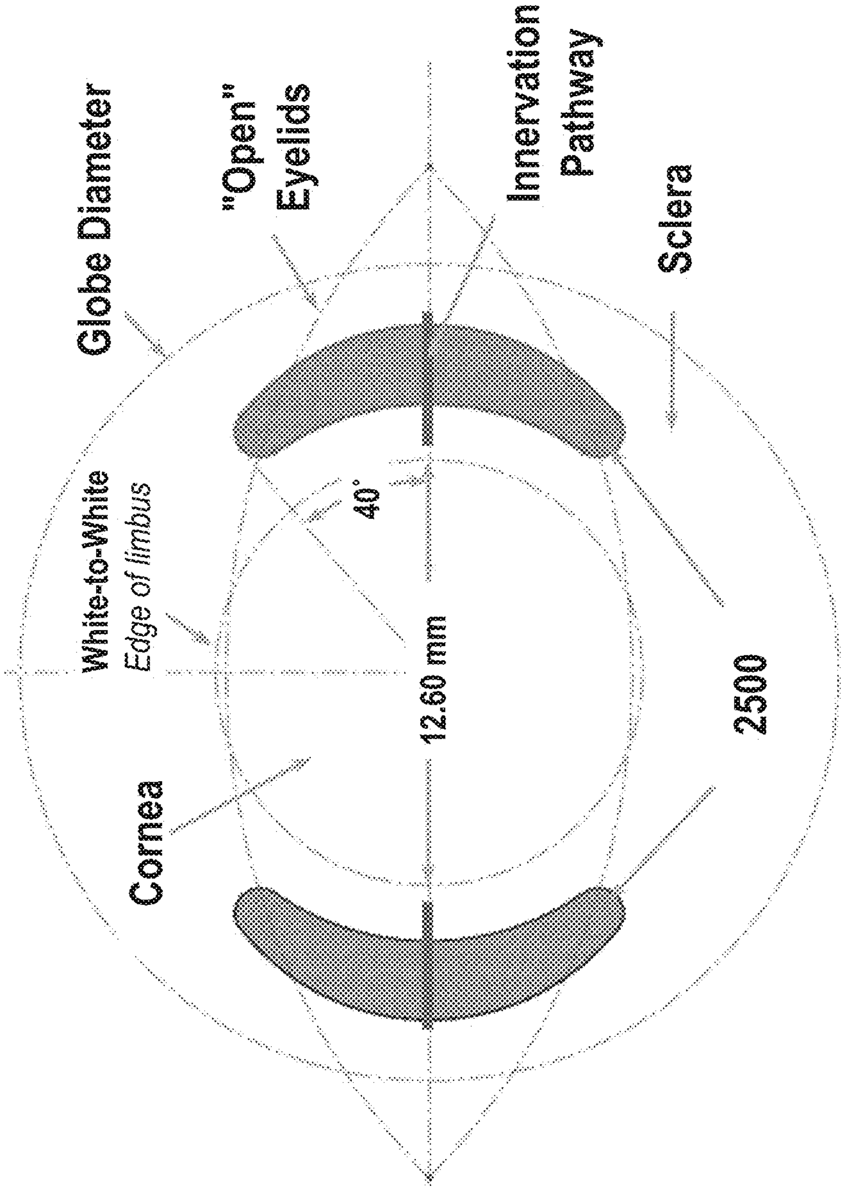
FIG. 25 is a diagram depicting exemplary treatment zones 2500 on a drawing of an eye.

Referring now to FIG. 25, a figure illustrating exemplary treatment zones 2500 on a diagram of an eye. In certain embodiments, ocular (i.e., target) surface interface 940 is configured to contact treatment zone 2500.

In certain aspects, the self-contained cooling device may be used in combination with methods for treating ocular surface discomfort provided herein. In certain embodiments, the self-contained cooling device is placed in a cold environment (e.g., a standard freezer) before use as described herein. In certain embodiments, the self-contained cooling device is placed in a standard freezer for at least 12 hours before use. In certain embodiments, the self-contained cooling device is configured to be used in combination with an accessory. For example, an accessory (e.g., a speculum) may be placed to hold open an eye of a subject. A clinician may place the accessory into the eye of the subject, e.g., by squeezing the accessory while holding accessory grip interface 1220 such that surfaces 1260 may be positioned under an eyelid of the subject to hold the eye open. After placing the speculum, the self-contained cooling device is placed. Optionally, features 1270 may push the patient's eyelashes away from the self-contained cooling device while in use. In certain embodiments, the accessory (e.g., speculum) includes guide features 1235 configured to ensure proper placement of the self-contained cooling device, for example, a clinician may place an ocular (i.e., target) surface interface 940 of the self-contained cooling device through guide features 1235. Next, the clinician may visualize the eye of the patient (e.g., including a cornea of the eye) through aperture 1030/1230 to maintain proper device position before making contact with the eye using ocular surface interface 940. Upon contact, ocular surface interface 940 may adhere to the eye and remain in contact with the eye for a treatment time (e.g., between about 2 minutes and about 10 minutes). After the treatment time, steps may be taken to avoid adhesion between the eye and the ocular surface interface 940 of the self-contained cooling device following treatment. In certain embodiments, the eye is rinsed (e.g., with saline and optionally warmed saline or other suitable fluid and optionally warmed fluid) to avoid adhesion between the eye and the ocular surface interface 940 of the self-contained cooling device following treatment. After rinsing, the self-contained cooling device and the accessory are removed from the eye. In certain embodiments, the self-contained cooling device is warmed following treatment by, e.g., using an electrical heating element or system, removing the thermal mass, flushing the inside of the device with a fluid and optionally a warmed fluid, or a chemical (exothermic) reaction. In certain embodiments, the ocular surface interface 940 or the accessory comprises one or more channels configured to facilitate rinsing.

Mechanism of Action

Without being bound by any theory, the basic premise is that application of subzero temperatures (e.g., between about −20° C. and about 0° C.) halts the signaling of painful stimuli by causing degeneration of the myelin sheath over the nerves. Myelin is a fatty, lipid-rich substance that allows electrical stimuli to travel down the nerve axon in a quick and efficient manner. With the administration of cold slurry or other cooling treatment (e.g., using a self-contained cooling device according to the present disclosure) over both the free nerve endings and myelinated portion of the nerves, the cold temperature will freeze or crystallize the lipid component of fat cells, inducing apoptosis, and degenerating the myelin sheath, a process known as Wallerian degeneration. This process will significantly reduce ciliary nerves from conducting painful stimuli from the cornea to the brain stem. Due to the sheer volume of distal nerve endings on the ocular surface, not all peripheral nerves are affected, therefore not all sensation from the ocular surface is eliminated, thus inducing relative hypesthesia instead of complete anesthesia. Furthermore, the effect regresses after approximately 4-8 weeks at which time ocular sensation is fully restored. Other options that induce Wallerian degeneration include radiofrequency ablation and cryoneurolysis (freezing at temperatures approaching −80° C.), but these procedures pose the risk of damaging surrounding tissue and structures. Furthermore, an inactive vehicle containing ice crystals will not harm other components of the eye, making it a reasonable application for treating nerves that lead to ocular surface pain. This approach preserves sight and normal function of the ocular surface.

Without being bound by a specific theory, injection into the subconjunctival space surrounding the corneal limbus distributes the cold slurry around the free nerve endings of the ciliary nerves. Moreover, topical slurry administration or application cold (e.g., using a self-contained cooling device provided herein) may be used to target ciliary nerves and their free nerve endings with cold temperatures. There are two main ciliary nerves that have free nerve endings branching into the corneas of each eye. Each ciliary nerve is myelinated along its axon, which is located downstream from the free nerve endings in the cornea. The injection of the cold slurry and/or the cold temperature from a topically applied cold slurry and/or self-contained cooling device spreads downstream to where the axon of the ciliary nerve is myelinated. As the cold slurry and/or the cold temperature from a topically applied cold slurry and/or self-contained cooling device spreads to the axons of the ciliary nerves, it causes crystallization and apoptosis of the myelin sheath, thus demyelinating the ciliary nerves. The demyelination prevents the nerves from transmitting pain signals to the brain. Alternatively, the cold slurry and/or the cold temperature from a topically applied cold slurry and/or self-contained cooling device can cause Wallerian degeneration of the nerve and similarly prevent pain signals from being transmitted to the brain. Alternatively, the cold slurry and/or the cold temperature from a topically applied cold slurry and/or self-contained cooling device can target the free nerve endings of ciliary nerves.

The topically applied and/or injected cold slurry, or self-contained cooling device is advantageous over other methods of administration because it does not damage the surface of the cornea.

The systems and methods disclosed herein are not to be limited in scope to the specific embodiments described herein. Indeed, various modifications of the devices, systems, and methods in addition to those described will become apparent to those of skill in the art from the foregoing description. The data described herein support cold slurry (topical and injection) and application of self-contained cooling devices as a long-term and safe corneal numbing treatment which produces hypesthesia without permanent corneal numbering or damage.

Example 1—In Vivo Testing of Cold Slurry Treatment for Corneal Numbing

The results of the studies described in this Example can be seen in FIGS. 5-9. Preclinical testing with animal studies was performed to determine the efficacy of the therapy including investigating the best means to deliver the therapy, the duration of the therapy's effect, and any potential side effects. For ophthalmic investigations, the New Zealand white rabbits are the ideal model because their cornea and corneal innervation system are very similar to humans, and they are a standard accepted model for corneal studies in the literature.

Procedural Preparation

Animals were given a pre-anesthetic (rabbits Xylazine 1.1 mg/kg IM Buprenorphine HCL 0.01-0.05 mg/kg IM) and a pre-surgical antibiotic (Cefazolin 25-50 mg/kg IM). Animals were then anesthetized (rabbits Ketamine 33 mg/kg IM). Animals were placed on heating pad and the vitals monitored. Two drops of Proparacaine HCL 0.5% and 5% phenylephrine/0.5% tropicamide (dilating drops) were administered to the eye to be studied. Animals were put on inhalation anesthesia (isoflurane at 1.5-2% concentration) with an $O_2$ supplement.

Study Procedure

Animals were prepped and draped in the usual sterile fashion including the instillation of povidone-iodide drops onto the ocular surface. A speculum was placed, and a topical or subconjunctival injection of the slurry is performed.

Injection Administration

For evaluating the hypesthetic potential of ECT-1719, approximately 0.7 mL of cold slurry were injected around the corneal limbus into the subconjunctival space. The injected cold slurry distributes evenly, 360 degrees, around the corneal limbus due in part to pressure from the cornea, the force of the injection, and the natural potential space present. The injection procedure is repeated every 120 seconds for a total of 10 minutes.

Control animals received treatment with sterile saline (control) or treatment with a vehicle control (uncooled slurry). At the conclusion of the procedure, the eye was carefully inspected, the speculum removed, the drapes removed, and the eye washed with sterile saline. There was an additional control group that has conventional anesthetic drops applied to the cornea. All surgery is on the left eye only (for control purposes) and lasted about 10 minutes.

The surgical procedure described above is commonly performed in humans with injection of a variety of different agents depending on the condition (e.g., steroids, antibiotics, etc.).

Topical Administration

For evaluating the hypesthetic potential of ETX-4143, the slurry was applied topically to the ocular surface, posterior to the cornea limbus. The cornea was protected with a contact lens and the eyelids with a plastic speculum. Approximately 2 mL of cold slurry were applied topically every approximately 30 seconds for first 4 minutes, and then approximately every minute until a total treatment time of 10 minutes was reached. At the conclusion of the procedure, the eye was carefully inspected, the speculum removed, the drapes removed, and the eye washed with sterile saline.

Post-Procedures for a Survival Animal

A Neomycin/Polymyxin/Bacitracin ophthalmic ointment was applied to the operative eye, as well as several drops of Prednisone Acetate postoperatively. Animal were removed from a surgical table and placed on a heating pad. Animals had their vitals monitored (e.g., heart rate, breathing, $SPO_2$) while waiting for recovery. Animals continued to be monitored until regaining muscle control. Animals were returned to their respective cage of origin.

Post-Surgery Animal Monitoring

Animals receive a comprehensive eye exam one day after surgery and then weekly which included a measurement of corneal sensation. A measurement of intraocular pressure was taken as well, as a beneficial lowering of intraocular pressure may be observed in animals that have undergone this therapy. Furthermore, a slit lamp exam with fluorescein staining and dilated fundus exam (i.e., eyes are dilated with 5% phenylephrine, 0.5% tropicamide) was performed. Animals were placed in restrictive cages for a few seconds while eye drops were instilled.

Effect of Administration

The effect of the administration of the cold slurry were examined using a number of techniques.

The cold slurry's numbing effect was tested using an esthesiometer. A filament was extended from the device that had a certain stiffness. The animals treated with cold slurry were able to tolerate more force from the esthesiometer than animals in the control groups. This was demonstrated by whether an animal flinches when poked in the eye with the esthesiometer filament. The test was administered multiple times over the course of the study to determine the length of the numbing effect.

The impact of the cold slurry on the eye's ability to heal was also examined. An epithelial defect on the cornea was created with a trephine and corneal brush. The injury was verified with a fluorescein stain and photo-documented. The progress of the injury was measured using fluorescein staining and measuring the size of the injury. The cold slurry did not impact the eye's ability to heal.

Figure 26:
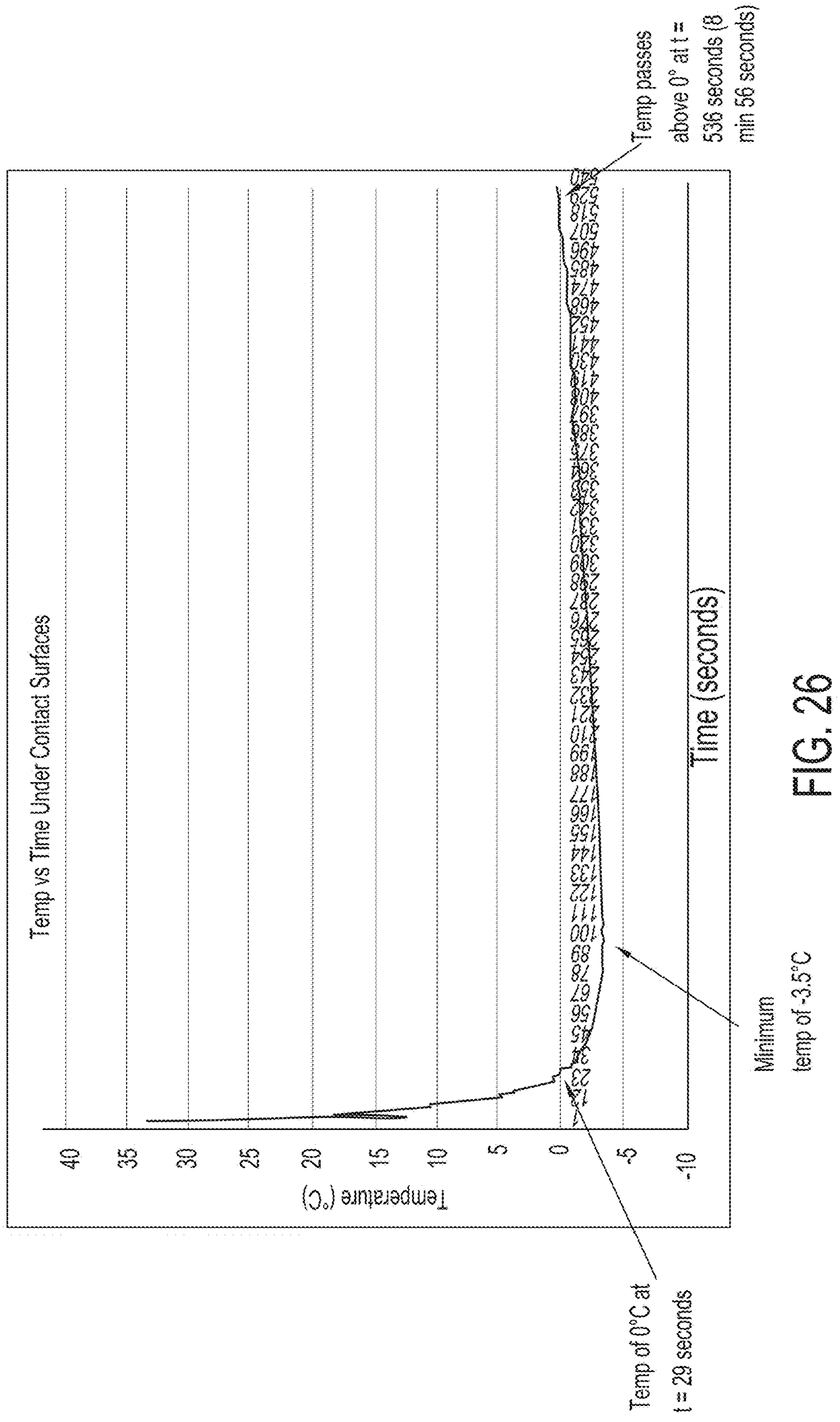
FIG. 26 is a graph showing a representative temperature profile comparing temperature (° C.) of a surface of a pig eye versus time (seconds) upon contact with a self-contained cooling device according to certain embodiments described herein.
Figure 27:
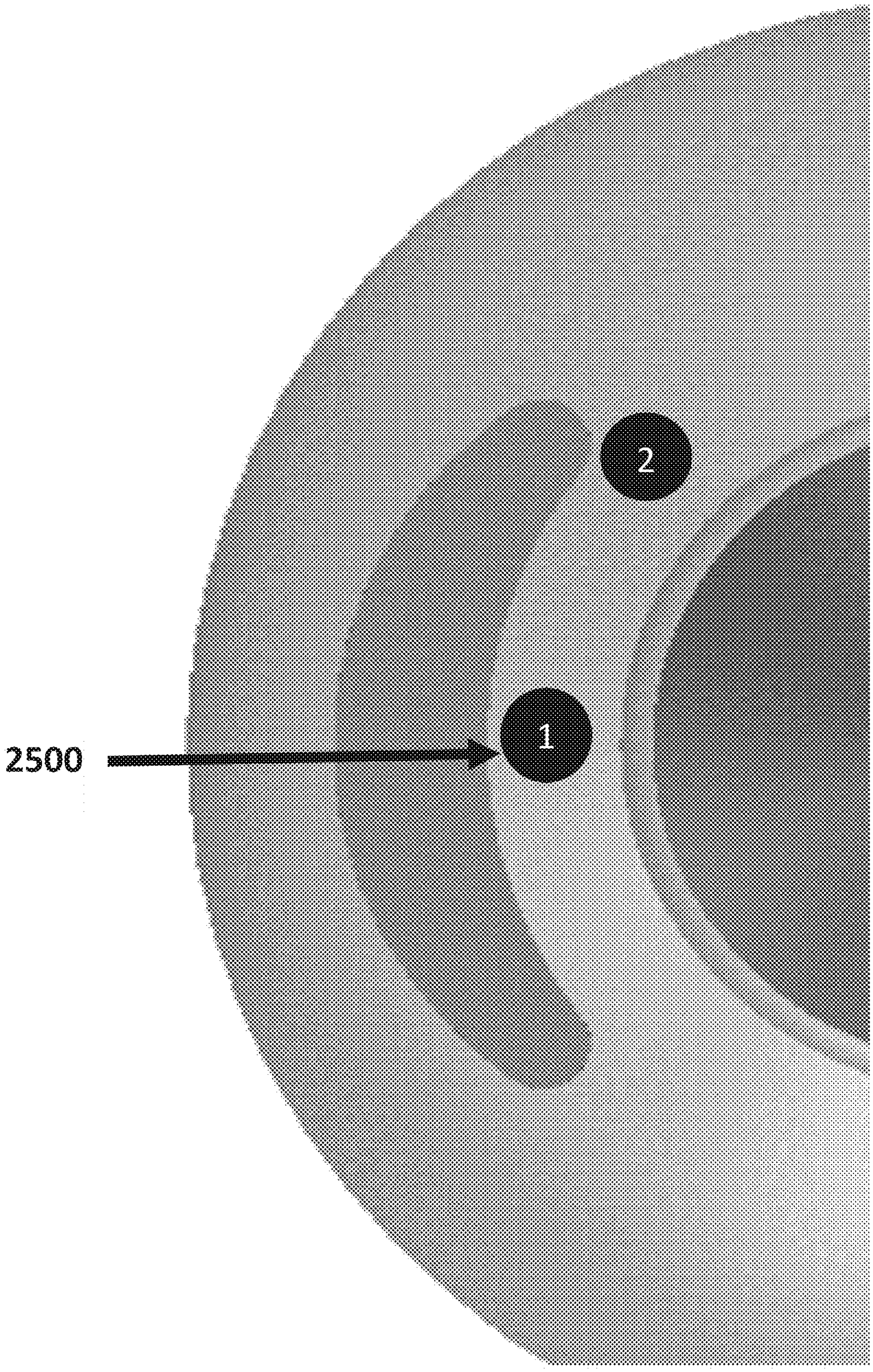
FIG. 27 is a drawing showing temperature measurement locations 1 and 2 on a diagram of an eye along with treatment zone 2500 (located under a contact surface of a self-contained cooling device according to the present disclosure).
Figure 28:
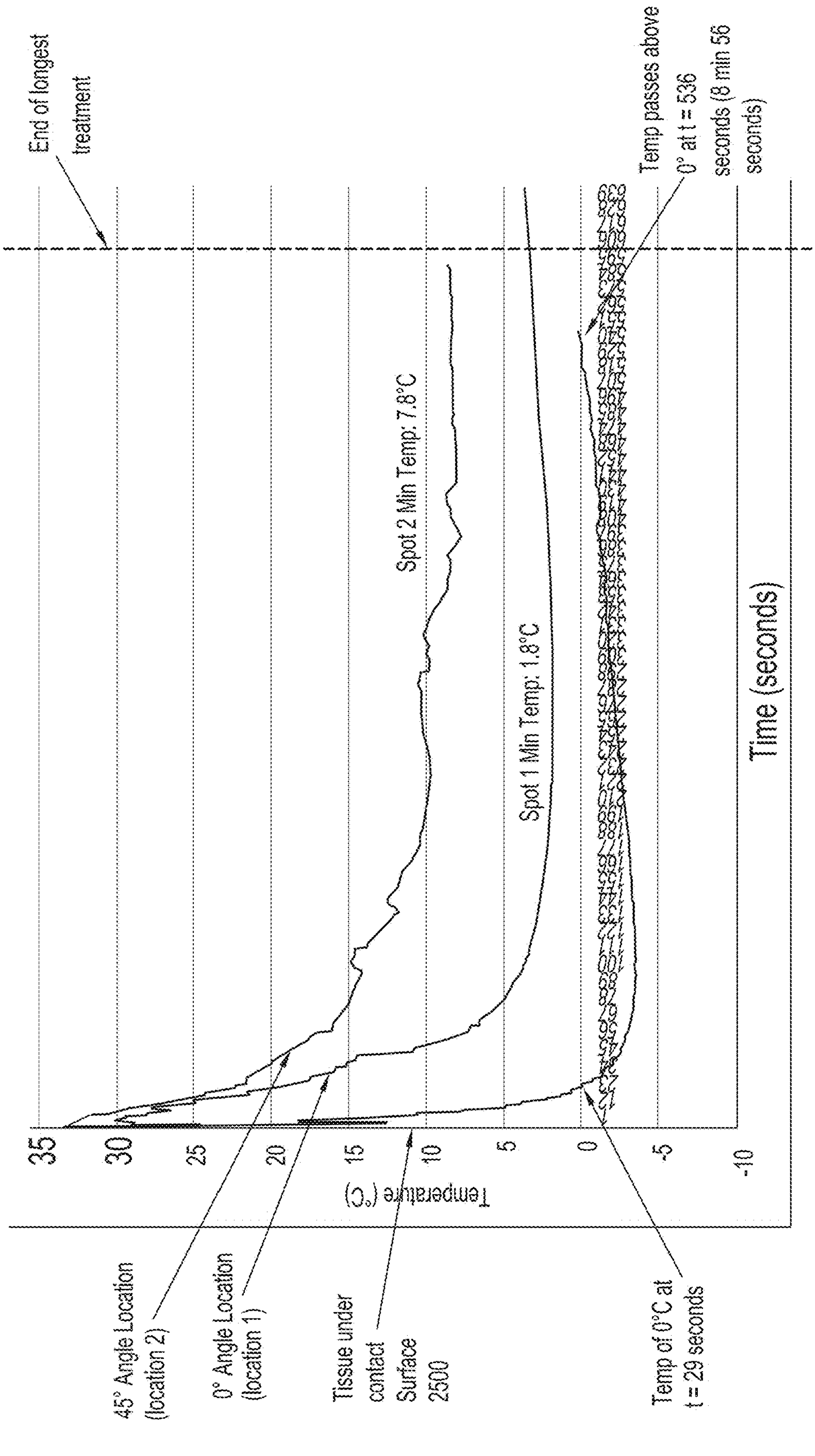
FIG. 28 is a graph showing temperature (° C.) versus time (seconds) for temperatures taken at measurement locations 1 and 2 and from tissue under treatment zone 2500.

Example 2—In Vitro Testing of Self-Contained Cooling Device Treatment for Corneal Numbing The results of the study described in this Example can be seen in FIGS. 26, 27, and 28. Preclinical testing with animal studies was performed to determine the thermal effect of a self-contained cooling device according to the present disclosure.

Referring to FIG. 26, pig eye surfaces were used in this Example to generate a representative temperature profile of temperatures taken from the surface of a pig eye. A pig eye was contacted with an ocular surface interface of a self-contained cooling device according to the present disclosure. In this Example, the ocular surface interface is a copper ocular surface interface that is joined with the heat exchanger to form one piece and the self-contained cooling device contained a thermal mass comprising 20% glycerol by weight in purified water. The temperature of the pig eye was measured over time and is presented in FIG. 26. As shown in FIG. 26, the temperature reached 0° C. after 29 seconds. A minimum temperature of −3.5° C. was recorded. Finally, the temperature again rose above 0° C. after 536 seconds (8 minutes and 56 seconds).

Temperature measurements were also taken from pig eyes at three locations as indicated in FIG. 27 and described below. Pig eyes were partially immersed in a water bath to heat the eye to a representative surface temperature of about 33° C. Temperatures were monitored at three locations as shown in FIG. 27: location 1 (positioned 0° from horizontal and 1.5 mm from treatment zone 2500); location 2 (positioned 45° from horizontal and 1.5 mm from treatment zone 2500), and under treatment zone 2500.

Pig eyes were contacted with a self-contained cooling device as described above with respect to FIG. 26, and measurements were recorded over time. As shown in FIG. 28, the temperature below treatment zone 2500 reached 0° C. after 29 seconds and rose above 0° C. again after 536 seconds (8 minutes and 58 seconds). The representative temperature profile below treatment zone 2500 depicted in FIG. 26 is also shown in FIG. 28. Temperatures at location 1 (positioned 0° from horizontal and 1.5 mm from treatment zone 2500) and location 2 (positioned 45° from horizontal and 1.5 mm from treatment zone 2500) were also recorded. Results demonstrated that location 1 reached colder temperatures than location 2.

Figure 29:
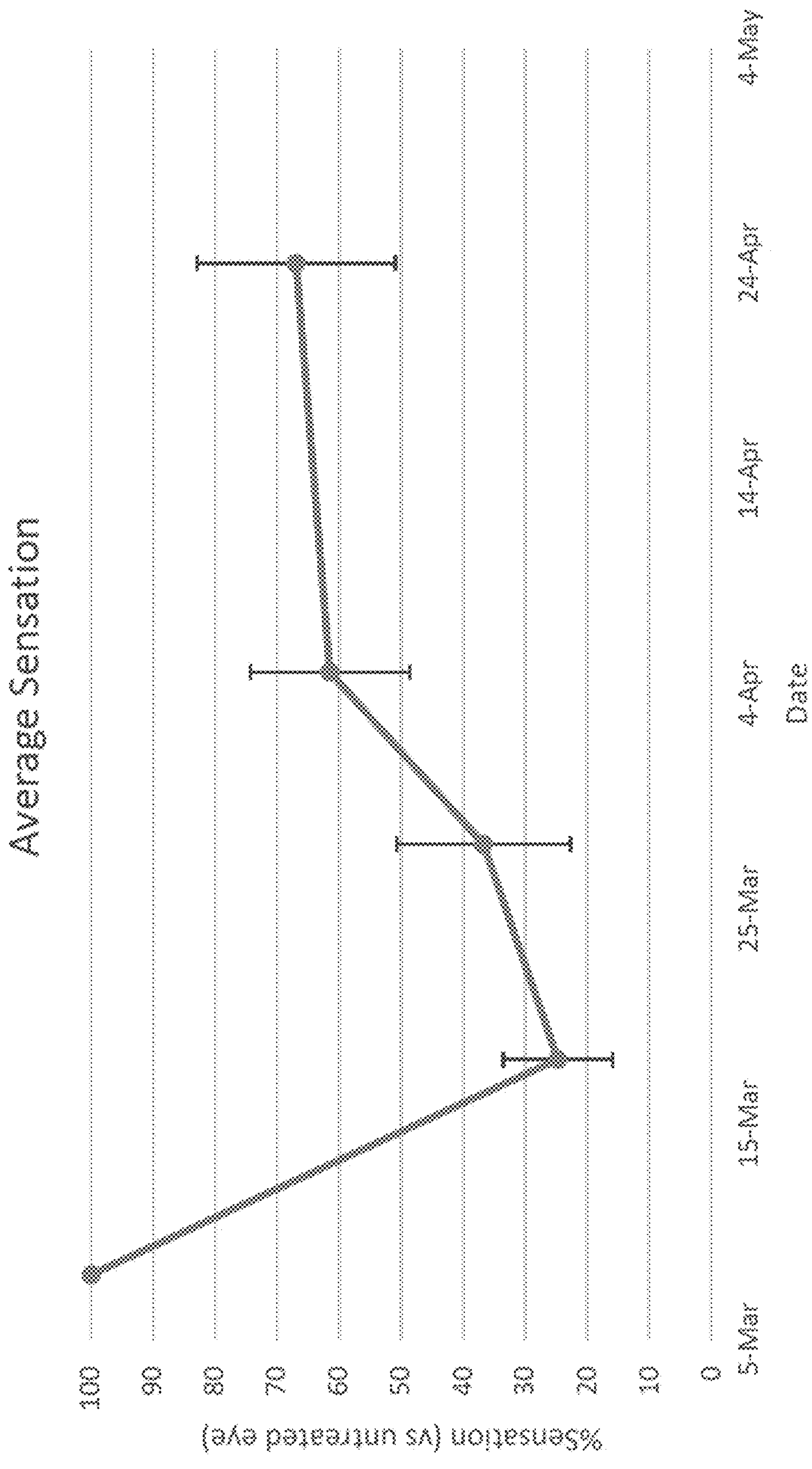
FIG. 29 is a graph showing percent sensation of a treated rabbit eye compared to an untreated time over time (by date).

Example 3—In Vivo Testing of Self-Contained Cooling Device Treatment for Corneal Numbing The results of the studies described in this Example can be seen in FIG. 29. Preclinical testing with animal studies was performed to determine the efficacy of therapy using the self-contained cooling device including investigating the ability to cool the eye, evaluate the impact on numbing/anesthetizing the corneal surface, the duration of the therapy's effect, and any potential side effects. As indicated in Example 1, for ophthalmic investigations, the New Zealand white rabbits are the ideal model because their cornea and corneal innervation system are very similar to humans, and they are a standard accepted model for corneal studies in the literature.

Self-Contained Cooling Device

Self-contained cooling devices were designed to allow for use treating a rabbit eye that is analogous to the treatment of a human eye. The self-contained cooling devices included a thermocouple embedded in the eye contact surface to measure the temperature of the surface of the eye during the procedure. The devices were designed to contact and treat 200 degrees on the rabbit eye (220° total–20° gap), specifically targeting the portion of the sclera just outside the cornea. Previous studies have shown that it is difficult to treat all areas around the cornea in this model. The contact surface (copper) was protected from the rabbit eyelid. The contact surface was configured to conduct heat directly into the chamber of the device, which was filled with ice with a depressed freezing point. In this Example, the ice was a mixture of purified water and glycerol (20% wt/wt). Prior to use, the devices were placed into a freezer set at −20° C. and allowed them to sit for at least 12 hours, or alternately for 2 hours at −27° C. and 2 more hours at −20° C. (4 hour refreeze).

Self-Contained Cooling Device Procedure

Prior to anesthetization, perform a corneal sensation test was performed. Subjects were anesthetized in the standard fashion consistent with the approved IACUC protocol. Topical proparacaine was administered to both the treatment eye and the control eye. The subject's eyelids were opened to expose the cornea and as much of the sclera as possible with the use of a speculum. If needed, a cornea protector device (contact lens suction device) was placed by suctioning onto the cornea. When using the device, the cornea is centered between two contact surfaces. The device was placed such that it is covering approximately 240 degrees of the scleral surface around the cornea and care was taken to ensure that the device was minimally encumbered by the subject's eyelids. Contact was maintained between the device and the eye for 10 minutes. At the end of the contact time, the eye and device were rinsed with warm water or saline, and the device was removed from the eye.

Post-Procedure Monitoring

Following the procedure, subjects were monitored for overall health for one week. Subjects were also given a comprehensive eye exam one week after the procedure and then weekly (+/−3 days) which included a corneal sensation test using an esthesiometer and intraocular pressure ("IOP") measurements.

Effect of Self-Contained Cooling Device Procedure

The rabbits showed a significant reduction in sensation in comparison to their respective non-treated eyes, with an average reduction of around 75% at week one and 63% at week two. See FIG. 29. The most reduction in sensation was measured close to a week following treatment, with five of the eight rabbits exhibiting more than 85% reduction in sensation when compared to the control eye. No adverse effects were observed as a result of the treatment.

What is claimed is:

1. A self-contained cooling device for cooling a target tissue surface of an ocular surface of a subject, the self-contained cooling device comprising:

a formulation chamber comprising a hollow chamber with an open end, wherein the formulation chamber is configured to receive and hold a cold slurry formulation having a plurality of ice crystals;

a lid configured to fit over and seal the open end of the formulation chamber; and a target surface interface comprising a first surface configured to contact the target tissue surface and a second surface configured to be contained within the formulation chamber, wherein the target surface interface is configured to conduct heat from the target tissue surface to the cold slurry formulation within the formulation chamber; and wherein the outer dimensions of the first surface are configured to remain substantially the same when the self-contained cooling device is cooling the target tissue surface, and wherein the outer dimensions of the first surface remain substantially the same before contacting the first surface to the target tissue surface, during treatment, and after removal of the first surface from the target tissue surface.

2. The self-contained cooling device of claim 1, wherein the self-contained cooling device is configured to maintain the ocular surface at a temperature suitable for reducing ocular surface discomfort.

3. The self-contained cooling device of claim 1, wherein the first surface is configured to contact a sclera of the ocular surface.

4. The self-contained cooling device of claim 1, wherein the target surface interface comprises an opening configured to fit over a cornea of the ocular surface to avoid contact between the target surface interface and the cornea when the target surface interface is in contact with the ocular surface.

5. The self-contained cooling device of claim 1, wherein the second surface has a curved surface.

6. The self-contained cooling device of claim 1, wherein the target surface interface is configured to promote uniform cooling of the target tissue surface when the formulation chamber is filled with the cold slurry formulation.

7. The self-contained cooling device of claim 1, wherein the target surface interface comprises thermally conductive materials selected from the group consisting of Al, Cu, stainless steel, metal alloys, and combinations thereof.

8. The self-contained cooling device of claim 1, wherein the first surface of the target surface interface comprises a surface coating that protects the target tissue surface from adhering to the target surface interface.

9. The self-contained cooling device of claim 1, wherein the first surface of the target surface interface comprises a geometric design feature that protects the target tissue surface from adhering to the target surface interface.

10. The self-contained cooling device of claim 9, wherein the geometric design feature comprises one or more of a hierarchical microstructure, a hierarchical nanostructure, a bioinspired surface pattern, or a combination thereof.

11. The self-contained cooling device of claim 1, wherein the first surface of the target surface interface comprises a low surface energy material.

12. A self-contained cooling device for cooling a target tissue surface of an ocular surface of a subject, the self-contained cooling device comprising:

a housing;

a heat exchanger, wherein the heat exchanger comprises a formulation chamber configured to receive and hold a formulation, wherein the formulation is configured to freeze to a subzero temperature in a cold environment;

an aperture, wherein the aperture is configured to allow a clinician to visualize a cornea of a subject; and a target surface interface comprising a first surface configured to contact the target tissue surface and a second surface configured to be contained within the formulation chamber, wherein the target surface interface is configured to conduct heat from the target tissue surface to the formulation after the formulation has been frozen to a subzero temperature within the formulation chamber.

13. The self-contained cooling device of claim 12, wherein the cold environment is a standard freezer.

14. The self-contained cooling device of claim 12, wherein the formulation comprises water and a freezing point depressant.

15. The self-contained cooling device of claim 14, wherein the freezing point depressant is at a concentration of about 20% (wt/wt).

16. The self-contained cooling device of claim 14, wherein the freezing point depressant is glycerol.

17. The self-contained cooling device of claim 12, wherein the first surface is configured to adhere to the target tissue surface upon contact.

18. The self-contained cooling device of claim 12, wherein the target tissue surface is a sclera of the ocular surface.

19. The self-contained cooling device of claim 18, wherein the sclera is adjacent a corneal limbus.

20. The self-contained cooling device of claim 12, wherein the subzero temperature is between about −20° C. and about 0° C.

21. The self-contained cooling device of claim 12, wherein the target surface interface comprises thermally conductive materials selected from the group consisting of Al, Cu, stainless steel, metal alloys, and combinations thereof.

22. The self-contained cooling device of claim 12, wherein the self-contained cooling device is configured to be used with an accessory.

23. The self-contained cooling device of claim 22, wherein the accessory is a speculum.

24. The self-contained cooling device of claim 22, wherein the accessory is configured to hold open an eye of the subject.

25. The self-contained cooling device of claim 22, wherein the accessory is configured to protect an eyelid of the subject from subzero temperatures.

26. The self-contained cooling device of claim 22, wherein the accessory comprises silicone.

27. The self-contained cooling device of claim 12, wherein the self-contained cooling device is further configured to receive a cap, wherein the cap is configured to prevent condensation from forming on the target surface interface prior to a procedure.

28. A method of alleviating symptoms of ocular surface discomfort, the method comprising:

cooling a self-contained cooling device containing a formulation, wherein the formulation is configured to at least partially freeze when cooled, placing the self-contained cooling device in contact with a target ocular surface, allowing the self-contained cooling device to lower the temperature of the target ocular surface for a period of time sufficient to alleviate symptoms of ocular surface discomfort;

wherein the self-contained cooling device comprises a housing, a heat exchanger, wherein the heat exchanger comprises a formulation chamber configured to receive and hold the formulation, an aperture, wherein the aperture is configured to allow a clinician to visualize a cornea of a subject, a target surface interface comprising a first surface and a second surface, wherein the first surface is configured to contact the target ocular surface and the second surface is configured to be contained within the formulation chamber.

29. The method of claim 28, wherein the target surface interface is configured to adhere to the target ocular surface upon contact.

* * * * *